US008715977B2

(12) United States Patent
Murata et al.

(10) Patent No.: US 8,715,977 B2
(45) Date of Patent: May 6, 2014

(54) ETHANOL PRODUCTION FROM OCEAN BIOMASS

(75) Inventors: Kousaku Murata, Kyoto (JP); Wataru Hashimoto, Kyoto (JP); Shigeyuki Kawai, Kyoto (JP); Hiroshi Oda, Ibaraki (JP); Keishi Iohara, Ibaraki (JP); Bunzo Mikami, Kyoto (JP); Hiroyuki Takeda, Kyoto (JP); Fuminori Yoneyama, Kyoto (JP); Akihito Ochiai, Kyoto (JP)

(73) Assignees: Kyoto University, Kyoto-shi (JP); Maruha Nichiro Holdings, Inc., Tokyo (JP)

( * ) Notice: Subject to any disclaimer, the term of this patent is extended or adjusted under 35 U.S.C. 154(b) by 0 days.

(21) Appl. No.: 13/393,034

(22) PCT Filed: Aug. 25, 2010

(86) PCT No.: PCT/JP2010/064383
§ 371 (c)(1),
(2), (4) Date: Feb. 28, 2012

(87) PCT Pub. No.: WO2011/024858
PCT Pub. Date: Mar. 3, 2011

(65) Prior Publication Data
US 2012/0220004 A1 Aug. 30, 2012

(30) Foreign Application Priority Data
Aug. 28, 2009 (JP) .................................. 2009-198972

(51) Int. Cl.
| C12P 7/06 | (2006.01) |
| C12Q 1/68 | (2006.01) |
| C12P 21/06 | (2006.01) |
| C12N 1/20 | (2006.01) |
| C12N 9/02 | (2006.01) |
| C12N 9/10 | (2006.01) |
| C07H 21/04 | (2006.01) |

(52) U.S. Cl.
USPC ..................... 435/161; 435/6.15; 435/252.31; 435/69.1; 435/189; 435/193; 435/471; 536/23.2

(58) Field of Classification Search
None
See application file for complete search history.

(56) References Cited

U.S. PATENT DOCUMENTS

| 5,000,000 A | 3/1991 | Ingram et al. |
| 5,028,539 A | 7/1991 | Ingram et al. |
| 5,424,202 A | 6/1995 | Ingram et al. |
| 5,482,846 A | 1/1996 | Ingram et al. |
| 5,487,989 A | 1/1996 | Fowler et al. |
| 5,554,520 A | 9/1996 | Fowler et al. |
| 5,821,093 A | 10/1998 | Ingram et al. |
| 5,916,787 A | 6/1999 | Ingram et al. |
| 6,107,093 A | 8/2000 | Ingram et al. |
| 6,849,434 B2 | 2/2005 | Ingram et al. |
| 7,192,772 B1 | 3/2007 | Ingram et al. |
| 2005/0158836 A1 | 7/2005 | Ingram et al. |
| 2007/0172937 A1 | 7/2007 | Ingram et al. |
| 2009/0226992 A1 | 9/2009 | Javed et al. |

FOREIGN PATENT DOCUMENTS

| JP | 5 502366 | 4/1993 |
| JP | 6 505875 | 7/1994 |
| JP | 2009 529905 | 8/2009 |

OTHER PUBLICATIONS

Leu et al. The surface display of the alginate lyase on the cells of Yarrowia lipolytica for hydrolysis of alginate, Mar Biotechnol (2009), 11: 619-626, Epub Jan. 23, 2009.*
Takeda, H., et al., "Biofuel production by bacteria from alginate: Molecular breeding of ethanol-producing bacteria," Japan Society for Bioscience, Biotechnology, and Agrochemistry, vol. 2009, p. 98, (Mar. 2009) (with English translation).
Ochiai, A., et al., "Structure-to-function correlation of NADPH-dependent a-keto acid reductase involved in alginate metabolism," Vitamins, vol. 83, No. 4, p. 225, (Apr. 2009) (with English translation).
Miyamoto, Y., et al., "Super Bacteria open huge mouths Transplantation of super channel," Bionics, vol. 3, No. 4, pp. 70-71, (2006) (with English translation).
Takase, R., et al., "Ethanol production by bacteria from alginate: Molecular identification of alginate saccharification product (a-keto acid) reductase," Japan Society for Bioscience, Biotechnology, and Agrochemistry, vol. 454, p. 10 (May 31, 2008) (with English translation).
Ochiai, A., et al., "Ethanol production by bacteria from alginate: The X-ray crystal structure of exo-type lyase (enzyme for saccharification of alginate)," Japan Society for Bioscience, Biotechnology, and Agrochemistry, vol. 454, p. 9, (May 31, 2008) (with English translation).
Japanese Office Action Issued Apr. 12, 2011 in JP 2010-550772 Filed Aug. 25, 2010.
Japanese Office Action Issued Jul. 5, 2011 in JP 2010-550772 Filed Aug. 25, 2010.
International Search Report Issued Oct. 12, 2010 in PCT/JP10/64383 Filed Aug. 25, 2010.

\* cited by examiner

Primary Examiner — Iqbal H Chowdhury
(74) Attorney, Agent, or Firm — Oblon, Spivak, McClelland, Maier & Neustadt, L.L.P.

(57) ABSTRACT

An object of the present invention is to provide a method for producing ethanol from polysaccharide alginate contained in a large amounts in brown algae, using the alginate assimilation capacity of the Sphingomonas sp. strain A1 and the strong ethanol production capacity of bacteria such as Zymomonas mobilis. Specifically, a method for producing ethanol using alginate as a raw material comprises causing genes encoding proteins and enzymes involved in Sphingomonas sp. strain A1-derived alginate assimilation and genes encoding enzymes involved in ethanol production to co-exist in a single microorganism and then culturing the microorganism in a medium containing alginate.

9 Claims, 24 Drawing Sheets

(Introduced) pyruvate decarboxylase PDC (*Z.mobilis* ZM4), Alcohol dehydrogenase PDC (*Z.mobilis* ZM4)

α-KA : α-keto acid
KDG : 2-keto-3-deoxy-D-gluconate

Alg: Alginate

6% (Mutant strain)

Fig. 17
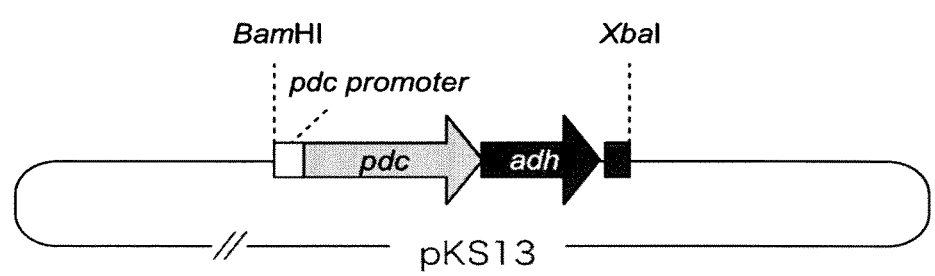
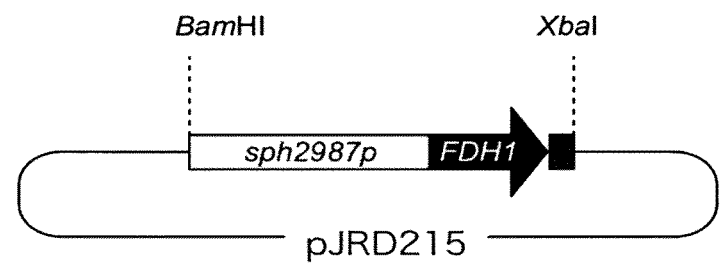

Fig. 20

```
  1 ATGCACGCGT CCTGTTGGCC GTCAGTAGGA ATTGGCCCAC AATTTCAGTC GAATCCCCCC
    P1 ──────────────────────────────▶
 61 GAACCTTCGC CCGGAGTTCT CAGCATGCGA ATTGCAGTGT TCGATACCCA CCCCTACGAT
121 GAACAGGCCC TCACGGCCGC CAACGCCAGT TTTGGACACG AACTGGTCTT CTTTGAAGAG
181 CGCTTGCACG ATAAGACCGT CGAGCTCGCC AAAGGCTTCG ACGTTGTGTG TCCTTTCGTC
241 AATTGCCGCC TGCCGGCGGA GGTCATGCAT CGCCTGGCCG AACTCGGCGT CGGTCTGGTG
301 GCGCTACGCG CGGCCGGTTT CAATGGCATT GACATCGCTG CCGCCCAGCA CGAGGGCGTC
361 AAAGTGGCGC GCGTGCCGGC TTATTCGCCG GAAGCCGTGG CCGAACACAC TTTTGCGCTC
421 ATCCTGACGC TGGTGCGCAA GACCCATCGC GCATACAACC GTGTGCGCGA GCAGAACTTT
481 TCGCTCGACG GCCTTGAAGG CTTCACCCTC CACGGCAAGA CCTTCGGTTC GCTCGGCGCA
                                    ◀────────────────────────── P3
541 GGCCGCATTG GCCAATGCTC GATGCGCATC GCCAAAGGCC TGGGCATGAA GCTGCTGGCC
    P4 ──────────────────────────────▶
601 TACGATCCGT ACGAAAACCC CAAGATCGCC GAAGAAGTCG GGTTCCAGTA CGCCTCGCTG
661 AACGACGTGC TGGCCCAGGC CGACGTGATC TCGCTGCACC TGCCCCTGAC CGACCAGAGC
721 CACCACATCA TCAGCCGCGA CTCGCTGGCG CGCACCAAAC GCGGCGTCGT GATTGCCAAC
781 ACCAGTCGCG GTGGACTGAT CGACACGGTG GCGTTGATCG ACGCCCTCAA GAGCGGACAG
841 GTTGGCGGCG TGGGTCTGGA CGTCTATGAA ATGGAGGAAG GCGTGTTCTT TCACGATCTG
901 TCCGACCGCC CCTTGCAGGA CGATCTGCTG GCGCGCCTGA TGATCTTCCC CAATGCCCTG
961 ATCACCTCAC ACCAGGGCTT CCTGACCCGC GAGGCATTGC ACGCCATCGC CCAGACCACG
1021 CTGGGCAACG TTACCGCCTT CGAACGCAAG GAACCGCTGG CCAACGAGGT GATCTCAGCC
                                    ◀────────────────────────── P2
1081 TGA (SEQ ID NO:46)
```

Fig. 21

```
   1 GTGATCGTTG GTGCCGGTGG TGCCGGCATG CGCGCCGCGA TTCAACTCTC CGAATCCGGC
                                                 P1 ─────────────────────
  61 CTGAAGACAG CCGTTCTGTC CAAGGTTTTC CCGACCCGTT CGCACACGGT TGCGGCGCAA
     ──────────▶
 121 GGCGGTGTGT CCGCTTCGCT GGGTAACTCG GAGCCCGATC ACTGGCACTG GCACATGTAC
 181 GACACCGTCA AGGGTTCCGA CTGGCTCGGC GACCAGGACG CGATCGAGTT CATGTGCAAG
 241 CAGGCCCCGC AAGTCGTGGT GGAACTCGAA CATTACGGCA TGCCGTTCGA CCGTCTGGAC
 301 AACGGCAAGA TTTACCAACG CCCGTTCGGC GGTCATATGT CGAACTTCGG CGACAAGCCC
 361 GTGCGCCGCG CCTGCGCCGC AGCCGACCGC ACCGGTCATG CCATGCTGCA CGCGCTCTAC
 421 CAGCGCAACG TGCGCGCAAA CACGCAGTTC TTCGTCGAAT GGATGGCGCT CGATCTATTG
 481 CGTGCTGAAG ACGGCCGCGT GCTGGGCGTG ATCGCTATGG AAATGGAAAC CGGCGACATC
 541 ACCGTATTCC AGGCCAAGGC GACGTTGTTC GCTACCGGTG GTGCAGGGCG CATCTTTGCT
                                                        ───────────── P3
 601 TCGTCGACCA ACGCTTTCAT CAACACGGGT GACGGCCTTG GCATGGCGGC ACGTGCTGGC
 661 ATTCCGCTGG AAGACATGGA GTTCTGGCAA TTCCACCCGA CCGGCGTGGC TGGCGCGGGC
 721 GTGCTGATCA CCCAAGGCGT GCGTGGCGAA GGCGGCATTC TGCGCAACAG CGCAGGCGAA
 781 CGCTTCATGG AGCGCTACGC CCCGAACGCC AAGGATCTGG CTTCGCGCGA CGTCGTCTCG
 841 CGCGCCATGG TCACCGAAAT CAACGAAGGT CGCGGTTGCG GCCCGGCCAA GGATCACGTG
 901 CTGCTCGACA TCACGCACCT TGACCCGAAC ACGATCATGA CCCGCCTGCC GGGTATTCGC
 961 GAAATCTCGA TCCAGTTCGC CGGCGTCGAC CCGATCAAGG CTCCGATTCC GGTCGTGCCG
1021 ACCTGTCACT ATCAGATGGG TGGCATTCCG ACGAACTACC TCGGCGAAGT CGTCGTGCAC
1081 GACCAGATCG TGCCTGGCTT CTACGCTGCA GGCGAGTGCG CATGCGCCTC GGTGCACGGT
1141 GCGAACCGCC TGGGCACGAA TTCGCTGCTC GACCTGCTTG TGTTCGGCAA GAGTTCGGGC
                      P4 ─────────────────────────────────────▶
1201 GAGTCGATGG TCGACTTCAT CAAGGGCGAA CCCGCCGCCG TGCCGGACAT TCCGCAAGAG
1261 CAGATCGACC GTGCGTTGGC GCGCGTAGAT CGCCTGGACT CGCAGCGCGA CGGTGCCAAT
1321 GTGCATGAGA CGCGCGCCGC CATGCAGCGC ACAATGCAGA ACCACTGTGG CGTGTTCCGT
1381 TTCAAGGACA TGCTGGCGCA GGGCGTGGAC AAGATCACGG AGGTCGAAGC CGCTGTGCGT
1441 CAGACCGAGA TCAAGGACAA GTCCAAGGTG TGGAACACCG CACGCCAGGA AGCACTGGAA
1501 CTGGACAACC TCATCGAAGT CGCCAAGGCG ACGATGGTGT CGGCCAATGC GCGTACCGAA
1561 TCGCGTGGCG CACACGTGCG CGACGACGCT CCGGATACCC CGCAACACCC GAACGGCCGC
1621 GACGACGAGA ACTGGCTCAA GCACACCCTT TGGTACAAGG AGGGTAGCCG CCTGGACTAC
1681 AAACCCGTCA AGCTCAAGCC GCTGTCCGTT GAAACGATCG CGCTGAAGAC GCGCGCGTAC
1741 TGA (SEQ ID NO:47)         ◀────────────────────────── P2
```

ETHANOL PRODUCTION FROM OCEAN BIOMASS

TECHNICAL FIELD

Technology enabling ethanol production from polysaccharide alginate that is contained in large amounts in marine-area-derived biomass and particularly in brown algae is provided.

BACKGROUND ART

Brown algae such as Sargasso (scientific name: *Sargassum fulvellum*) can grow in large amounts and do not compete with food resources, so that they are expected to serve as raw materials for production of biofuel. However, a major component of brown algae is alginate (acidic polysaccharide), accounting for about 30% to 60% of the dry alga body. Studies that have been conducted to date focus mainly on the use of cellulose in brown algae. A method for converting alginate (polysaccharide comprising uronic acid (saccharide with a carboxylated terminus (at position 6) of the main chain), which is a major component of brown algae, to biofuel ethanol, has not yet been established.

Technology for producing ethanol from alginate has been examined. It has been reported that a pit-forming bacterium of a *Sphingomonas* sp. strain A1 (hereinafter, referred to as the "strain A1"), produces a trace amount of ethanol from alginate (see non-patent document 1). However, the ethanol productivity of the strain A1 is extremely low, so that production thereof on a commercial basis and/or commercialization thereof is extremely difficult.

The metabolic pathway for production of ethanol from alginate has been revealed to some extent. It has been inferred that the strain A1 degrades alginate to a monosaccharide (α-keto acid) with endo- and exo-lyases, converts it to 2-keto-3-deoxy-D-gluconate (KDG) with α-keto acid reductase, and converts the resultant to pyruvic acid by a reaction with enzymes, A1-K (kinase) and A1-A (aldolase) (see non-patent document 2). Pyruvic acid mainly enters the TCA cycle and is then used for ATP (energy source) production under aerobic conditions, and it produces ethanol in a microaerophilic environment.

The pathway from uronic acid (monosaccharide) to pyruvic acid in bacteria of the genus *Pseudomonas* has been reported, and the presence of α-keto acid reductase has also been reported (see non-patent documents 3 and 4). Also, an enzyme group (KDG-kinase, KDG-aldolase) involved in metabolism of 2-keto-3-deoxy-D-gluconate (KDG) and genes thereof in *Escherichia coli* have been revealed (http://www.genome.jp/dbget-bin/get_pathway?org_name=eco&mapno=00040).

Meanwhile, a gram-negative bacterium *Zymomonas mobilis* (lacking alginate assimilation capacity) is known as a bacterium having strong ethanol production capacity. It has been reported that *Zymomonas mobilis* produces ethanol from glucose, fructose, or sucrose with efficiency as high as 2.5 times greater than that of yeast. Furthermore, ethanol production technology that involves incorporating *Zymomonas mobilis*-derived pyruvate decarboxylase and alcohol dehydrogenase into *Escherichia coli* and thus causing ethanol production from glucose has been reported (see patent document 1). This strain is currently industrially used as the strain KO11 (ATCC55124) for bioethanol production from cellulose-based biomass. Also, incorporation of *Zymomonas mobilis*-derived pyruvate decarboxylase and alcohol dehydrogenase into Gram-negative bacteria (e.g., *Erwinia, Klebsiella*, and *Xanthomonas*) other than *Escherichia coli* has also been reported (see patent document 2).

PRIOR ART DOCUMENTS

Patent Documents

Patent document 1 JP Patent Publication (Kohyo) No. 5-502366 A (1993)
Patent document 2 JP Patent Publication (Kohyo) No. 6-505875 A (1994)

Non-Patent Documents

Non-patent document 1 Akihito Ochiai et al., "Bacterial Ethanol Production from Alginate: Molecular Identification of Reductase for Alginate Saccharification Product (α-keto acid)," JSBBA Kansai (Kansai branch, the Japan Society for Bioscience, Biotechnology, and Agrochemistry), the $454^{th}$ Lecture Summaries, Presentation No. 9 (2008)

Non-patent document 2 Ryuichi Takase et al., "Bacterial Ethanol Production from Alginate: Molecular Identification of Reductase for Alginate Saccharification Product (α-keto acid)," JSBBA Kansai (Kansai branch, the Japan Society for Bioscience, Biotechnology, and Agrochemistry), the $454^{th}$ Lecture Summaries, Presentation No. 10 (2008)

Non-patent document 3 Preiss, J., and Ashwell, G. (1962) J. Biol. Chem. 237, 309-316

Non-patent document 4 Preiss, J., and Ashwell, G. (1962) J. Biol. Chem. 237, 317-321

SUMMARY OF THE INVENTION

Problem to Be Solved by the Invention

An object of the present invention is to provide a method for producing ethanol from polysaccharide alginate that is contained in large amounts in brown algae, using the alginate assimilation capacity of the *Sphingomonas* sp. strain A1 and the strong ethanol production capacity of bacteria such as *Zymomonas mobilis*.

Means for Solving the Problem

A method for producing ethanol from alginate that comprises incorporating an enzyme involved in ethanol production into a microorganism having alginate assimilation capacity has not yet been disclosed. The use of the capacity of bacteria such as *Zymomonas mobilis* having strong ethanol production capacity for ethanol production from brown algae has never been attempted. Moreover, no transformed strain that becomes capable of metabolizing alginate as a result of incorporation of an enzyme system of the strain A1 or the like involved in alginate assimilation into a microorganism with high ethanol productivity (e.g., *Escherichia coli* strain KO11) has been reported.

In order to produce ethanol from polysaccharide alginate that is contained in large amounts in brown algae using the alginate assimilation capacity of *Sphingomonas* sp. strain A1 and the strong ethanol production capacity of bacteria such as *Zymomonas mobilis*, the present inventors introduced pyruvate decarboxylase and alcohol dehydrogenase from bacteria such as *Zymomonas mobilis* having strong ethanol production capacity into the strain A1, so as to obtain a transformed strain.

Meanwhile, a transformed strain was obtained by imparting the alginate incorporation and/or assimilation capacity of the strain A1 to ethanol-producing bacteria (*Escherichia coli* strain KO11).

As a result, the alginate assimilation capacity of the *Sphingomonas* sp. strain A1 and the strong ethanol production capacity of bacteria such as *Zymomonas mobilis* could be imparted to one microorganism. The present inventors succeeded in efficient ethanol production in a large amount from alginate through the breeding of the microorganism and thus completed the present invention.

Specifically, the present invention is as follows.

[1] A method for producing ethanol using alginate as a raw material, comprising causing genes encoding proteins and enzymes involved in alginate assimilation derived from the *Sphingomonas* sp. strain A1 to coexist with genes encoding enzymes involved in ethanol production in a single microorganism and then culturing the microorganism in a medium containing alginate.

[2] The method for producing ethanol using alginate as a raw material according to [1], wherein the proteins and the enzymes involved in alginate assimilation derived from *Sphingomonas* sp. strain A1 are an ABC transporter, alginate-binding proteins, endo-/exo-type alginate lyases, keto acid reductase, kinase, and aldolase.

[3] The method for producing ethanol using alginate as a raw material according to [1] or [2], wherein the enzymes involved in ethanol production are pyruvate decarboxylase and alcohol dehydrogenase.

[4] The method for producing ethanol using alginate as a raw material according to [3], wherein the enzymes involved in ethanol production are *Zymomonas mobilis*-derived pyruvate decarboxylase and alcohol dehydrogenase.

[5] The method for producing ethanol using alginate as a raw material according to any one of [1] to [4], wherein the microorganism further has at least one of the following properties (i) to (iii):
(i) the genes encoding the enzymes involved in ethanol production are controlled by a *Sphingomonas* sp. strain A1-derived SPH2987 gene promoter and thus are expressed at high levels;
(ii) multiple copies of the genes encoding the enzymes involved in ethanol production are introduced; and
(iii) a gene encoding formate dehydrogenase, which is an enzyme of an NADH regeneration system, also coexists with the other genes.

[6] The method for producing ethanol using alginate as a raw material according to any one of [1] to [5], wherein in the microorganism, a gene involved in lactic acid synthesis, is further knocked out.

[7] The method for producing ethanol using alginate as a raw material according to [1], comprising culturing the transformed *Sphingomonas* sp. strain A1 into which genes encoding *Zymomonas mobilis*-derived pyruvate decarboxylase and alcohol dehydrogenase have been introduced in a medium containing alginate.

[8] The method for producing ethanol using alginate as a raw material according to [1], comprising introducing genes encoding the proteins and the enzymes involved in the alginate assimilation capacity of the *Sphingomonas* sp. strain A1 into an *Escherichia coli* strain KO11 into which genes encoding *Zymomonas mobilis*-derived pyruvate decarboxylase and alcohol dehydrogenase have been introduced, and then culturing the microorganism in a medium containing alginate.

[9] The method for producing ethanol using alginate as a raw material according to [8], wherein the proteins and the enzymes involved in alginate assimilation derived from *Sphingomonas* sp. strain A1 are an ABC transporter, alginate-binding proteins, endo-/exo-type alginate lyases, keto acid reductase, kinase, and aldolase.

[10] The method for producing ethanol using alginate as a raw material according to any one of [1] to [9], wherein an immobilized microorganism is used.

[11] A microorganism capable of producing ethanol using alginate as a raw material, having genes encoding proteins or enzymes involved in alginate assimilation derived from *Sphingomonas* sp. strain A1 and genes encoding enzymes involved in ethanol production, wherein the genes coexist.

[12] The microorganism capable of producing ethanol using alginate as a raw material according to [11], wherein the enzymes involved in ethanol production are pyruvate decarboxylase and alcohol dehydrogenase.

[13] The microorganism according to [12], which is of a transformed *Sphingomonas* sp. strain A1 prepared by introducing genes encoding *Zymomonas mobilis*-derived pyruvate decarboxylase and alcohol dehydrogenase into a *Sphingomonas* sp. strain A1.

[14] The microorganism according to [12], which is of an *Escherichia coli* strain KO011 prepared by introducing genes encoding proteins and enzymes involved in the alginate assimilation capacity of the *Sphingomonas* sp. strain A1 into an *Escherichia coli* strain KO11 prepared by introduction of genes encoding *Zymomonas mobilis*-derived pyruvate decarboxylase and alcohol dehydrogenase.

[15] The microorganism according to any one of [11] to [14], further having at least one of the following properties (i) to (iii):
(i) the genes encoding the enzymes involved in ethanol production are controlled by a *Sphingomonas* sp. strain A1-derived SPH2987 gene promoter and thus are expressed at high levels;
(ii) multiple copies of the genes encoding the enzymes involved in ethanol production are introduced; and
(iii) a gene encoding formate dehydrogenase, which is an enzyme of an NADH regeneration system, also coexists with the other genes.

[16] The microorganism according to any one of [11] to [15], wherein a gene involved in lactic acid synthesis is further knocked out.

This description includes part or all of the contents as disclosed in the description and/or drawings of Japanese Patent Application No. 2009-198972, which is a priority document of the present application.

Effect of the Invention

Ethanol production from polysaccharide alginate that is contained in large amounts in marine-area-derived biomass and particularly in brown algae becomes possible. Specifically, a novel method for producing ethanol is developed, which is characterized by using biomass as a raw material that does not compete with food resources, can be reproduced in a marine area, and comprises mainly uronic acid, without using any raw material (e.g., cellulose and starch) composed mainly of glucose that must compete with food resources. A large social impact is expected by this achievement.

BRIEF DESCRIPTION OF THE DRAWINGS

FIG. 10A is a schematic diagram showing a pUC18-sph####p-adh plasmid, FIG. 10B is a schematic diagram showing a pKS13-sph####p-adh plasmid, FIG. 10C is a schematic diagram showing a pUC18-sph2987p-pdc plasmid, and FIG. 10D is a schematic diagram showing a pKS13-sph2987p-pdc-sph2987p-adh plasmid. In these FIG. 10A to FIG. 10D, #### denotes gene No.

FIG. 13A shows growth curves and FIG. 13B shows the concentrations of alginate in medium. Each arrow in FIG. 13 indicates the addition of alginate (a long arrow indicates the addition of 1 g of alginate and a short arrow indicates the addition of 0.5 g of alginate). FIG. 13C shows the concentrations of ethanol in medium. In FIG. 13, black circles show the results of the strain EPv14 and white circles show the results of the wild-type strain A1.

FIG. 14A is a schematic diagram showing a pUC18-sph2987p-adh-pdc plasmid, FIG. 14B is a schematic diagram showing a pKS13-sph2987p-adh-pdc plasmid, and FIG. 14C is a schematic diagram showing a pKS13-(sph2987p-adh-pdc)$_2$ plasmid.

FIG. 16A shows a growth curve and FIG. 16B shows the concentrations of alginate in medium. Each arrow in FIG. 16 indicates the addition of alginate (a long arrow indicates the addition of 1 g of alginate and a short arrow indicates the addition of 0.5 g of alginate). FIG. 16C shows the concentrations of ethanol in medium.

FIG. 17 shows schematic diagrams of plasmids used in Example 8. FIG. 17A shows a plasmid for expression of PDC and ADH, which was introduced into the strain EPv2. FIG. 17B shows a plasmid for expression of FDH1. A strain EPv10 retains two plasmids shown in FIG. 17A and FIG. 17B.

FIG. 18A shows growth curves and FIG. 18B shows the concentrations of alginate in medium. Each arrow in FIG. 18 indicates the addition of alginate (a long arrow indicates the addition of 1 g of alginate and a short arrow indicates the addition of 0.5 g of alginate). FIG. 18C shows the concentrations of ethanol in medium. In FIG. 18, each black circle indicates a result of the strain EPv10 and each white circle indicates a result for EPv2.

FIG. 20 shows the nucleotide sequence of a strain A1 ldh gene homolog. In FIG. 20, arrows P1 to P4 indicate primer positions.

FIG. 21 shows the nucleotide sequence of a strain A1 sdh gene homolog. In FIG. 21, arrows P1 to P4 indicate primer positions.

FIG. 22A shows a plasmid prepared by cloning a gene fragment to be disrupted into pUC18. FIG. 22B shows a gene fragment linearized by subjecting the plasmid in FIG. 22A to inverse PCR using primers (thin arrows) designed at the center of the gene to be disrupted. FIG. 22C shows a plasmid prepared by ligating the gene fragment in FIG. 22B to the Km$^r$ cassette. FIG. 22D shows a plasmid prepared by inserting an insert fragment amplified using the thin arrows shown in FIG. 22C into pKTY320. The plasmid shown in FIG. 22D was introduced into a wild-type strain A1, so as to perform gene disruption.

EMBODIMENTS FOR CARRYING OUT THE INVENTION

The present invention is described in detail as follows.

In the present invention, ethanol is produced using the alginate assimilation capacity of the *Sphingomonas* sp. strain A1 and the strong ethanol production capacity of bacteria such as *Zymomonas mobilis*, and polysaccharide alginate contained in large amounts in brown algae as a raw material. Specifically, proteins and enzymes involved in alginate assimilation capacity of the *Sphingomonas* sp. strain A1, pyruvate decarboxylase (PDC) and alcohol dehydrogenase (ADH) derived from bacteria such as *Zymomonas mobilis* having strong ethanol production capacity are caused to coexist in a microorganism, alginate is incorporated into the microorganism, and thus ethanol is produced using alginate as a raw material within the microorganism. Here, examples of the proteins and the enzymes involved in alginate assimilation capacity include proteins involved in incorporation of alginate into a microorganism, enzymes that degrades alginate to generate α-keto acid, and keto acid-metabolizing enzymes that form pyruvic acid from keto acid. Examples of proteins involved in incorporation of alginate into a microorganism include ABC transporter(s) and alginate-binding proteins. An example of enzymes that degrade alginate to generate α-keto acid is endo-/exo-type alginate lyase. Examples of keto acid-metabolizing enzymes include keto acid reductase, kinase (e.g., 2-keto-3-deoxygluconokinase (EC 2.7.1.45)), and aldolase (e.g., 2-keto-3-deoxy-6-phosphogluconate aldolase (EC 4.1.2.14)).

Figure 1:
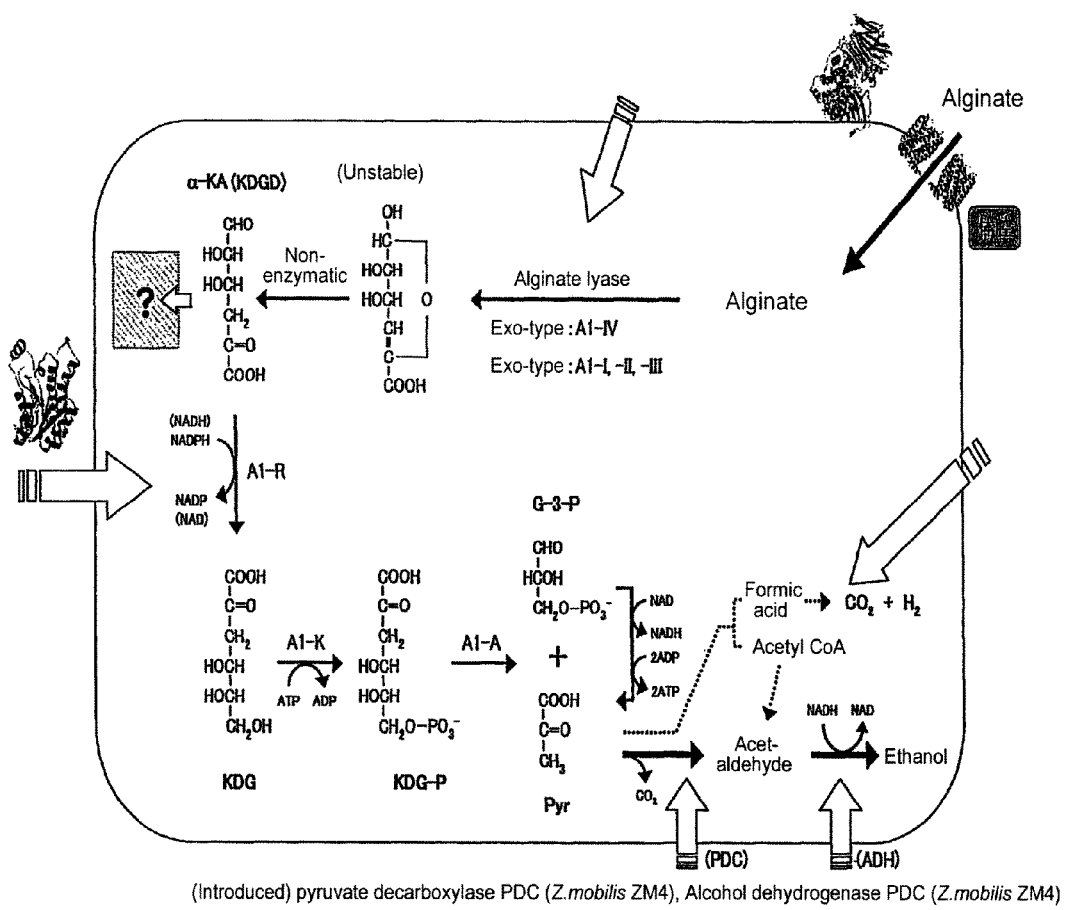
FIG. 1 shows the reaction pathway that takes place in a microorganism, ranging from alginate incorporation to ethanol generation.

FIG. 1 shows the reaction pathway that takes place in a microorganism, ranging from alginate incorporation to ethanol generation.

The *Sphingomonas* sp. strain A1 (described later) originally has enzymes involved in alginate assimilation capacity.

An example of the method for producing ethanol using the alginate assimilation capacity of the *Sphingomonas* sp. strain A1 and the ethanol production capacity of *Zymomonas mobilis*, and polysaccharide alginate as a raw material is a method that comprises introducing genes encoding pyruvate decarboxylase and alcohol dehydrogenase into the *Sphingomonas* sp. strain A1 and then causing co-expression of the 2 types of enzyme in the *Sphingomonas* sp. strain A1. The *Sphingomonas* sp. strain A1 forms pits on the cell surface layer in the presence of alginate, incorporates alginate as it is (in the form of polysaccharide) into the microorganism, and then degrades alginate. Specifically, the *Sphingomonas* sp. strain A1 incorporates polysaccharide alginate through the pits and ABC transporter(s) into cells, and then degrades it to monosaccharides using endo-/exo-type alginate lyase. Monosaccharides are cleaved non-enzymatically to result in keto acid, and then converted by a keto acid-metabolizing enzyme group to pyruvic acid and glyceraldehyde-3-phosphate (G-3-P). Most of them are thought to be used for energy production in the TCA cycle, but few of them are converted to ethanol and then the ethanol is released into a medium. About 0.003% to 0.005% ethanol is detected from a medium of a wild-type strain A1.

The *Sphingomonas* sp. strain A1 is described in Hisano, T. et al, Biochem. Biophys. Res. Commun., 220, 979-982, and it was isolated by Prof. Kousaku Murata et al., the Graduate School of Agriculture, Kyoto University.

Resistance to ethanol may be imparted to the *Sphingomonas* sp. strain A1 (which may be treated to become resistant to or develop tolerance to ethanol). For example, acclimatization culture is performed in a medium containing ethanol and then ultraviolet irradiation is performed to induce random mutation, so that an ethanol-resistant strain can be obtained. In the present invention, the thus-isolated 3% to 10% ethanol-resistant strain, such as a 6% ethanol-resistant strain, may be used.

The origins of the genes encoding pyruvate decarboxylase and alcohol dehydrogenase, which are introduced into the *Sphingomonas* sp. strain A1, are not limited. Genes encoding enzymes derived from bacteria having strong ethanol production capacity can be used, such as microorganisms belonging to the genus *Zymomonas* (e.g., *Zymomonas mobilis*), microorganisms belonging to the genus *Saccharomyces* (e.g., *Saccharomyces cerevisiae*), and microorganisms belonging to the genus *Schizosaccharomyces* (e.g., *Schizosaccharomyces pombe*). Preferably, genes encoding *Zymomonas mobilis*-derived pyruvate decarboxylase and alcohol dehydrogenase are used. Gram-negative bacterium, *Zymomonas mobilis*, to be used for brewing tequila, for example, has very high ethanol production capacity because of their Entner-Doudoroff pathway (ED pathway) and incomplete TCA cycle. The genes encoding pyruvate decarboxylase and alcohol dehydrogenase can be amplified by PCR or the like and isolated from microorganisms based on known gene information of each gene.

The nucleotide sequences of the genes encoding *Zymomonas mobilis*-derived pyruvate decarboxylase and alcohol dehydrogenase are shown in SEQ ID NO: 1 and SEQ ID NO: 2, respectively.

In the present invention, instead of DNA consisting of the nucleotide sequence shown in SEQ ID NO: 1, DNA that is capable of hybridizing under stringent conditions to DNA consisting of a sequence complementary to that of the DNA consisting of the nucleotide sequence shown in SEQ ID NO: 1 and encodes a protein having pyruvate decarboxylase activity can be used. Moreover, instead of DNA consisting of the nucleotide sequence shown in SEQ ID NO: 2, DNA that is capable of hybridizing under stringent conditions to DNA consisting of a sequence complementary to that of the DNA consisting of the nucleotide sequence shown in SEQ ID NO: 2 and encodes a protein having alcohol dehydrogenase activity can also be used. Such a DNA that is capable of hybridizing under stringent conditions refers to DNA that can be identified after DNA hybridization at 68° C. using a filter (on which the DNA has been immobilized) in the presence of 0.7 M to 1.0 M NaCl followed by washing at 68° C. with 0.1-2× SSC solution (1×SSC consists of 150 mM NaCl and 15 mM sodium citrate). Alternatively, such a DNA also refers to DNA that can form a hybrid after DNA transcription and immobilization by the Southern blotting method onto a nitrocellulose membrane, followed by overnight reaction at 42° C. in a hybridization buffer (50% formamide, 4×SSC, 50 mM HEPES (pH 7.0), 10×Denhardt's solution, 100 µg/ml salmon sperm DNA). Further examples of such a DNA that can be used herein include: DNA having at least 85%, preferably 90% or more, further preferably 95% or more, and particularly preferably 97% or more sequence identity with the nucleotide sequence shown in SEQ ID NO: 1 as calculated using BLAST or the like (using e.g., default parameters; that is, initial setting parameters) and encoding a protein having pyruvate decarboxylase activity; and DNA having at least 85%, preferably 90% or more, further preferably 95% or more, and particularly preferably 97% or more sequence identity with the nucleotide sequence shown in SEQ ID NO: 2 and encoding a protein having alcohol dehydrogenase activity.

In the present invention, genes encoding the above 2 types of enzyme are introduced into the *Sphingomonas* sp. strain A1, so that a recombinant *Sphingomonas* sp. strain A1 containing foreign genes encoding the 2 types of enzyme is prepared.

A recombinant may be prepared by inserting the genes encoding the above enzymes into an expression vector and then transforming the *Sphingomonas* sp. strain A1 using the expression vector.

As an expression vector(s) into which the genes encoding the above 2 types of enzyme are introduced, two expression vectors into which the genes encoding 2 types of enzymes are separately introduced, or one expression vector into which the genes encoding the 2 types of enzyme are inserted (double-gene expression vector) can be used. When a plurality of genes are introduced into one expression vector, gene expression may be controlled by different promoters, or a plurality of genes are ligated downstream of one promoter, so as to be able to control the expression of the plurality of genes by the single promoter. Preferably, the expression of both genes is controlled by one promoter. At this time, an expression vector containing a plurality of multi-cloning sites may be used. Genes encoding enzymes should be incorporated into an expression vector(s) so that the functions of the genes can be exhibited. Hence, in addition to a promoter(s) and the above genes encoding the enzymes, a sequence containing a terminator, and if desired, a cis element such as an enhancer, splicing signal comprising a splice donor site existing on the 5' terminal side of intron and a splice acceptor site existing on the 3' terminal side of intron, polyA additional signal, a selection marker, a ribosome binding sequence (SD sequence), and the like can be operably linked to an expression vector(s) to be used herein. In addition, examples of a selection marker include a dihydrofolate reductase gene, an ampicillin resistance gene, and a neomycin resistance gene.

A method to be employed for insertion of genes encoding enzymes into an expression vector(s) involves, first, cleaving purified DNA with an appropriate restriction enzyme, inserting the resultant to a restriction enzyme site or a multi-cloning site of an appropriate vector DNA, and thus ligating it to the expression vector(s), for example. Also, when the genes encoding the 2 types of enzyme are simultaneously inserted to one expression vector for co-expression, an expression vector containing a plurality of multi-cloning sites may be used.

As an example, a sequence prepared by linking a pdc gene promoter region, ORF of the pdc gene, ORF of the adh gene, and an adh gene terminator region may be introduced into one expression vector.

Also, a microorganism having high ethanol production capacity can be obtained using a high expression promoter that enables high-level expression, other than a pdc gene promoter or an adh gene promoter. Such a high expression promoter can be obtained by selecting a high expression promoter from among gene promoters of the *Sphingomonas* sp. strain A1. For example, genes that are expressed at high levels are selected based on the genome sequence information of the *Sphingomonas* sp. strain A1 and then promoters of the genes can be used. Specifically, genes encoding enzymes involved in ethanol production are controlled by a high expression promoter derived from the *Sphingomonas* sp. strain A1, so that high-level expression can be achieved. Whether or not the thus selected promoter leads to high-level expression of the pdc gene and the adh gene of the present invention can be examined by ligating the pdc gene and the adh gene to the selected promoter and then confirming the presence or the absence of an increase in expression level. An example of such a high expression promoter is a promoter of an SPH2987 gene the nucleotide sequence of which is shown in SEQ ID NO: 25.

Furthermore, a microorganism having high ethanol production capacity can also be obtained by increasing the number of copies of the pdc gene and the adh gene to be introduced into the *Sphingomonas* sp. strain A1. In this case, a plurality of or a large number of copies of the pdc gene and the adh gene are incorporated into a plasmid and then the plasmid is introduced into the *Sphingomonas* sp. Strain A1. The number of copies is not limited and ranges from 2 to 100 copies, preferably ranges from 2 to 50 copies, further preferably ranges from 2 to 40 copies, 2 to 30 copies, 2 to 20 copies, 2 to 10 copies, or 2 to 5 copies, or is 2 copies.

Examples of expression vectors into which genes encoding enzymes are inserted are not particularly limited, as long as the vectors are broad-host vectors (IncP, IncQ, and IncW plasmids) replicable within the *Sphingomonas* sp. strain A1, include plasmid DNA and phage DNA and specifically pKS13, pJRD215, and pUFR027.

A transformant can be obtained by introducing a recombinant vector, into which genes encoding enzymes have been inserted, into a host so that the target genes can be expressed.

A method for introducing a recombinant vector into a microorganism is not particularly limited, as long as it is a method for introducing DNA into a microorganism. Examples of such a method include a method using calcium ions [Cohen, S. N. et al.: Proc. Natl. Acad. Sci., U.S.A., 69: 2110 (1972)], an electroporation method, and a tri-parental mating method.

Furthermore, an enzyme of an NADH regeneration system for regeneration of a coenzyme (NADH) required for ADH activity may be introduced into a microorganism. The term "enzyme of an NADH regeneration system" refers to an enzyme having activity (coenzyme-regenerating activity) of converting oxidized NAD (oxidized with the progress of an enzyme reaction that requires a reduced coenzyme (NADH)) into reduced NAD. Examples of an enzyme of the coenzyme regeneration system include formate dehydrogenase, glucose dehydrogenase (GDH), alcohol dehydrogenase, aldehyde dehydrogenase, and glucose-6-phosphate dehydrogenase. Particularly, formate dehydrogenase (FDH) is preferred. An enzyme of the coenzyme regeneration system derived from a microorganism can be used. For example, enzymes of yeast and enzymes of microorganisms belonging to the genus *Bacillus*, the genus *Thiobacillus*, the genus *Pseudomonas*, and the like can be used. Particularly, an enzyme of the coenzyme regeneration system of yeast (*Saccharomyces cerevisiae*) is preferred. A gene encoding an enzyme of the coenzyme regeneration system can be prepared based on known sequence information from a microorganism by a known method such as a method using amplification means (e.g., PCR) or a chemical synthesis method. A gene encoding an enzyme of the coenzyme regeneration system is incorporated into a plasmid and then the plasmid may be introduced into the *Sphingomonas* sp. strain A1. At this time, as a promoter, the promoter of the above SPH2987 gene may be used.

Furthermore, the pathway for the synthesis of lactic acid and/or succinic acid and preferably the pathway for the synthesis of lactic acid, which are metabolites from pyruvic acid and accumulated at high levels, may be blocked. Partial or complete blocking of the lactic acid and succinic acid synthetic pathway can result in production of ethanol at even higher levels. For partial or complete blocking of the lactic acid and/or succinic acid synthetic pathway, genes encoding enzymes involved in synthesis of these substances are knocked out. An example of an enzyme for lactic acid synthesis is lactate dehydrogenase (LDH) and an example of an enzyme for succinic acid synthesis is fumarate reductase (SDH). Gene knockout can be performed by a known method, such as homologous recombination.

Furthermore, an example of the method for producing ethanol using polysaccharide alginate as a raw material, and using the alginate assimilation capacity of the *Sphingomonas* sp. strain A1, and the ethanol production capacity of bacteria such as *Zymomonas mobilis* is a method that comprises introducing genes encoding proteins and enzymes involved in the alginate assimilation capacity of the *Sphingomonas* sp. strain A1 into a microorganism having genes encoding the pyruvate decarboxylase and the alcohol dehydrogenase derived from bacteria such as *Zymomonas mobilis*, and causing the microorganism to incorporate alginate and thus to produce ethanol using alginate as a raw material within the microorganism. Such a microorganism having genes encoding pyruvate decarboxylase and alcohol dehydrogenase derived from bacteria such as *Zymomonas mobilis* is a microorganism into which the above genes encoding pyruvate decarboxylase and alcohol dehydrogenase derived from bacteria such as *Zymomonas mobilis* have been introduced. Examples of such a microorganism include *Escherichia coli* (*E. coli*), microorganisms belonging to the genus *Sphingomonas*, microorganisms belonging to the genus *Pseudomonas*, microorganisms belonging to the genus *Bacillus*, and microorganisms belonging to the genus *Corynebacterium*. In particular, an *Escherichia coli* strain KO11 into which genes encoding *Zymomonas mobilis*-derived pyruvate decarboxylase and alcohol dehydrogenase have been introduced can be appropriately used. The *Escherichia coli* strain KO11 is described in Ohta, K. et al., Appl. Environ. Microbiol., 57, 893-900 or U.S. Pat. No. 5,821,093. Also, the *Escherichia coli* strain KO11 can be obtained from the ATCC (American Type Culture Collection) (ATCC55124).

Figure 2:
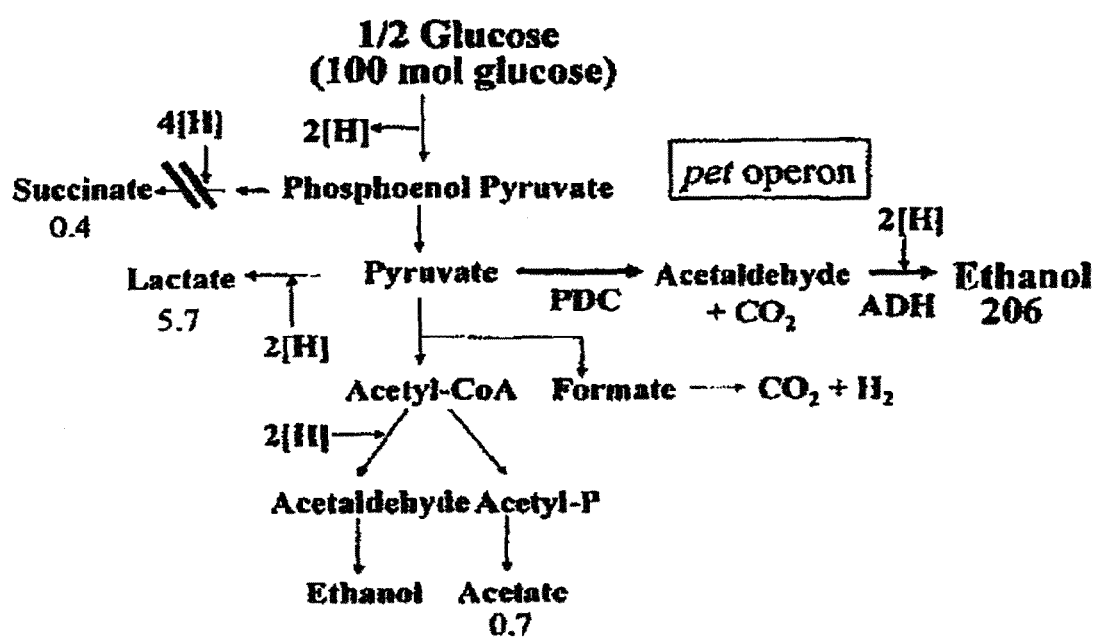
FIG. 2 shows the ethanol production pathway of an *Escherichia coli* strain KO11.

A pathway for ethanol synthesis using acetyl CoA as a substrate is originally present in *Escherichia coli*, but is problematic in that acetic acid is generated as a byproduct and the generation efficiency is not high. The strain KO11 produces ethanol at high levels, into which genes encoding *Zymomonas mobilis*-derived pyruvate decarboxylase and alcohol dehydrogenase have been introduced (FIG. 2). Examples of proteins and enzymes involved in alginate assimilation capacity include proteins involved in incorporation of alginate into a microorganism, enzymes that degrade alginate to generate α-keto acid, and keto acid-metabolizing enzymes that form pyruvic acid from keto acid. Examples of proteins involved in incorporation of alginate into a microorganism include ABC transporter(s) and alginate-binding proteins. Examples of enzymes that degrade alginate to generate α-keto acid include endo-/exo-type alginate lyase. Examples of keto acid-metabolizing enzymes include NADH-dependent α-keto acid reductase (A1-R), kinase (A1-K), and aldolase (A1-A). Genes involved in alginate incorporation and a gene group involved in alginate degradation form clusters in the genome of the *Sphingomonas* sp. strain A1. The ABC transporters form heterotetramers (AlgM1-AlgM2/AlgS-AlgS). The nucleotide sequences of the genes encoding AlgM1, AlgM2, and AlgS are shown in SEQ ID NO: 3, 4, and 5, respectively. Examples of alginate-binding proteins include AlgQ1 and AlgQ2. The nucleotide sequences of the genes encoding AlgQ1 and AlgQ2 are shown in SEQ ID NO: 6 and 7, respectively. Endo-alginate lyase (Aly) contains 3 molecular species of A1-I, A1-II, and A1-III within the molecule. The nucleotide sequence of the gene encoding endo-alginate lyase (Aly) is shown in SEQ ID NO: 8. The nucleotide sequence of the gene encoding exo-type alginate lyase (A1-IV) is shown in SEQ ID NO: 9. The nucleotide sequence of the gene encoding keto acid reductase (A1-R) is shown in SEQ ID NO: 10.

These genes can be introduced using broad-host vectors (IncP, IncQ, and IncW plasmids). Examples of a broad-host vector include plasmid DNA and phage DNA. Specific examples thereof include pKS13, pJRD215, and pUFR027. The genes may be separately inserted into vectors or a plurality of genes may be inserted into one vector. When a plurality of vectors are used, vectors are selected while paying attention on incompatibility among vectors. A method for introducing a recombinant vector into a microorganism is not particularly limited, as long as it is a method for introducing DNA into a microorganism. Examples of such a method include a method using calcium ions [Cohen, S. N. et al.: Proc. Natl. Acad. Sci., U.S.A., 69: 2110 (1972)], an electroporation method, and a tri-parental mating method.

A microorganism in which proteins and enzymes involved in the alginate assimilation capacity of the *Sphingomonas* sp. strain A1 and *Zymomonas mobilis*-derived pyruvate decarboxylase (PDC) and alcohol dehydrogenase (ADH) coexist is cultured in the presence of alginate, so as to cause the microorganism to produce ethanol using alginate as a raw material therewithin. Specifically, the microorganism is cultured under conditions that enable expression of the thus introduced genes encoding the enzymes, and then the enzymes are expressed within the microorganism. Through addition of alginate as a raw material and coenzyme, and then a catalytic reaction of each enzyme takes place and ethanol is generated. At this time, alginate may be added after sufficient expression of the enzymes. Alternatively, when a microorganism containing the genes encoding the enzymes is cultured, alginate and the like are added, so that enzyme expression and enzyme reaction may be performed simultaneously. Also, the amount of alginate decreases with the progress of the enzyme reaction. Hence, additional addition of alginate may be periodically performed.

A method for culturing a microorganism is performed according to a general method to be used for culturing a host. Alginate may be added to a known medium. As alginate to be used as a raw material, alginate such as sodium alginate, potassium alginate, calcium alginate, and ammonium alginate, as well as alginate oligosaccharide, can be used. When sodium alginate is used, it is added to a concentration ranging from 3% to 10% (w/v). When alginate oligosaccharide is used, it is added to a concentration ranging from 5% to 15% (w/v). Also, alginate may be fed over time. Quantitative determination of alginate can be performed by the method described in Knutson, C. A. et al., (1968) Anal. Biochem., 24, 470-481, for example.

Culture and enzyme reaction are generally performed by shaking culture, aeration-agitation culture, or the like under aerobic conditions of 20° C.-40° C., preferably 28° C.-32° C., pH 6.0-pH 9.0, and preferably pH 7.4-pH 8.4 for several hours to several days (e.g., 5 to 7 days). The pH of the medium may be adjusted using inorganic or organic acid, an alkaline solution, or the like. Antibiotics such as kanamycin and penicillin may be added to a medium during culture, if necessary.

Through culture under the above conditions, 0.1%-5% (w/v), and preferably 0.7% or more (w/v) ethanol is accumulated in a medium.

Ethanol can be recovered by distillation. Also, quantitative determination of ethanol can be performed by a known method using alcohol dehydrogenase or a known method using gas chromatography.

Specific culture conditions are as described below, but they are merely examples and are not limited thereto. Culture conditions may be appropriately varied and used by persons skilled in the art.

Culture Conditions (1) Medium composition:
(i) Alginate medium: 3%-10% sodium alginate, 0.1% ammonium sulfate, 0.1% monopotassium phosphate, 0.1% disodium phosphate, 0.01% yeast extract, 0.01% magnesium sulfate 7 hydrate
(ii) Alginate oligosaccharide medium: 5%-15% alginate oligosaccharide, 0.1% ammonium sulfate, 0.1% monopotassium phosphate, 0.1% disodium phosphate, 0.01% yeast extract, 0.01% magnesium sulfate 7 hydrate
(2) pH: pH 6.0-9.0
(3) Culture temperature: 28° C.-37° C.
(4) Shaking frequency: left to stand—100 reciprocations per minute
(5) Culture time: 5 to 7 days
(6) Feeding (to prevent depletion of alginate): On day 3, addition of 1% sodium alginate or alginate oligosaccharide is initiated (once/day)
(7) Concentration of ethanol produced: 0.3%-0.7%
(8) Ethanol recovery: distillation
(9) Optimum conditions for ethanol production (0.7%): medium (3% sodium alginate, 0.1% ammonium sulfate, 0.1% monopotassium phosphate, 0.1% disodium phosphate, 0.01% yeast extract, 0.01% magnesium sulfate 7 hydrate), pH (8.0), temperature (32° C.), shaking frequency (50 reciprocations per minute), culture time (6 days), feeding (on day 3, addition of 1% alginate oligosaccharide is initiated)

A transformed microorganism is immobilized and enzyme reaction is performed, and then ethanol can also be produced. Examples of a method for immobilizing a microorganism include an entrapment method, a crosslinking method, and a carrier binding method. The entrapment method involves entrapping a microorganism within fine lattices of polymer gel or coating with a semipermeable polymer film. The crosslinking method involves crosslinking the microorganism with a reagent (polyfunctional cross-linking agent) having 2 or more functional groups. The carrier binding method involves binding an enzyme to a water-insoluble carrier. Examples of an immobilization carrier to be used for immobilization include glass beads, silica gel, polyurethane, polyacrylamide, polyvinyl alcohol, carrageenan, alginate, agar, and gelatin.

EXAMPLES

Hereafter, the present invention is described in greater detail with reference to the following examples, although the present invention is not limited to these examples.

Example 1

Molecular Breeding (1) of Strain A1 (Bacteria Belonging to the genus *Sphingomonas*)

Materials

As the strain A1 (bacterium belonging to the genus *Sphingomonas* (hereinafter, strain A1)), frozen cells stored as a glycerol stock at the Murata laboratory, Division of Food Science and Biotechnology, Graduate School of Agriculture, Kyoto University were used as starter bacteria. The *Zymomonas mobilis* strain ZM4 (ATCC31821) was purchased from the American Type Culture Collection (ATCC). *Eisenia bicyclis*-derived sodium alginate (average molecular size of 110 kDa; degree of polymerization of up to 650) was purchased from NACALAI TESQUE, INC. Restriction enzymes were purchased from Takara Bio Inc. and Fermentas, and DNA modification enzymes were purchased from Toyobo Co., Ltd. Special grade products were purchased as other compounds from Wako Pure Chemical Industries, Ltd.

Microorganisms and Culture Conditions

Cells of the strain A1 were aerobically cultured in an alginate medium at 30° C. or 32° C. and 100 strokes per minute (spm) (2-cm stroke). The composition of the alginate medium is as follows: 0.1% $(NH_4)_2SO_4$, 0.1% $KH_2PO_4$, 0.1% $Na_2HPO_4$, 0.01% $MgSO_4.7H_2O$, 0.01% yeast extract, and 0.5% or 3% sodium alginate (pH 8.0). Also, 1.5% agar was added if necessary and cells were cultured in a solid medium. For cloning of the gene of pyruvate decarboxylase (PDC) and the gene of alcohol dehydrogenase (ADH), cells of *Z. mobilis* strain ZM4 were aerobically cultured in a medium (pH 6.0) containing 2% glucose, 1% yeast extract, and 0.2% $KH_2PO_4$ at 30° C. and 100 spm for 48 hours. For amplification of plasmids or preparation of helper cells, cells of *Escherichia coli* strain K-12 DH5α or strain HB101 were cultured using a Luria-Bertani (LB) medium (Sambrook et al., 1989) at 37° C. Upon culture, an appropriate antibiotic, ampicillin or tetracycline was added.

DNA Sequencing and DNA Manipulation

The nucleotide sequence of the PDC gene and the nucleotide sequence of the ADH gene were each determined by a dideoxy method using an automatic sequencer (model 377, Applied Biosystems) (Sanger et al., 1977). The genomic DNA of the *Z. mobilis* strain ZM4 was extracted using a DNeasy Blood & Tissue Kit (QIAGEN). Subcloning, transformation, and gel electrophoresis were performed according to the document (Sambrook et al., 1989).

Plasmid Construction

Figure 3:
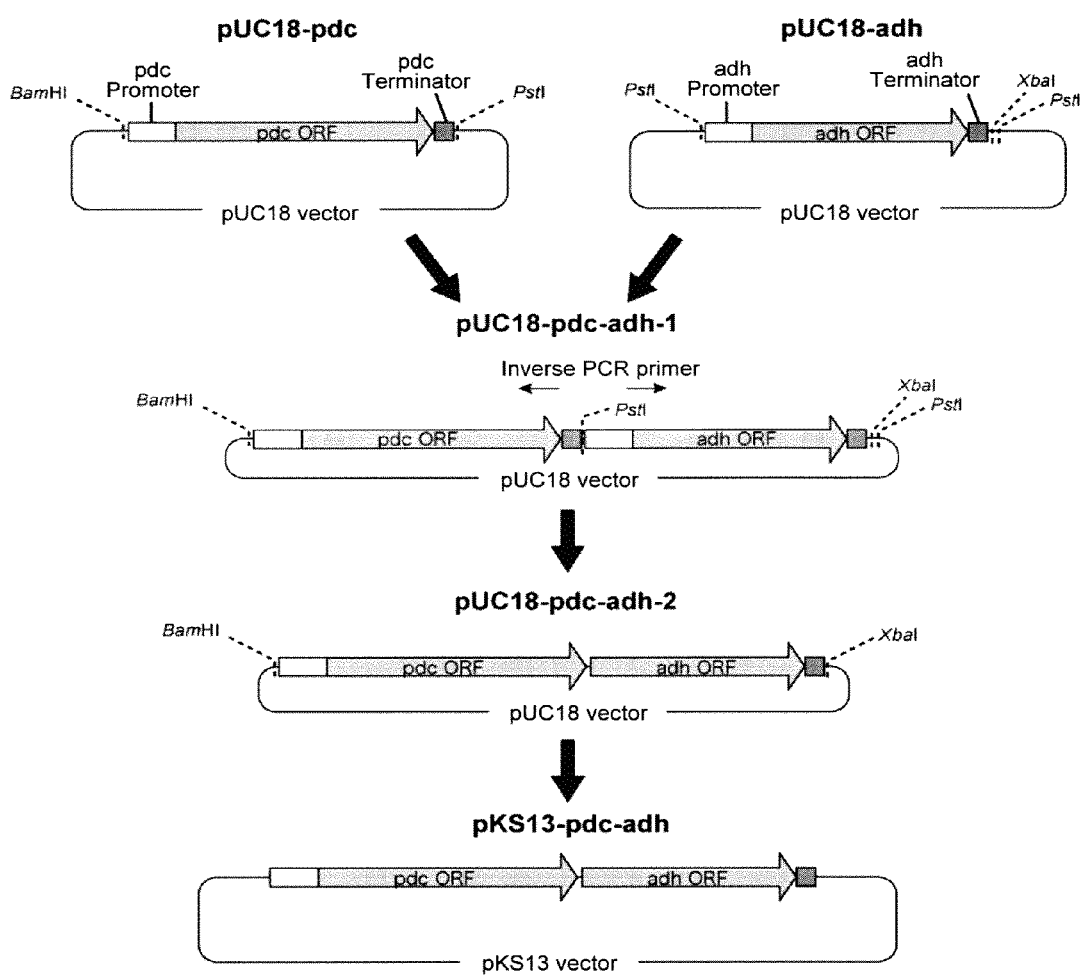
FIG. 3 shows schematic diagrams of plasmids for introduction of genes encoding pyruvate decarboxylase (PDC) and alcohol dehydrogenase (ADH) into the strain A1.

For separately introducing the gene of PDC and the gene of ADH into the strain A1, both genes were amplified by polymerase chain reaction (PCR). PCR was performed using KOD-Plus polymerase (Toyobo Co., Ltd.), the genomic DNA of the *Z. mobilis* strain ZM4 as a template, and 2 types of synthetic oligonucleotide as primers. For amplification of the PDC gene, 5'-GAGGATCCTCACTTAATCCAGAAACGGGCG-3' (SEQ ID NO: 11) containing a BamH I site (underlined) and 5'-GACTGCAGACGGGCTTTTCGCCTTAAGC-3' (SEQ ID NO: 12) containing a Pst I site (underlined) were used as primers. The gene fragment amplified by PCR was treated with BamH I/Pst I restriction enzymes and then subcloned into a pUC18 vector treated with BamH I/Pst I (pUC18-pdc plasmid). For amplification of the ADH gene, 5'-GACTGCAGAAAGGCAAAATCGGTAACCACATCTC-3' (SEQ ID NO: 13) containing a Pst I site (underlined) and 5'-GGTCTAGATTATGACGGTAGGCTTAATAGCCTG-3' (SEQ ID NO: 14) containing an Xba I site (underlined) were used as primers. The gene fragment amplified by PCR was subcloned into a pUC18 vector treated with Hinc II restriction enzyme and then with alkaline phosphatase (pUC18-adh plasmid). A gene fragment containing ADH was excised by treatment with Pst I from the pUC18-adh plasmid and then ligated to a pUC 18-pdc plasmid treated with Pst I and alkaline phosphatase (pUC18-pdc-adh-1). Subsequently, a PDC gene terminator and an ADH gene promoter were removed by inverse PCR (pUC18-pdc-adh-2). Inverse PCR was performed using pUC18-pdc-adh-1 as a template, and 5'-CCGGAATTCTTACTAGAGGAGCTTGTTAACAGGCTTACG-3' (SEQ ID NO: 15) and 5'-ACTAGTATGTAGGGTGAGGTTATAGCTATGGCT-3' (SEQ ID NO: 16) as primers. The nucleotide sequences of the PDC gene and the ADH gene in pUC18-pdc-adh-2 were confirmed by DNA sequencing. After cleavage of pUC18-pdc-adh-2 with BamH I and Xba I, a fragment containing the PDC gene and the ADH gene was ligated to a broad-host vector pKS 13 (having a tetracycline resistance marker: Kimbara et al., 1989) treated with BamH I and Xba I. The thus finally constructed plasmid (pKS13-pdc-adh) was designed so that both PDC and ADH genes were transcribed by the promoter of the PDC gene (FIG. 3). Also, various plasmids were constructed for comparison and examination.

Tri-Parental Mating

The pKS13-pdc-adh plasmid was introduced into the strain A1 by a tri-parental mating (conjugal transfer) method (Ruvkun & Ausubel, 1981). The strain A1, *Escherichia coli* DH5α/pKS13-pdc-adh, and *Escherichia coli* HB101/pRK2013 (helper cells) were separately cultured to the logarithmic growth phase, 3 types of microorganism were mixed, and then cells were cultured overnight in an alginate agar medium containing a 0.5% yeast extract. Subsequently, cells were cultured in an alginate agar medium containing 20 µg/mL tetracycline, a tetracycline-resistant transformant was obtained, and thus the introduction of the PDC gene and the ADH gene was confirmed by PCR. The thus obtained transformant was designated as a strain A1 (strain EPv2) into which the genes had been introduced.

Measurement of Enzyme Activity and Protein Concentration

The activity of PDC and ADH in the strain A1 into which the genes had been introduced was measured according to the documents (Conway et al., 1987a and Conway et al., 1987b). (Preparation of crude enzyme solution) A wild-type strain A1 and the strain EPv2 were separately cultured using a 3% alginate medium at 50 rpm and 32° C. for 3 days. Cells collected by 5 minutes of centrifugation at 6,000×g and 4° C. were washed with 50 mM sodium phosphate buffer (pH 6.5) and then suspended again with the same buffer. Cells were disrupted by ultrasonication using an ultrasonic generator (model 201M, Kubota) under conditions of 0° C. and 9 kHz for 10 minutes. Subsequently, a supernatant obtained by 5 minutes of centrifugation at 15,000×g and 4° C. was designated as a crude enzyme solution. The crude enzyme solution was subjected to protein quantification by the method of Bradford (Bradford, 1976) using bovine serum albumin as a standard protein. The solution was diluted with 50 mM sodium phosphate buffer, so that the protein concentration ranged from 0.5 mg/mL to 2 mg/mL.

(PDC activity measurement) PDC activity was evaluated by measuring changes (in absorbance at a wavelength of 340 nm) associated with decreases in NADH. The amount of enzyme that results in decreases of 1 μmol NADH per minute at 30° C. was defined as 1 unit (U). Specifically, measurement was performed as follows. 100 mM Tris-maleate buffer (pH 6.0) (457 μL), 20 μL of 300 mM sodium pyruvate, 1 μL of 0.4 U ADH (Roche), 2 μL of 60 mM NADH.2Na, and 20 μL of the crude enzyme solution were mixed in a cuvette immediately before measurement, a decrease in absorbance at 340 nm ($\Delta 340$) was measured using an absorptiometer (MPS-2000, Shimadzu), and then specific activity was calculated with the following formula.

PDC specific activity (U/mg protein)=Δ340×total volume of reaction solution (mL)÷[protein concentration (mg/mL) in the enzyme solution×the volume of the enzyme solution (mL)×6.22×optical length (cm)

Here, "$\Delta 340$" denotes the amount of a decrease in absorbance at 340 nm per minute and "6.22" is the mmol molecular extinction coefficient of NADH.

(ADH activity measurement) ADH activity was evaluated by measuring changes in absorbance at a wavelength of 340 nm involved with decreases in NADH. The amount of the enzyme that decreases 1 μmol NADH per minute at 30° C. was defined as 1 unit (U). Specifically, measurement was performed as follows. 100-mM Tris-maleate buffer (pH 6.5) (457 μL), 10 μL of 500 mM acetaldehyde, 2 μL of 60 mM NADH.2Na, and 20 μL of the crude enzyme solution were mixed in a cuvette immediately before measurement, a decrease ($\Delta 340$) in absorbance at 340 nm was measured using an absorptiometer (MPS-2000, Shimadzu), and then specific activity was calculated by the following calculating formula.

ADH specific activity (U/mg protein)=Δ340×total volume of reaction solution (mL)÷protein concentration (mg/mL) in enzyme solution×volume of enzyme solution (mL)×6.22×optical length (cm)

Here, "$\Delta 340$" denotes the amount of a decrease in absorbance at 340 nm per minute and "6.22" is the mmol molecular extinction coefficient of NADH.

Figure 4:
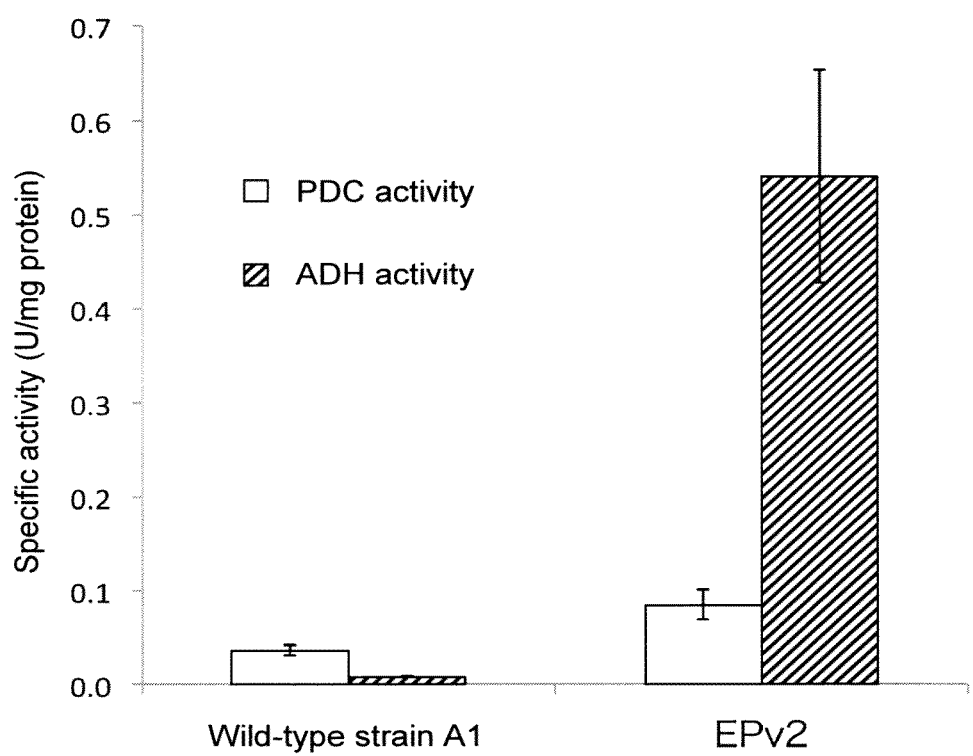
FIG. 4 shows pyruvate decarboxylase (PDC) activity and alcohol dehydrogenase (ADH) activity of cell extracts from a wild-type strain A1 and the strain A1 (strain EPv2) into which the genes were introduced.

(Results) PDC activity and ADH activity contained in the cell extracts of the wild-type strain A1 and the strain EPv2 were measured (FIG. 4). As a result, the strain EPv2 was found to exhibit twice the PDC activity and 70 times the ADH activity of the wild-type strain A1. The strain EPv2 was subjected to an ethanol production test (Example 2).

REFERENCES IN THIS EXAMPLE

Bradford, M. M. (1976) Anal. Biochem., 72, 248-254.
Conway, T., Osman, Y. O., Konnan, J. I., Hoffmann, E. M., and Ingram, L. O. (1987a) Promoter and nucleotide sequences of the *Zymomonas mobilis* pyruvate decarboxylase. J. Bacteriol., 169, 949-954.
Conway, T., Sewell, G. W., Osman, Y. O., and Ingram, L. O. (1987b) Cloning and sequencing of the alcohol dehydrogenase II gene from *Zymomonas mobilis*. J. Bacteriol., 169, 2591-2597.
Kimbara, K., Hashimoto, T., Fukuda, M., Koana, T., Takagi, M., Oishi, M., and Yano, K. (1989) J. Bacteriol., 171, 2740-2747.
Ruvkun, G. B., and Ausubel, F. M. (1981) Nature, 289, 85-88.

Sambrook, J., Fritsch, E. F., and Maniatis, T. (1989) Molecular cloning: a laboratory manual, 2nd ed., Cold Spring Harbor Laboratory Press, Cold Spring Harbor, N.Y.
Sanger, F., Nicklen, S., and Coulson, A. R. (1977) Proc. Natl. Acad. Sci. U.S.A., 74, 5463-5467.

Example 2

Ethanol Production by Strain A1 (Bacteria Belonging to the Genus *Sphingomonas*)

Materials

*Eisenia bicyclis*-derived sodium alginate (average molecular size of 110 kDa; degree of polymerization of up to 650) was purchased from NACALAI TESQUE, INC. For ethanol quantification by an enzyme method, an F-kit (ethanol) was purchased from Roche Diagnostics. Special grade products were purchased as other compounds from Wako Pure Chemical Industries, Ltd.

Preparation of Alginate Oligosaccharide

An *Escherichia coli* strain (HMS174 (DE3) pLysS/pET3a-A1-III) expressing strain A1 (of bacteria belonging to the genus *Sphingomonas*)-derived endo-alginate lyase A1-III at high levels (Yoon et al., 2000) was pre-cultured using a Luria-Bertani (LB) medium (Sambrook et al., 1989) containing ampicillin (0.1 mg/mL) at 30° C. and 100 rpm. Subsequently, when turbidity at 600 nm was 0.5, isopropyl-β-D-thiogalactopyranoside was added to the medium to a final concentration of 0.1 mM, and then cells were further cultured for 48 hours at 16° C. and 100 rpm. *Escherichia coli* cells collected by 5 minutes of centrifugation at 6,000×g and 4° C., washed with 20 mM potassium phosphate buffer (pH 7.0), and then suspended again with the same buffer. Cells were disrupted by ultrasonication using an ultrasonic generator (model 201M, Kubota) under conditions of 0° C. and 9 kHz for 20 minutes. Subsequently, a supernatant obtained by 20 minutes of centrifugation at 15,000×g and 4° C. was designated as a cell extract. The cell extract was added to 3% sodium alginate, so that alginate was degraded until the viscosity decreased. Then, ethanol was added in an amount twice the amount of the solution. Undegraded or macromolecular alginate was subjected to 20 minutes of centrifugation at 15,000×g and 4° C., so as to remove the precipitate. The supernatant containing alginate oligosaccharide (disaccharide and trisaccharide were major ingredients) was evaporated to dryness using a rotary evaporator (model N-1000, Tokyo Rikakikai Co., Ltd.).

Alginate Quantification

Alginate concentration in a medium was determined by a sulfuric acid-carbazole method (Knutson & Jeanes, 1968).

Ethanol Quantification

Ethanol concentration in the culture solution of cells of the gene-transferred strain A1 was measured by an enzyme method or a head-space gas chromatography method. Values with good reproducibility were obtained with good sensitivity by both methods. With the enzyme method, ethanol existing in a sample is converted to acetic acid with alcohol dehydrogenase and aldehyde dehydrogenase and NADH generated by this process is quantitatively determined from absorbance at a wavelength of 340 nm, so that the amount of ethanol in the sample can be estimated. A calibration curve was produced using an F kit (ethanol) based on this principle and then ethanol in a sample was quantitatively determined. The head-space gas chromatography method was performed as follows. A glass vial with septum (7 mL) was filled with 50 μL of a sample, 100 μL of internal standard (0.2% n-propanol), and 900 μL of pure water and then left to stand at 55°

C. for 20 minutes. Subsequently, 1 mL of the gas phase in the vial containing evaporated alcohol was injected to a gas chromatograph using a gas-tight syringe. GC-2014 (Shimadzu) was used as the gas chromatograph. Rtx (trademark)-Wax (30 m, inner diameter of 0.53 mm, Restec) was used as the column. Nitrogen gas was used as carrier gas (column flow: 4.16 mL/min). The injection mode for a sample employed herein was "split." The column temperature was set so that the temperature was 40° C. after injection of a sample, maintained for 5 minutes, increased at 10° C./min, and then maintained at 100° C. for 1 minute. FID was used as a detector. The peak area of ethanol and the same of internal standard were found, the ratio of ethanol to internal standard was calculated, and then ethanol in the sample was quantitatively determined based on the calibration curve.

Microorganisms and Culture Conditions

Cells of the strain EPv2 bred in Example 1 were cultured in an alginate medium. The composition of the alginate medium is as follows: 0.1% $(NH_4)_2SO_4$, 0.1% $KH_2PO_4$, 0.1% $Na_2HPO_4$, 0.01% $MgSO_4 \cdot 7H_2O$, 0.01% yeast extract, and 0.5% to 3% sodium alginate. Various culture conditions (e.g., the degree of polymerization of alginate (polymer or oligosaccharide), alginate concentration, the ratio of liquid volume to vessel capacity, temperature, shaking frequency, and pH) were examined. Conditions with which high-level growth and high-level ethanol production can be achieved were determined as follows. The degree of polymerization of alginate: polymer; and alginate concentration: 3%; the ratio of liquid volume to vessel capacity: 100 mL/300 mL; temperature: 32° C.; shaking frequency: 50 spm (2-cm stroke); and pH: 7.4 to 8.4.

Ethanol Production

Figure 5A:
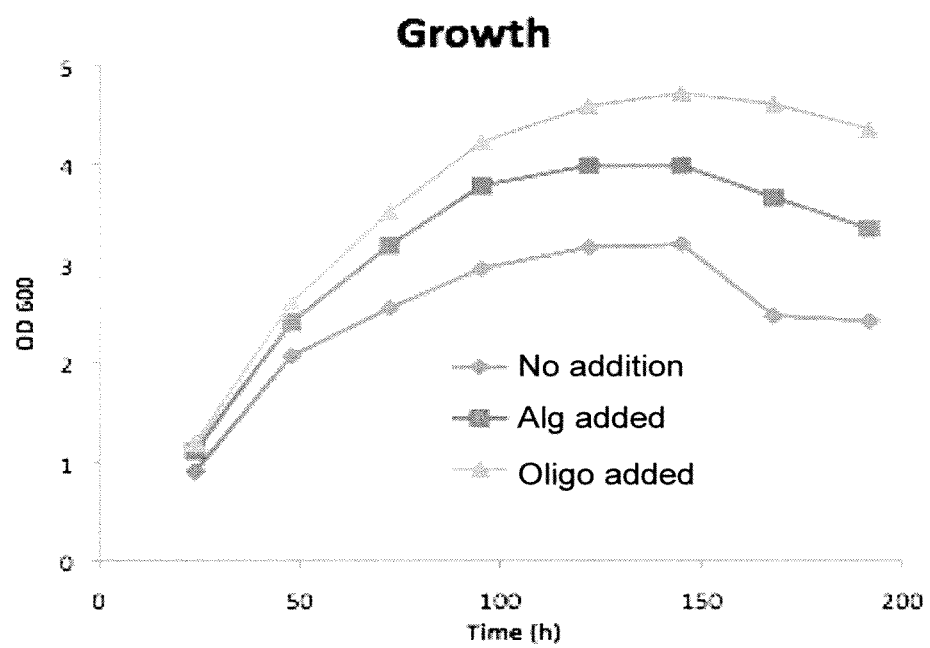
FIG. 5A shows the growth of the strain EPv2.
Figure 5B:
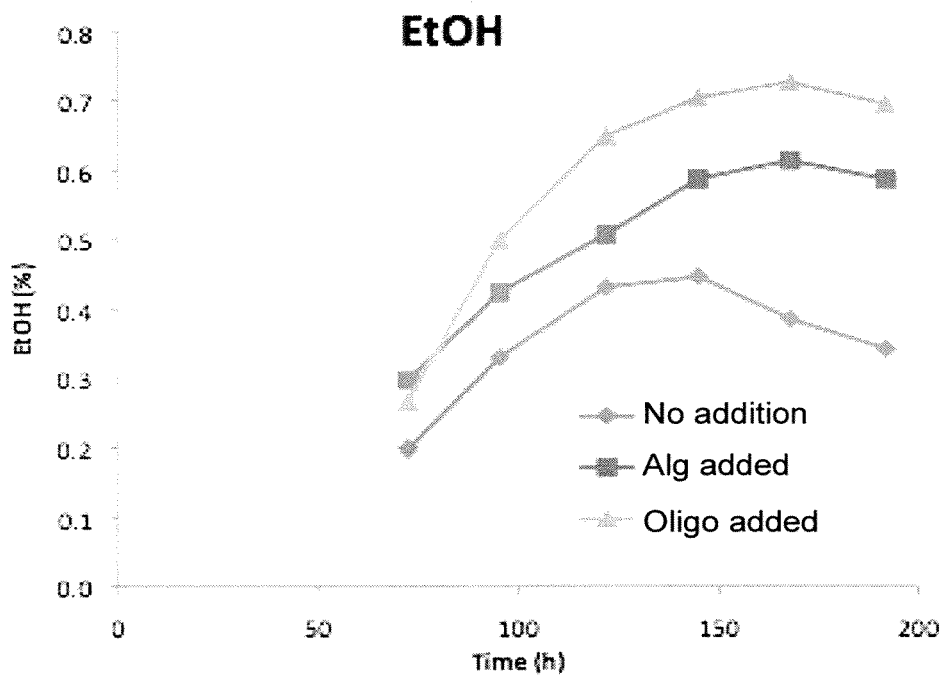
FIG. 5B shows ethanol (EtOH) production by the strain EPv2.
Figure 5C:
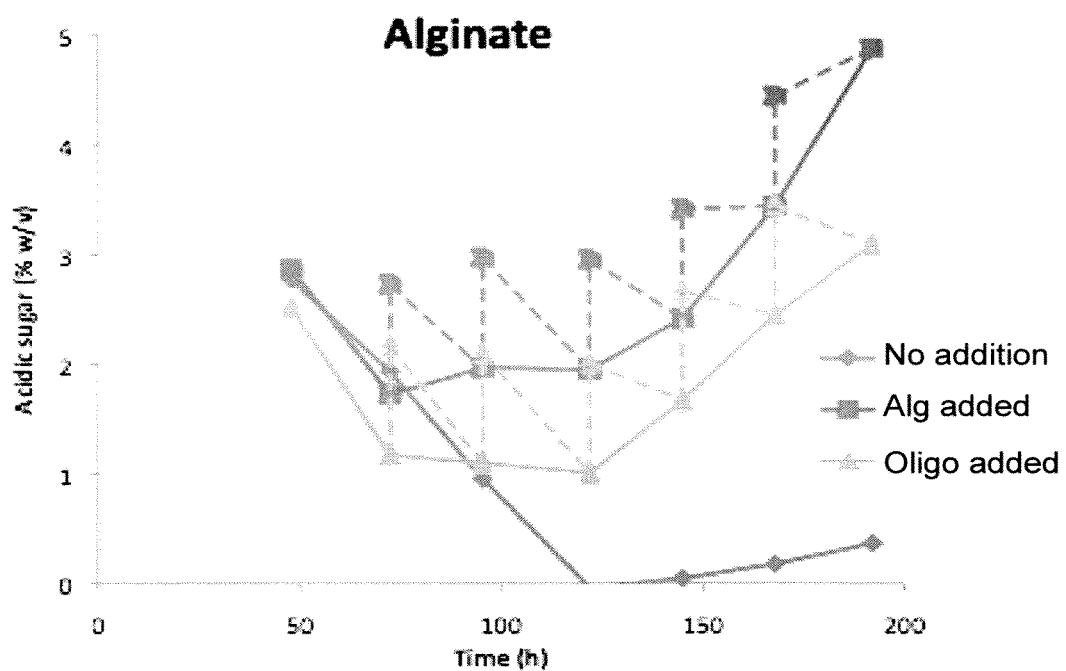
FIG. 5C shows alginate consumption by the strain EPv2.

When the wild-type strain A1 was cultured in an alginate medium, the culture solution contained only 0.003% to 0.005% ethanol. Meanwhile, when cells of the strain EPv2 were cultured under the above optimum conditions, ethanol accumulation took place to result in 0.45% ethanol in the medium within 140 hours of culture (FIG. 5B, no addition). At this time, alginate consumption in the medium began to increase at about hour 48 of culture, and alginate in the medium decreased at a rate of about 1%/day (FIG. 5C, no addition). Subsequently, alginate in the medium was almost depleted at around hour 120 of culture. This depletion of alginate was thought to be a factor determining the rate of ethanol production. Thus, the addition of alginate was attempted during culture. At or after hour 72 of culture, 1 g (powder) of alginate or alginate oligosaccharide was added once a day to the medium. Growth was found to improve with this addition (FIG. 5A), but the peak time of the growth curve did not change depending on the presence or the absence of the addition (hour 140). Regarding ethanol production (FIG. 5B), whereas ethanol production reached a maximum level between hour 120 and hour 140 of culture and then decreased in a sample to which no control had been added, ethanol accumulation was continued (up to 0.6%) to about hour 170 of culture when alginate had been added. With the addition of alginate oligosaccharide, the ethanol generation rate increased (during hour 72 to hour 120) compared with a case in which alginate was added, and the ethanol concentration reached its maximum level at hour 170 (0.72%). The amount of alginate in the medium was measured. The amount of alginate decreased at a rate of 1%/day until hour 120 when alginate (oligo) was added. However, alginate was slowly consumed from about hour 120 to hour 140, and almost no alginate was consumed at or after hour 140 (FIG. 5C).

REFERENCES OF THIS EXAMPLE

Knutson, C. A., and Jeanes, A. (1968) Anal. Biochem., 24, 470-481.

Sambrook, J., Fritsch, E. F., and Maniatis, T. (1989) Molecular cloning: a laboratory manual, 2nd ed., Cold Spring Harbor Laboratory Press, Cold Spring Harbor, N.Y.

Yoon, H.-J., Hashimoto, W., Miyake, O., Okamoto, M., Mikami, B., and Murata, K. 2000. Protein Expr. Purif., 19, 84-90.

Example 3

Strain A1 (Bacteria Belonging to the genus *Sphingomonas*) Becoming Resistant (Developing Tolerance) to Ethanol Materials For the strain A1 (hereinafter, the strain A1) of bacteria belonging to the genus *Sphingomonas*, frozen cells stored in the form of glycerol stock at the Murata laboratory, Division of Food Science and Biotechnology, Graduate School of Agriculture, Kyoto University, were used as starter bacteria. *Eisenia bicyclis*-derived sodium alginate (average molecular size of 110 kDa; degree of polymerization of up to 650) was purchased from NACALAI TESQUE, INC. Special grade products were purchased as other compounds from Wako Pure Chemical Industries, Ltd.

Microorganisms and Culture Conditions

Cells of the strain A1 were aerobically cultured in an alginate medium at 30° C. and 100 spm for 48 hours. The composition of the alginate medium is as follows: 0.1% $(NH_4)_2SO_4$, 0.1% $KH_2PO_4$, 0.1% $Na_2HPO_4$, 0.01% $MgSO_4 \cdot 7H_2O$, 0.01% yeast extract, and 0.5% sodium alginate (pH 7.2). Also, ethanol was added, if necessary.

Development of Tolerance to Ethanol

Figure 6:
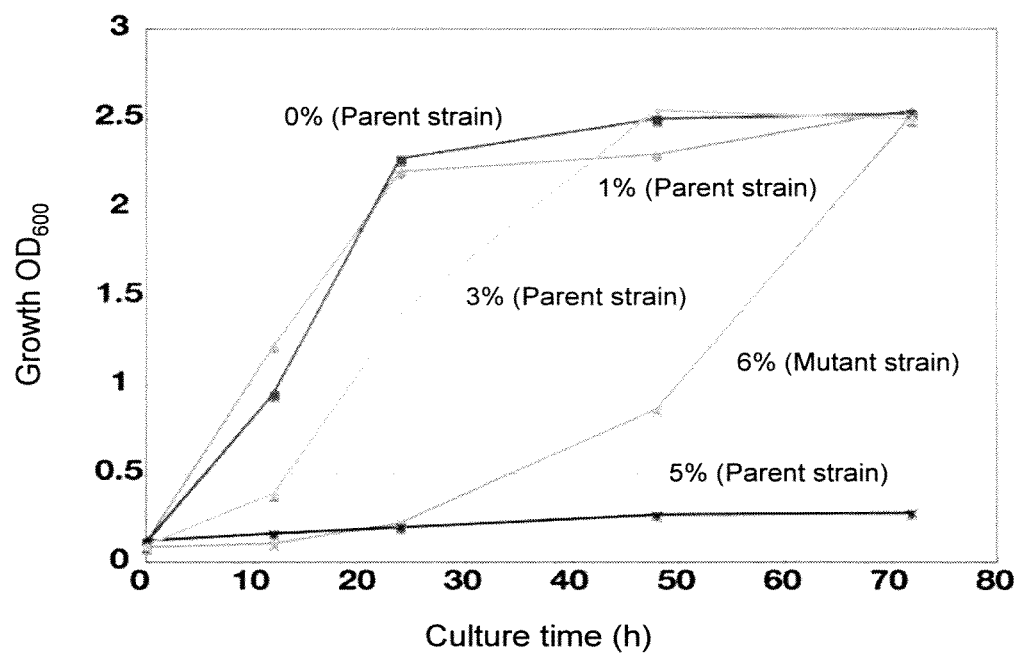
FIG. 6 shows the acquisition of ethanol resistance by the strain A1.

The wild-type strain A1 was cultured in an alginate medium containing ethanol (1% to 5%) and growth was evaluated based on turbidity at a wavelength of 600 nm (FIG. 6). As a result, growth was not inhibited with 1% ethanol. However, the wild type strain A1 exhibited significantly delayed growth with 3% ethanol, and did not grow at all with 5% ethanol. To breed a strain A1 that enables high ethanol production, a strain A1 was treated to develop tolerance to ethanol. The strain A1 was acclimatized at an ethanol concentration of 4% or greater. Also, ultraviolet irradiation (15 seconds) was performed in a timely manner, thereby inducing random mutation. A strain A1 capable of growing even in the presence of 6% ethanol was previously bred through a combination of acclimatization and mutation (FIG. 6).

Example 4

Preparation of Alginate Oligosaccharide Using Immobilized Cells

Materials

*Eisenia bicyclis*-derived sodium alginate (average molecular size of 110 kDa; degree of polymerization of up to 650) was purchased from NACALAI TESQUE, INC. Special grade products were purchased as other compounds from Wako Pure Chemical Industries, Ltd.

Microorganisms and Culture Conditions

An *Escherichia coli* strain (HMS174(DE3)pLysS/pET3a-A1-III) (Yoon et al., 2000) expressing the strain A1 (bacteria of the genus *Sphingomonas*)-derived endo-alginate lyase A1-III at a high level was pre-cultured in a Luria-Bertani (LB) medium containing ampicillin (0.1 mg/mL) (Sambrook et al., 1989) at 30° C. and 100 rpm. Subsequently, when turbidity at 600 nm was 0.5, isopropyl-β-D-thiogalactopyranoside was added to the medium to a final concentration of 0.1 mM, followed by 48 hours of culture at 16° C. and 100 rpm. *Escherichia coli* cells (9 g) collected by 5 minutes of centrifugation at 6,000×g and 4° C. were washed with 20 mM Tris-HCl buffer (pH 7.5) and then suspended again in 12 mL of the same buffer.

Preparation of Immobilized Cells

The *Escherichia coli* suspension was transferred to a 200-mL beaker. Tetramethylethylenediamine (24 µL) was added to an acrylamide solution (3 g of acrylamide, 54 mg of bisacrylamide, 100 µL of aqueous 25% ammonium persulfate solution were mixed and adjusted with distilled water to 9 mL) and then the solution was immediately added to the *Escherichia coli* solution. Polymerization was performed on ice. After polymerization (immobilization of cells), the resultant was washed twice with 100 mL of 5 mM Tris-HCl buffer (pH 7.5). Immobilized cells were cut into about 5-mm dice, 100 mL of acetone was added to the immobilized cells on ice, and then the resultant was gently mixed for 5 minutes. Immobilized cells were washed 3 times with 100 mL of 5 mM Tris-HCl buffer (pH 7.5) and then stored at 4° C. in the same buffer.

Preparation of Alginate Oligosaccharide

Figure 7:
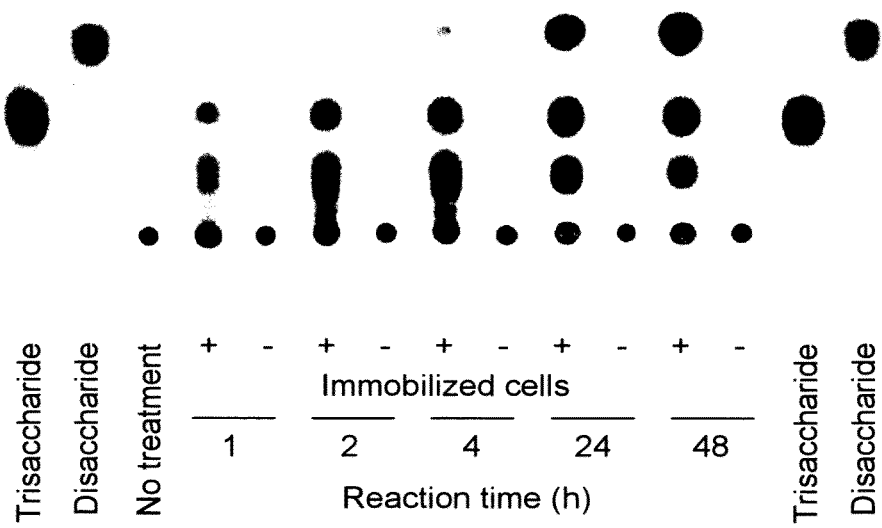
FIG. 7 shows alginate degradation by immobilized cells.

Immobilized cells (170 mg to 200 mg) were added to 2.0 mL of an alginate solution (3% sodium alginate, 50 mM potassium phosphate buffer (pH 7.0)). Incubation was performed for 1 to 48 hours while slowly shaking (50 spm) at 30° C. Within about 2 hours after addition of immobilized cells, the viscosity of the alginate solution decreased. After the reaction, immobilized cells were collected. A portion of the reaction solution was developed with thin-layer chromatography TLC (Hashimoto et al., 2000) (FIG. 7). One hour after the initiation of the reaction, oligosaccharides (trisaccharides or greater) and some disaccharides were confirmed. The amounts of disaccharides and trisaccharides increased with time. Cold ethanol was added to the reaction solution to a concentration of 75%, polysaccharides and oligosaccharides were fractionated, and then the amount of acidic sugar of each fraction was measured (Table 1). At or after hour 2 of reaction, about ⅓ of the alginate exhibited a lower molecular weight. It was revealed based on the above results that immobilized *Escherichia coli* cells expressing A1-III degrade alginate, and thus alginate oligosaccharides can be prepared.

TABLE 1

| Immobilized cells | Amount of acidic sugar (mg) | | | |
|---|---|---|---|---|
| | + | | − | |
| 75% EtOH | Soluble | Precipitated | Soluble | Precipitated |
| No treatment | | | n.d. | 55.7 |
| Time for treatment (h) 1 | 3.0 | 45.5 | n.d. | 48.5 |
| 2 | 16.4 | 37.5 | n.d. | 52.7 |
| 4 | 13.5 | 35.1 | 0.1 | 53.4 |
| 24 | 17.9 | 48.3 | n.d. | 48.8 |
| 48 | 17.6 | 47.6 | n.d. | 62.8 |

Yield of Alginate Lyase Activity

Total enzyme activity and activity yield of alginate lyase in immobilized cells were evaluated. Immobilized cells (500 mg) were added to 5 mL of 20 mM Tris-HCl buffer (pH 7.5) and then disrupted with a Dounce homogenizer in the form of slurry. For comparison, 9 g of *Escherichia coli* cells that were the same as those used in preparation of immobilized cells was suspended in 50 mM sodium phosphate buffer (pH 6.5) and then disrupted by ultrasonication using an ultrasonic generator (model 201M, Kubota) under conditions of 0° C. and 9 kHz for 10 minutes. Subsequently, a supernatant obtained by 5 minutes of centrifugation at 15,000×g and 4° C. was collected and then adjusted with 20 mM Tris-HCl buffer (pH 7.5) to 50 mL, so that a crude enzyme solution was prepared. Alginate lyase activity was measured according to the document (Yoon et al., 2000). The reaction solution (500 µL) was prepared, containing 0.05% sodium alginate, 100 mM potassium phosphate buffer (pH 7.0), and 10 µL of an immobilized cell slurry or a crude enzyme solution. The increase in absorbance at a wavelength of 235 nm was measured. Enzyme activity resulting in an increase of absorbance at a wavelength of 235 nm by 1 per minute was designated as "1 U." As a result, the total enzyme activity of alginate lyase in immobilized cells was 1,950 U, while the total enzyme activity of the same in a crude enzyme solution (prepared by disruption of the same amount of *Escherichia coli* cells by ultrasonication) was 5,600 U. Based on the above results, the immobilization efficiency of alginate lyase activity in the preparation of immobilized cells was estimated to be about 35%.

REFERENCES IN THIS EXAMPLE

Hashimoto, W., Miyake, O., Momma, K., Kawai, S., and Murata, K.
Sambrook, J., Fritsch, E. F., and Maniatis, T. (1989) Molecular cloning: a laboratory manual, 2nd ed., Cold Spring Harbor Laboratory Press, Cold Spring Harbor, N.Y.
Yoon, H.-J., Hashimoto, W., Miyake, O., Okamoto, M., Mikami, B., and Murata, K. 2000. Protein Expr. Purif., 19, 84-90.

Example 5

Molecular Breeding of *Escherichia coli* strain KO11
Materials

An *Escherichia coli* strain KO11 (hereinafter, strain KO11) (ATCC 55124) was purchased from the American Type Culture Collection (ATCC). *Eisenia bicyclis*-derived sodium alginate (average molecular size of 110 kDa and the degree of polymerization of up to 650) was purchased from NACALAI TESQUE, INC. Restriction enzymes were purchased from Takara Bio Inc. and DNA modification enzymes were purchased from Toyobo Co., Ltd. Special grade products as other compounds were purchased from Wako Pure Chemical Industries, Ltd.

Microorganisms and Culture Conditions

A gene cluster involved in incorporation and degradation of the strain A1 (of bacteria belonging to the genus *Sphingomonas* (hereinafter, strain A1))-derived alginate was cloned into a broad-host vector (pKS13) (plasmid pBE11) (FIG. 8) (Momma et al., 2000). For plasmid amplification, cells of the *E. coli* strain K-12 DH5α were cultured using a Luria-Bertani (LB) medium (Sambrook et al., 1989) at 37° C. Upon culture, appropriate antibiotic, ampicillin or tetracycline was added. For plasmid transfer (transformation), the strain KO11 was aerobically cultured in a LB medium containing glucose at 37° C., and thus competent cells were prepared by a calcium chloride method (Sambrook et al., 1989).

DNA Sequencing and DNA Manipulation

Figure 8:
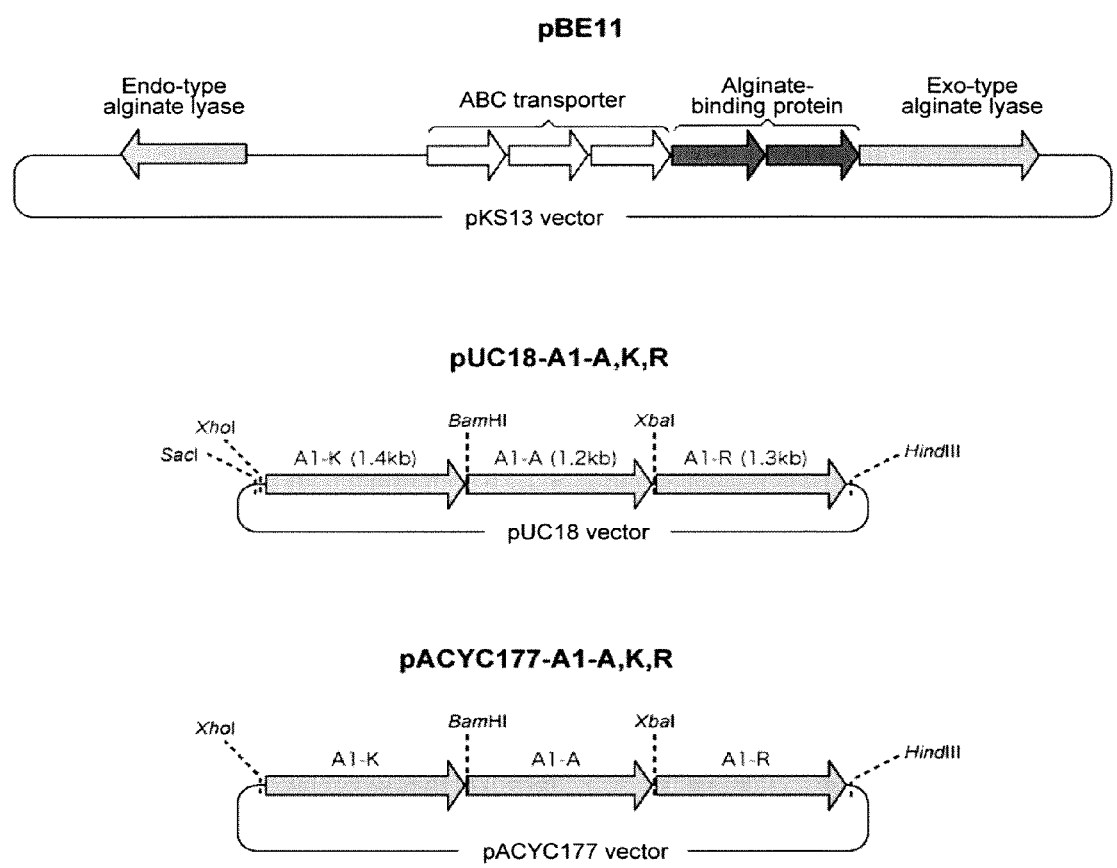
FIG. 8 shows schematic diagrams of plasmids for introduction of genes encoding A1-R, A1-K, and A1-A into a strain KO11.

The strain A1 metabolizes alginate monosaccharide (α-keto acid) by consecutive reaction with reductase (A1-R), kinase (A1-K), and aldolase (A1-A). Each nucleotide sequence of the enzyme (A1-R, A1-K, and A1-A) genes was determined by a dideoxy method using an automatic sequencer (model 377, Applied Biosystems) (Sanger et al., 1977). Extraction of the genomic DNA of the strain A1, subcloning, transformation, and gel electrophoresis were performed according to the document (Sambrook et al., 1989).
Plasmid Construction For introduction of A1-R, A1-K, and A1-A genes into the strain KO11, each gene was amplified by polymerase chain reaction (PCR) using KOD-Plus polymerase (Toyobo Co., Ltd.), the genomic DNA of the strain A1 as a template, and 2 types of synthetic oligonucleotide as primers. For amplification of the A1-R gene, 5'-AACC TCTAGACCGTGATGCTGGGTGACGACCACGCTG-3' (SEQ ID NO: 17) having an Xba I site (underlined) and 5'-AACC AAGCTTCGGCGCTGATTCGGGGCGAATGTTCGTC-3' (SEQ ID NO: 18) having a Hind III site (underlined) were used as primers. For amplification of the A1-K gene, 5'-AACC GAGCTCGAGGGAACCGCAGCGGCGGATCGTGTCG-3' (SEQ ID NO: 19) having a Sac I site and an Xho I site (underlined) and 5'-AACC GGATCCGCGCCTATTGTCAGAAGGCGCCGACCTC-3' (SEQ ID NO: 20) having a BamH I site (underlined) were used as primers. For amplification of the A1-A gene, 5'-TTGC GGATCCGCAGCTCGAAAAGGCTTCCTCGATCG-3' (SEQ ID NO: 21) having a BamH I site (underlined) and 5'-TTGC TCTAGACCCACACCTGGAAGGTGCGGGTGTTGC-3' (SEQ ID NO: 22) having an Xba I site (underlined) were used as primers. The A1-K gene fragment amplified by PCR was treated with BamH I/Sac I restriction enzymes and then subcloned into a pUC18 vector treated with BamH I/Sac I (pUC18-A1-K plasmid). Subsequently, the A1-K gene fragment amplified by PCR was treated with Hind III/Xba I restriction enzymes and then subcloned into the pUC18-A1-K plasmid treated with Hind III/Xba I (pUC18-A1-K, R plasmid). Furthermore, the A1-A gene fragment amplified by PCR was treated with BamH I/Xba I restriction enzymes and then subcloned into the pUC18-A1-K, R plasmid treated with BamH I/Xba I (pUC18-A1-A, K, R plasmid). Finally, the pUC18-A1-A, K, R plasmid was treated with Hind III/Xho I restriction enzymes and then a fragment containing the A1-R, A1-K, and A1-A genes was subcloned into a pACYC177 vector treated with Hind III/Xho I. The thus constructed plasmid was designated as pACYC177-A1-A, K, R (FIG. 8). The strain KO11 was transformed with pBE11 and pACYC177-A1-A, K, R. The transformed strain was designated as a strain KO11 into which the genes had been introduced. Gene introduction was confirmed by amplification of target genes by colony PCR.

Measurement of Enzyme Activity and Protein Concentration

The alginate-degrading (lyase) activity of the strain KO11 into which the genes had been introduced was confirmed by TLC.

(Preparation of crude enzyme solution) The strain KO11 into which the genes had been introduced was cultured using an LB medium containing 0.5% sodium alginate at 100 spm and 37° C. for 1 day. Cells collected by 5 minutes of centrifugation at 6,000×g and 4° C. were washed with 50 mM potassium phosphate buffer (pH 7.0) and then suspended again in the same buffer. Cells were disrupted by ultrasonication using an ultrasonic generator (model 201M, Kubota) under conditions of 0° C. and 9 kHz for 10 minutes. Subsequently, a supernatant obtained by 5 minutes of centrifugation at 15,000×g and 4° C. was designated as a crude enzyme solution. The crude enzyme solution was subjected to protein quantification using the method of Bradford (Bradford, 1976) using bovine serum albumin as a standard protein. The solution was diluted with 50 mM potassium phosphate buffer (pH 7.0) so that a protein concentration ranged from 0.5 to 2 mg/mL.

Figure 9:
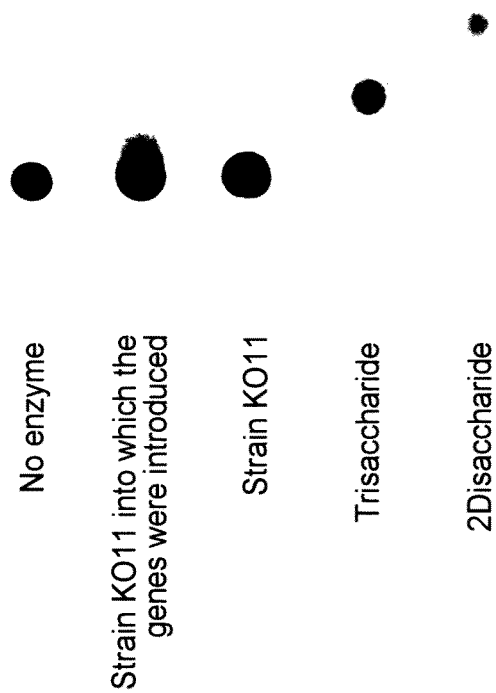
FIG. 9 shows the alginate lyase activity of the strain KO11 into which the genes were introduced.

(Alginate-degrading activity) The alginate-degrading activity of the strain KO11 into which the genes had been introduced contained in the cell extract was measured. In addition, a strain KO11 into which no gene had been introduced was used as a control strain. Each cell extract (10 µL) was added to an alginate solution (0.5% sodium alginate: 10 µL), followed by overnight reaction at 30° C. A portion of the reaction solution was developed with thin-layer chromatography TLC, and then a degraded alginate product was detected (Hashimoto et al., 2000). Alginate-degrading activity was not observed in the control strain, but lower molecular weights of alginate were observed in the strain KO11 into which the genes had been introduced, suggesting the expression of alginate lyase (FIG. 9).

REFERENCES IN THIS EXAMPLE

Bradford, M. M. (1976) Anal. Biochem., 72, 248-254.
Momma, K., Okamoto, M., Mishima, Y., Mori, S., Hashimoto, W., and Murata, K. (2000) J. Bacteriol., 182, 3998-4004.
Sambrook, J., Fritsch, E. F., and Maniatis, T. (1989) Molecular cloning: a laboratory manual, 2nd ed., Cold Spring Harbor Laboratory Press, Cold Spring Harbor, N.Y.
Sanger, F., Nicklen, S., and Coulson, A. R. (1977) Proc. Natl. Acad. Sci. U.S.A., 74, 5463-5467.
Yoon, H.-J., Hashimoto, W., Miyake, O., Okamoto, M., Mikami, B., and Murata, K. (2000) Protein Expr. Purif., 19, 84-90.

Example 6

Molecular Breeding (2) of Strain A1 (Bacterium Belonging to the genus *Sphingomonas*)

Identification of strain A1 (of bacterium belonging to the genus *Sphingomonas*)-derived high expression promoter and preparation of a system expressing ethanol synthesis genes at high levels DNA microarray Genes that are constantly expressed at high levels regardless of various culture conditions (carbon source, shaking rate, alginate concentration) were selected based on standardized microarray data in order to search for strong promoters in the strain A1. A wild-type strain A1 was cultured under the following various conditions.

Medium: 0.5% or 3% alginate medium (0.5% or 3% sodium alginate, 0.1% $(NH_4)_2SO_4$, 0.1% $KH_2PO_4$, 0.1% $Na_2HPO_4$, 0.01% $MgSO_4.7H_2O$, 0.01% yeast extract, pH 8.0).
Shaking frequency: 50 spm or 100 spm.
Culture time: ($OD_{600}$, around 0.8) or up to stationary phase ($OD_{600}$, around 2.0).
The following conditions were always employed.
Culture solution volume: 30 mL (100 mL flask).
Temperature: 32° C.

The collected cells were immediately suspended in an RNA protect bacteria reagent (QIAGEN), so as to inhibit RNA degradation. Subsequently, total RNA was extracted by a hot phenol method and then purified using an RNeasy Midi Kit (QIAGEN). The thus obtained RNA was subjected to thorough analysis of gene expression levels using a DNA microarray (Roche Diagnostics). Information concerning the genome sequence of the strain A1 and open reading frames was obtained from the database constructed at the Murata laboratory, Division of Food Science and Biotechnology, Graduate School of Agriculture, Kyoto University. 3,985 target genes were designed on an array chip. A 60-mer synthetic oligonucleotide was used for each probe to increase specificity and 2 sets, each consisting of 9 probes per gene, were prepared and immobilized on the chip. After hybridization, the array was scanned using a Genepix 4000B (Axon) at a wavelength of 532 nm and resolving power of 5 μm. The thus obtained data were standardized with RMA algorithm. As a result, it was demonstrated that SPH828, 1616, 1617, 2330, 2357, 2611, 2661, 2987, 3626, and 3746 genes were expressed at high levels independently of culture conditions.

Promoter Essay

Figure 10:
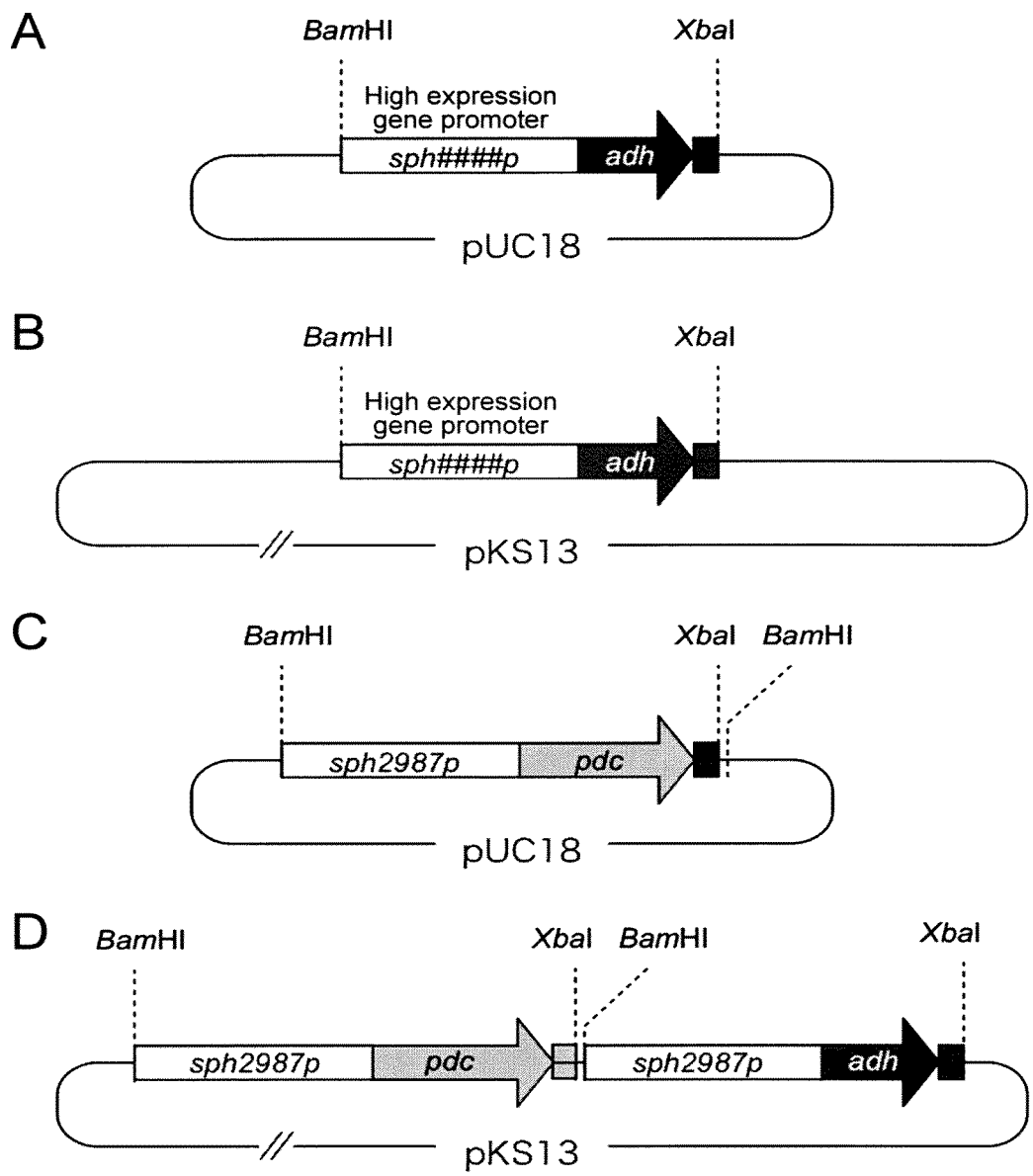
FIG. 10 shows schematic diagrams of plasmids into which various promoters used in Example 6 were introduced.

For comparison of genes for promoter activity, an adh gene was ligated to a presumed promoter region of a candidate gene and then the resultant was introduced into the strain A1. The pUC18-adh plasmid prepared in Example 1 was linearized by an inverse PCR method and then the native promoter region of adh was removed. KOD-Plus was used as DNA polymerase. 5'-GCTTCTTCAACTTTTTATATTC-CTTTCGTCAACGAAATG-3' (SEQ ID NO: 23) and 5'-CGGGATCCCCGGGTACCGAGCTCGAATTC-3' (SEQ ID NO: 24) were used as primers. Also, each 2-kb promoter region fragment of the above 10 genes was amplified by PCR. KOD-Plus was used as DNA polymerase, the genomic DNA of the strain A1 was used as template DNA, and 2 types of synthetic oligonucleotide were used as primers. The thus amplified fragment was ligated to a pUC18-adh fragment linearized using an in fusion cloning kit (Takara Bio Inc.) (pUC18-sph####p-adh plasmid, wherein "####" denotes gene No., FIG. 10A). These plasmids were cleaved with BamH I and Xba I, and then the resultant was ligated to a pKS13 vector treated with BamH I/Xba I (pKS13-sph####p-adh plasmid, FIG. 10B). The vector was introduced into a wild-type strain A1 by tri-parental mating.

Figure 11:
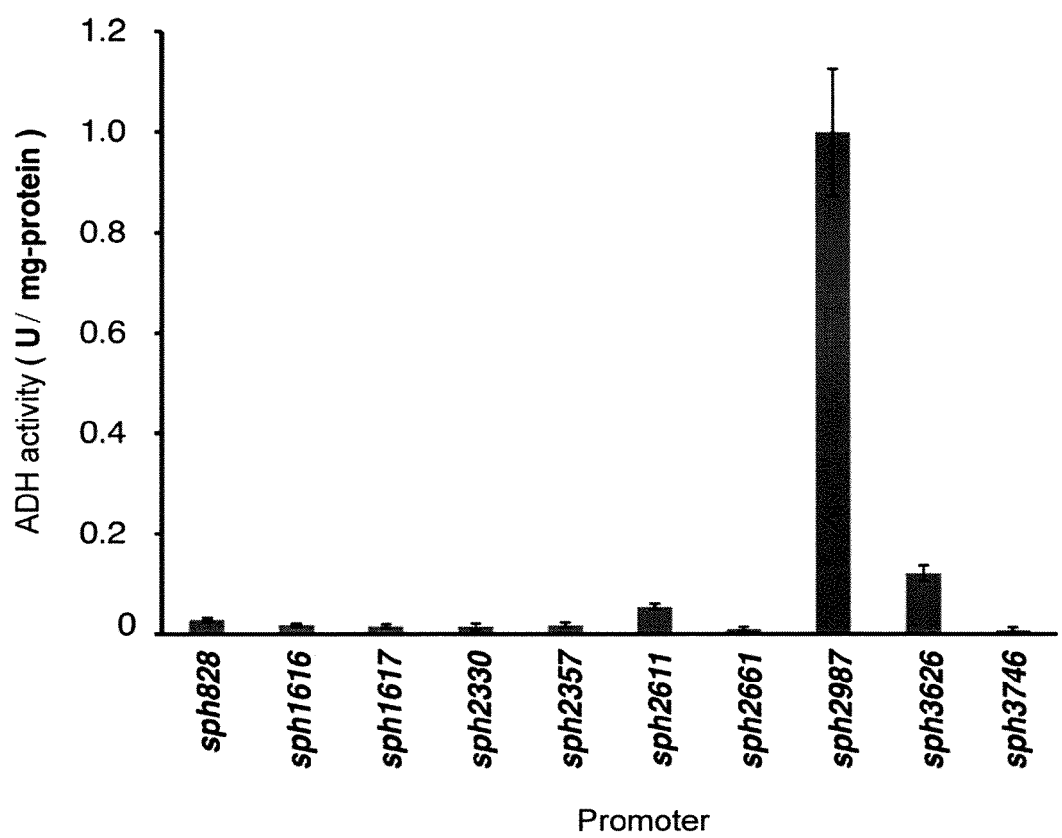
FIG. 11 shows each promoter activity of the strain A1. Error bar denotes standard deviation (n=3).

Preparation of crude enzyme fractions from the strain A1 and measurement of ADH activity were performed in a manner similar to that in Example 2. The ADH activity of the strain A1, into which adh ligated to the presumed promoter regions of the above 10 genes had been introduced, was measured. As a result, the promoter (sph2987 promoter, SEQ ID NO: 25) of the SPH2987 gene exhibited the highest ADH activity (FIG. 11).

Preparation of EPv 14 Strain 1 into which Genes Had been Introduced

A system for the expression of PDC and ADH at high levels in the strain A1 was constructed using the sph2987 promoter. A DNA fragment excluding adh ORF and the terminator of the pUC-sph2987p-adh plasmid used in promoter assay was amplified by inverse PCR. KOD-Plus was used as DNA polymerase. 5'-CATGGTTGTCTGCCCTTTTTACATAG-TATGCGTTGAACAC-3' (SEQ ID NO: 26) and 5'-TGC TCTAGAGGATCCGTCGACCTGCAGGCATGCAAGCT TGG-3' (SEQ ID NO: 27) having Xba I/BamH I site (underlined) were used as primers. Similarly, ORF and a terminator region of the pdc gene were amplified by PCR. The pUC18-pdc plasmid prepared in Example 1 was used as a template. 5'-AGTTATACTGTCGGTACCTATTTAGCGGAGC-3' (SEQ ID NO: 28) and 5'-TGC TCTAGAACGGGCTTTTCGCCTTAAGCTCTAAG-3' (SEQ ID NO: 29) having an Xba I site (underlined) were used as primers. Both gene fragments amplified by PCR were treated with Xba I restriction enzyme and then ligated by ligation reaction (pUC18-sph2987p-pdc plasmid, FIG. 10C). pUC18-sph2987p-pdc was cleaved with BamH I and then a fragment containing the pdc gene was ligated to the pKS13-sph2987p-adh plasmid treated with BamH I (pKS13-sph2987p-pdc-sph2987p-adh plasmid, FIG. 10D). The thus prepared plasmid was introduced into the strain A1 by tri-parental mating (strain EPv14).

Enzyme Activity of Strain EPv14

Figure 12:
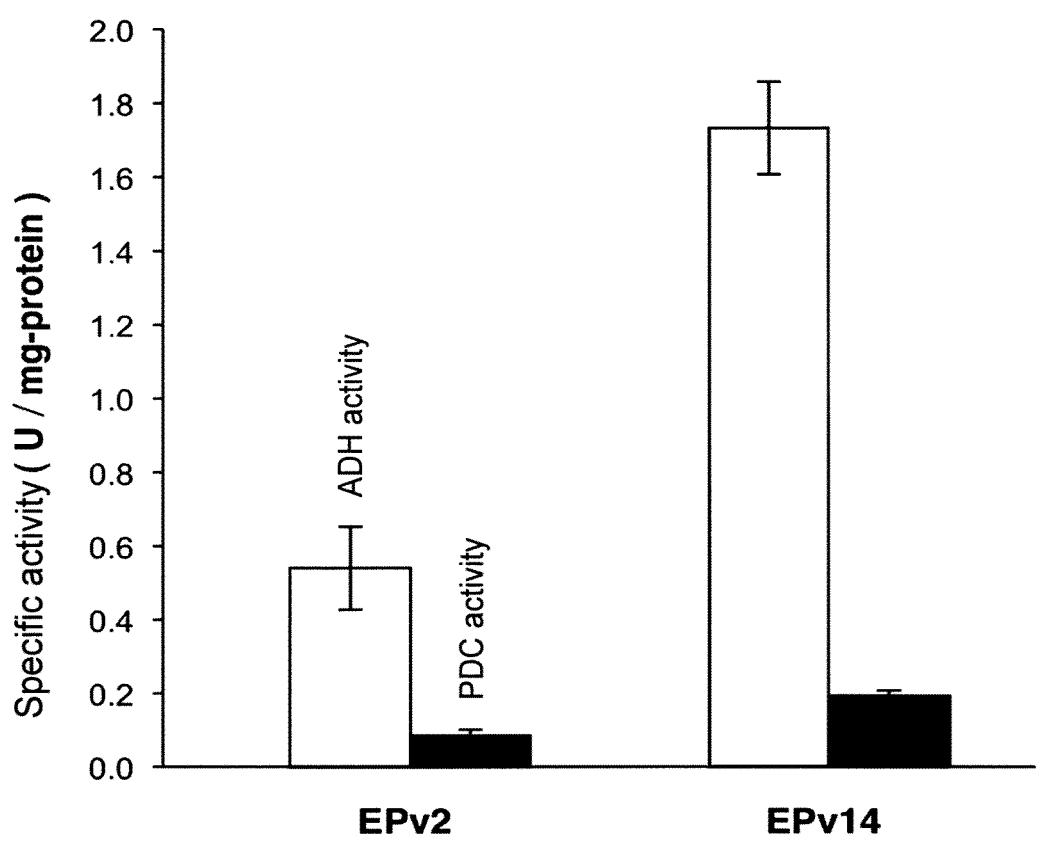
FIG. 12 shows PDC activity and ADH activity in the strain EPv2 and the strain EPv14. Error bar denotes standard deviation (n=3).

ADH activity and PDC activity contained in cell extracts of the wild-type strain A1 and strain A1 EPv14 into which the genes had been introduced were measured (FIG. 12). The strain EPv14 was cultured in a 4% alginate medium (100 mL/300-mL flask) at 32° C. and 50 spm (2-cm stroke, reciprocal shaking) for 96 hours. A fraction of the crude enzyme solution was obtained by ultrasonic disruption and then ADH activity (white) and PDC activity (gray) were measured. The modified strain A1 exhibited ADH activity 3.2 times and PDC activity 2.3 times greater than the strain EPv2. It was revealed based on the results that the promoter of the SPH2987 gene is effective for high-level expression and other enzyme genes.

Ethanol Production by Strain EPv14

Ethanol production was performed using EPv14. Culture conditions are as follows:
Medium: 4% alginate medium (4% sodium alginate, 0.1% $(NH_4)_2SO_4$, 0.1% $KH_2PO_4$, 0.1% $Na_2HPO_4$, 0.01% $MgSO_4.7H_2O$, 0.01% yeast extract, pH 8.0).
Vessel: 300-mL flask.
Temperature: 32° C.
Shaking: 50 spm (2-cm stroke).

Figure 13:
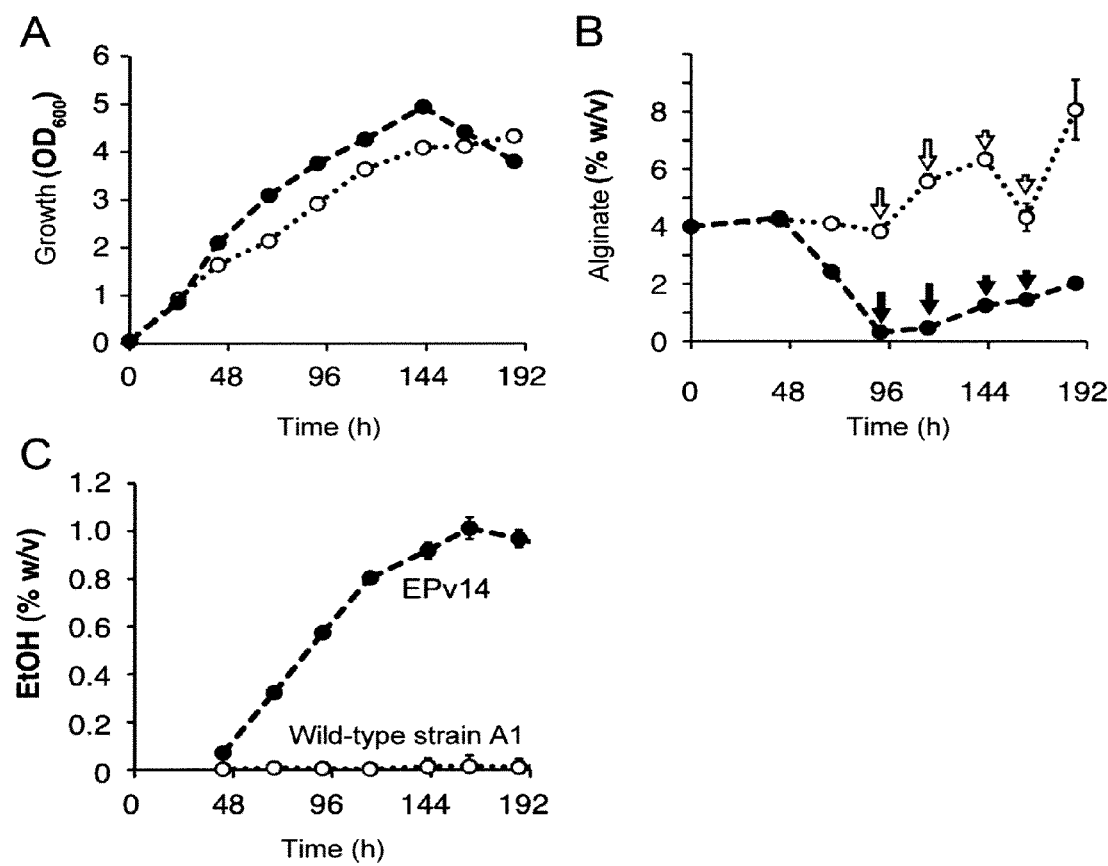
FIG. 13 shows the results of ethanol production by the strain EPv14.

On days 3 and 4 of culture, 1 g of alginate powder was added per flask, and on days 5 and 6 of culture, 0.5 g of alginate powder was added per flask. On day 7 of culture, it was confirmed that ethanol accumulation had taken place to result in more than 1% ethanol in the medium (FIG. 13).

Example 7

Molecular Breeding (3) of Strain A1 (Bacterium Belonging to the genus *Sphingomonas*)

Preparation of Genetically Modified Strain A1 Through Introduction of 2 Copies of the pdc and adh Genes and Ethanol Production Preparation of Strain A1 EPv 77 Through Introduction of the Genes The sph2987 promoter, the adh gene, and the pdc gene were ligated in series, as follows. The pUC18-2987adh plasmid was linearized by an inverse PCR method. 5'-AATTA-GAAAGCGCTCAGGAAGAGTTCTTCAACTTC-3' (SEQ ID NO: 30) and 5'-TGC TCTAGAGGATCCGTCGACCTGCAGGCATGCAAGCT TGG-3' (SEQ ID NO: 31) having Xba I/BamH I site (underlined) were used as primers. Similarly, the ORF and the terminator region of the pdc gene were amplified by PCR. The pUC18-pdc plasmid prepared in Example was used as a template. 5'-GGAGTAAGCAATGAGTTATACTGTCGG-TACCTATTTAG-3' (SEQ ID NO: 32) and 5'-TGC TCTAGAACGGGCTTTTCGCCTTAAGCTCTAAG-3' (SEQ ID NO: 33) having an Xba I site (underlined) were used as primers. Both gene fragments amplified by PCR were treated with an Xba I restriction enzyme and then ligated by ligation reaction (pUC18-sph2987p-adh-pdc plasmid, FIG. 14A). The pUC18-sph2987p-adh-pdc plasmid was cleaved with BamH I and Xba I. A DNA fragment containing the pdc and adh genes were ligated to a pKS13 vector treated with BamH Xba I (pKS13-sph2987p-adh-pdc plasmid, FIG. 14B). Furthermore, a fragment containing the pdc and adh genes was excised by treatment of the pUC18-sph2987p-adh-pdc plasmid with BamH I, purified, and then ligated to the pKS13-sph2987p-adh-pdc plasmid treated with BamH I (pKS13-

Figure 14:
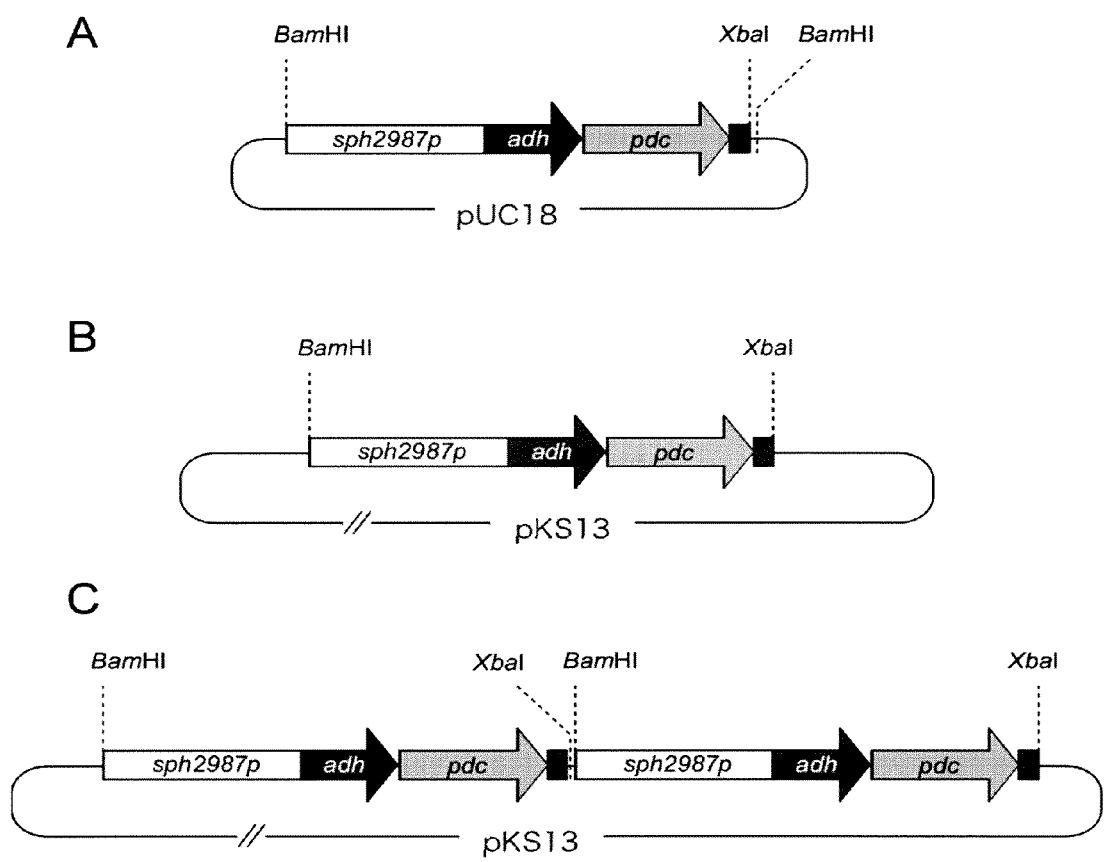
FIG. 14 shows schematic diagrams of plasmids into which multiple copies of genes used in Example 7 were introduced.

(sph2987p-adh-pdc)$_2$ plasmid, FIG. 14C). The thus prepared plasmid was introduced by tri-parental mating into the strain A1 (strain EPv77).

Enzyme Activity of Strain EPv77

Figure 15:
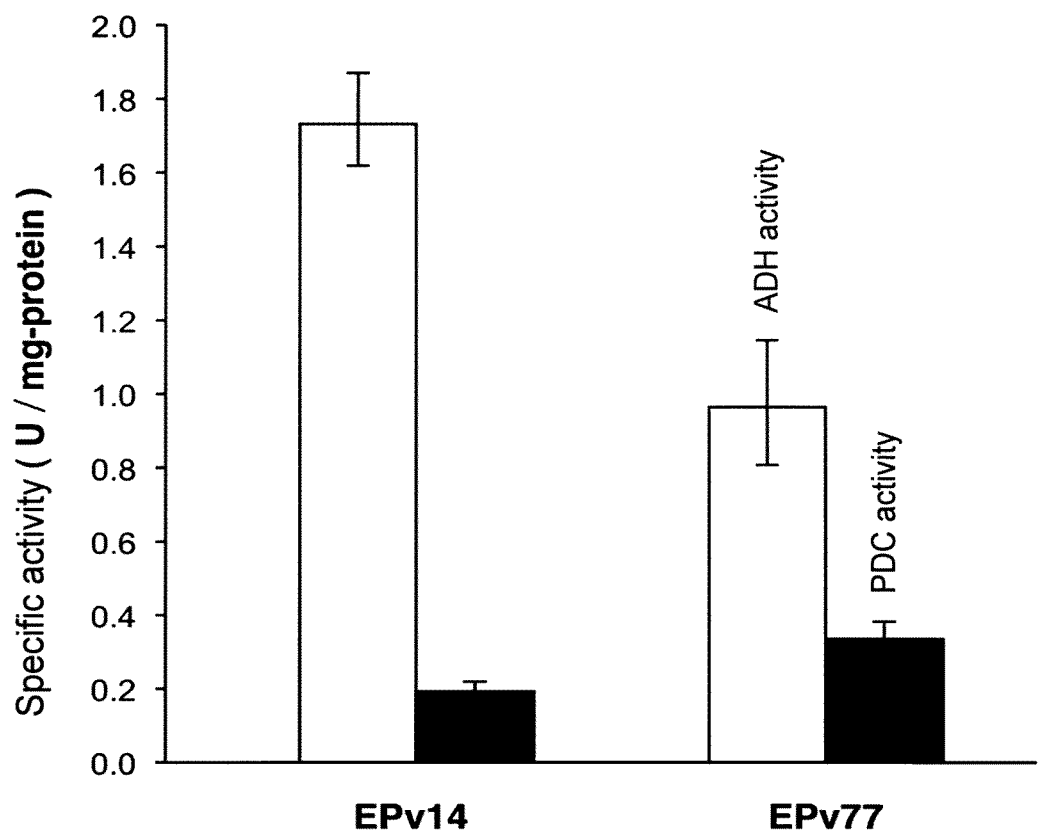
FIG. 15 shows PDC activity and ADH activity in a modified strain A1. Error bar denotes standard deviation (n=3).

PDC activity and ADH activity of the thus prepared strain EPv77 were measured (FIG. 15). The strain EPv77 was cultured in a 4% alginate medium (100-mL/300-mL flask) at 32° C. and 50 spm (2-cm stroke, reciprocal shaking) for 96 hours. A fraction of the crude enzyme solution was obtained by ultrasonic disruption. ADH activity (white) and PDC activity (gray) were measured. EPv77 exhibited ADH activity that had decreased to a level 0.55 times that of the strain EPv14, but exhibited PDC activity that was 1.73 times the same.

Ethanol Production by Strain EPv77

Figure 16:
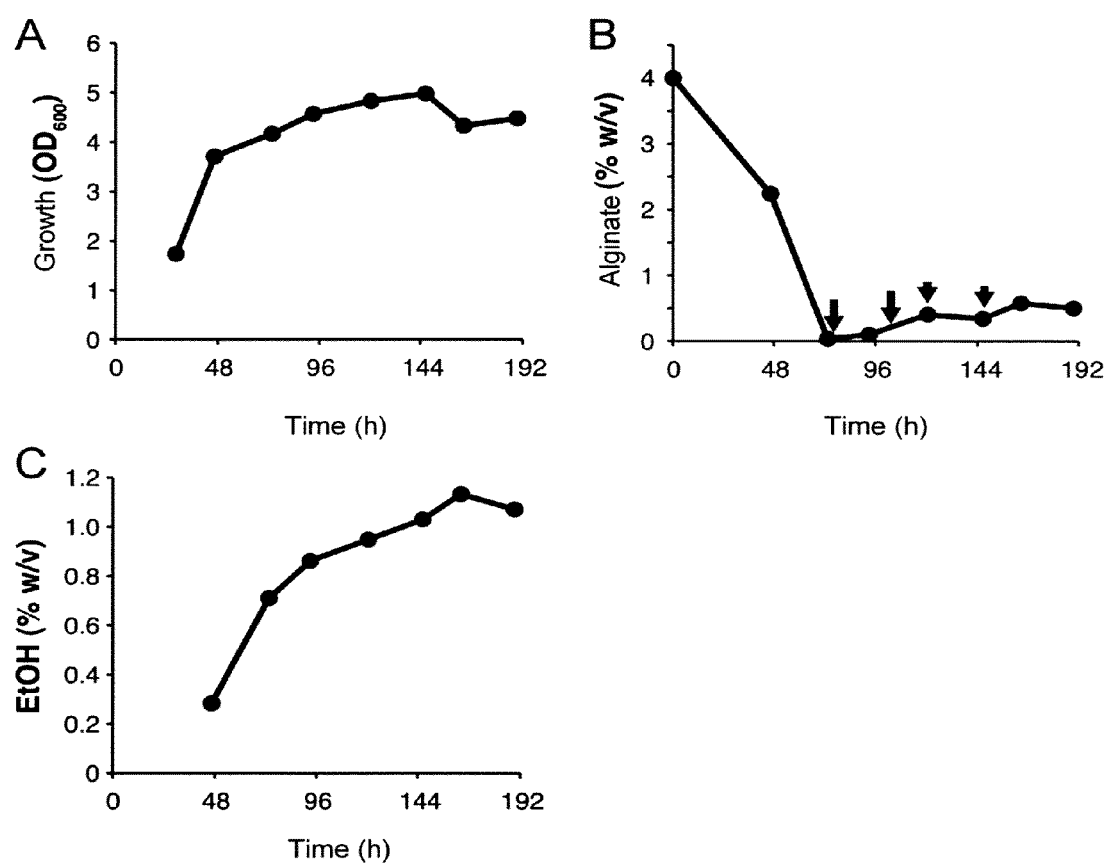
FIG. 16 shows the results of ethanol production by a strain EPv77.

Culture conditions for ethanol production are as follows.
Medium: 4% alginate medium (4% sodium alginate, 0.1% (NH$_4$)$_2$SO$_4$, 0.1% KH$_2$PO$_4$, 0.1% Na$_2$HPO$_4$, 0.01% MgSO$_4$.7H$_2$O, 0.01% yeast extract, pH 8.0).
Vessel: 300-mL flask.
Temperature: 32° C.
Shaking: 50 spm (2-cm stroke).
On days 3 and 4 of culture, 1 g of alginate powder was added and on days 5 and 6 of culture, 0.5 g of alginate powder was added per flask. Ethanol production was performed using EPv77. As a result, EPv77 exhibited good growth, high alginate consumption, and high ethanol production capacity. On day 7 of culture, it was confirmed that ethanol accumulation had taken place to result in 1.13% ethanol in the medium (FIG. 16).

Example 8

Molecular Breeding (4) of Strain A1 (Bacterium Belonging to the genus *Sphingomonas*)

Introduction of Coenzyme Regeneration System

Ethanol production (ADH reaction) requires coenzyme NADH and the supply of NADH may control the ethanol production rate. A NAD$^+$-dependent formate dehydrogenase gene (FDH1, NM__001183808) for generation of CO$_2$ and NADH from formic acid and NAD$^+$ was cloned from yeast *Saccharomyces cerevisiae* and then introduced into the modified strain A1 EPv2.

Plasmid Construction

ORF of the FDH1 gene was amplified by PCR. KOD-Plus polymerase, the genomic DNA of S. cerevisiae strain BY4742 as a template, and 5'-GGGCAGACAACCATGTC-GAAGGGAAAGGTTTTGCTGGTTCTTTA C-3' (SEQ ID NO: 34) and 5'-TTTCCTGTTTTGAAATTATTTCTTCT-GTCCATAAGCTCTGGTGGC-3' (SEQ ID NO: 35) as primers were used. Also, a DNA fragment excluding the adh ORF of the pUC18-sph2987p-adh plasmid (Example 6) used in promoter assay was amplified by inverse PCR. KOD-Plus was used as DNA polymerase. 5'-TTTCAAAACAG-GAAAACGGTTTTCCGTCCTGTCTTGAT-3' (SEQ ID NO: 36) and 5'-CATGGTTGTCTGCCCTTTTTACATAG-TATGCGTTGAACAC-3' (SEQ ID NO: 37) were used as primers. Both fragments were ligated using an in fusion cloning kit (pUC18-sph2987p-FDH1 plasmid). This plasmid was cleaved with BamH I and Xba I and then ligated to a pJRD215 vector (Davison et al. 1987) treated with BamH Xba I (pJRD215-sph2987p-FDH1 plasmid, FIG. 17B), and then the vector was introduced by tri-parental mating into the strain A1 EPv2 (Example 1) into which the genes had been introduced (strain EPv10).

Comparison of Intracellular NAD$^+$ and NADH Concentrations

The wild-type strain, the Strain A1s EPv2 and EPv10, into which the genes had been introduced, were cultured and then intracellular NAD$^+$ and NADH concentrations were measured. Extraction of NAD$^+$ and NADH from cells and measurement of concentrations were performed according to Leonado et al. (1996).

Culture conditions are as follows.
Medium: 3% alginate medium (3% sodium alginate, 0.1% ammonium sulfate (wile-type strain, EPv2) or 0.1% ammonium formate (EPv10). 0.1% KH$_2$PO$_4$, 0.1% Na$_2$HPO$_4$, 0.01% MgSO$_4$.7H$_2$O, 0.01% yeast extract, pH 8.0).
Liquid volume: 100-mL/300-mL flask.
Shaking frequency: 50 spm (2-cm stroke).
Temperature: 32° C.
Time: 3 days.

After culture, 1×10$^9$ cells were collected by centrifugation, immediately frozen in liquid nitrogen, and then stored at −80° C. Immediately before measurement, 500 µL of 0.2 M hydrochloric acid (NAD$^+$ extraction) or 0.2 M sodium hydroxide (NADH extraction) was added to the frozen cells for suspension. Cells were left to stand at 100° C. for 10 minutes and then subjected to 5 minutes of centrifugation at 5,000×g. Subsequently, a supernatant was collected and then designated as a NAD$^+$/NADH extraction sample. NAD$^+$/NADH quantification by cyclic assay was performed as follows. Fifty (50) µL of 1 M Bicine-NaOH buffer (pH 8.0), 125 µL of the NAD$^+$/NADH extraction sample, 125 µL, of 0.1 M NaOH (NAD$^+$ measurement) or 0.1 M HCl (NADH measurement), 50 µL of 16.6 mM phenazine ethosulfate, 50 µL of 4.2 mM 3-(4,5-dimethylthiazol-2-yl)-2,5-diphenyltetrazolium bromide, 50 µL of ethanol, and 50 µL of 40 mM EDTA-2Na (pH 8.0) were mixed in a cuvette and then the mixture was left to stand at 30° C. for 3 minutes. ADH (0.5 U/µL, Roche) was added to and mixed with the resultant, so as to initiate reaction. The initial rate of increase in absorbance at 570 nm was measured using an absorptiometer (MPS-2000, Shimadzu). Similarly, measurement was performed using authentic samples of NAD$^+$ and NADH to produce a calibration curve, and then NAD$^+$ and NADH concentrations in a sample were found. The intracellular NADH/NAD$^+$ ratio for the strain EPv10 into which FDH1 had been introduced was increased than that for the wild-type strain and the strain EPv2, suggesting that the NADH regeneration system was functioning (Table 2).

TABLE 2

Comparison of intracellular NAD$^+$ and NADH concentrations

| | Concentration* | | NADH/NAD$^+$ |
|---|---|---|---|
| | NAD$^+$ | NADH | Ratio |
| Wild-type strain A1 | 1.32 | 0.48 | 0.36 |
| EPv2 | 1.60 | 1.13 | 0.71 |
| EPv10 | 0.76 | 0.87 | 1.14 |

*The concentration of NADH or NAD$^+$ is indicated with µmole per 2.5 × 10$^8$ cells.

Ethanol Production by Strain EPv10

Figure 18:
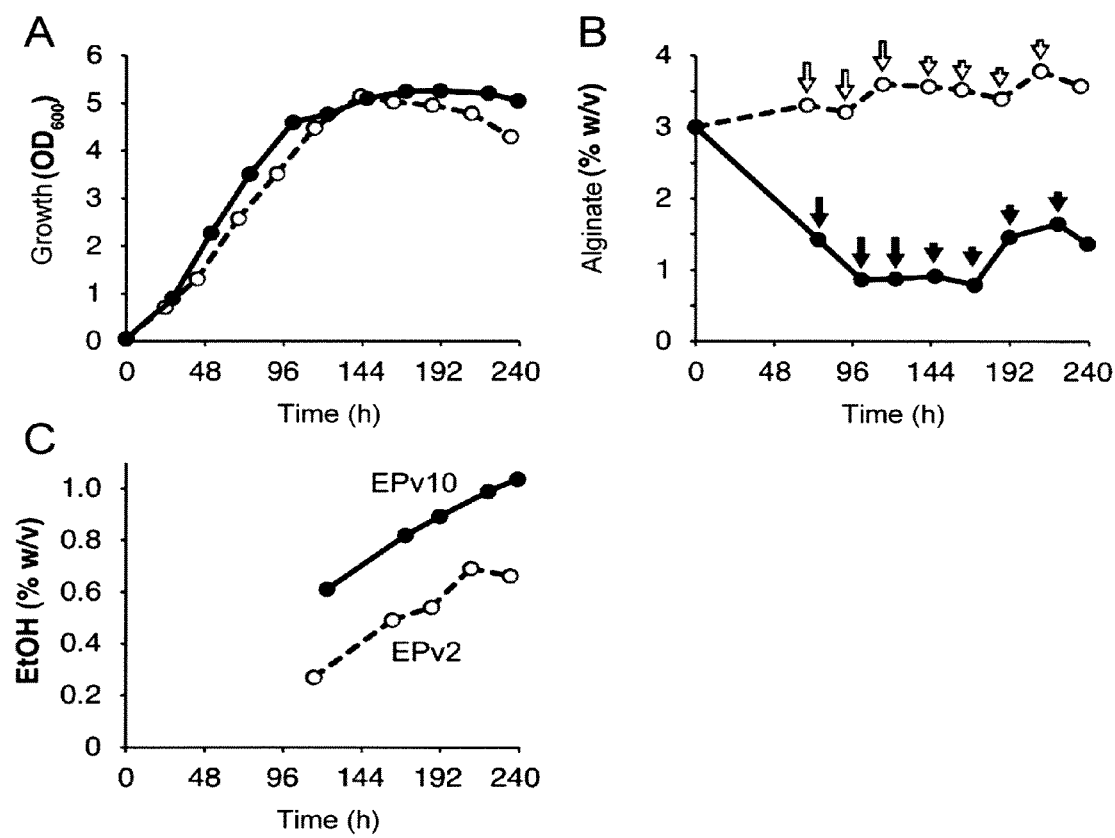
FIG. 18 shows the results of ethanol production by EPv10.

Culture conditions for ethanol production are as follows.
Medium: 3% alginate medium (3% sodium alginate, 0.1% (NH$_4$)$_2$SO$_4$, 0.1% KH$_2$PO$_4$, 0.1% Na$_2$HPO$_4$, 0.01% MgSO$_4$.7H$_2$O, 0.01% yeast extract, pH 8.0).
Vessel: 300-mL flask.
Temperature: 32° C.
Shaking: 50 spm (2-cm stroke).
On days 3 and 4, 1 g of alginate oligosaccharide powder was added and on days 5 to 9 of culture, 0.5 g of alginate oligosaccharide powder was added per flask. Ethanol production was performed using EPv10. The ethanol production rate was almost the same as that of EPv2. However, EPv10 performed ethanol production for a period longer than that of EPv2. It was confirmed that ethanol accumulation had taken place to result in more than 1% ethanol in the medium (FIG. 18C).

REFERENCES IN THIS EXAMPLE

Davison, J., Heuterspreute, M., Chevalier, N., Ha-Thi, V. and Brunel, F. (1987) Gene 51, 275-280.
Leonardo, M. R., Dailly, Y. and Clark, D. P. (1996) J. Bacteriol. 178, 6013-6018.

Example 9

Molecular Breeding (5) of Strain A1 (Bacterium Belonging to the genus *Sphingomonas*)

Figure 19:
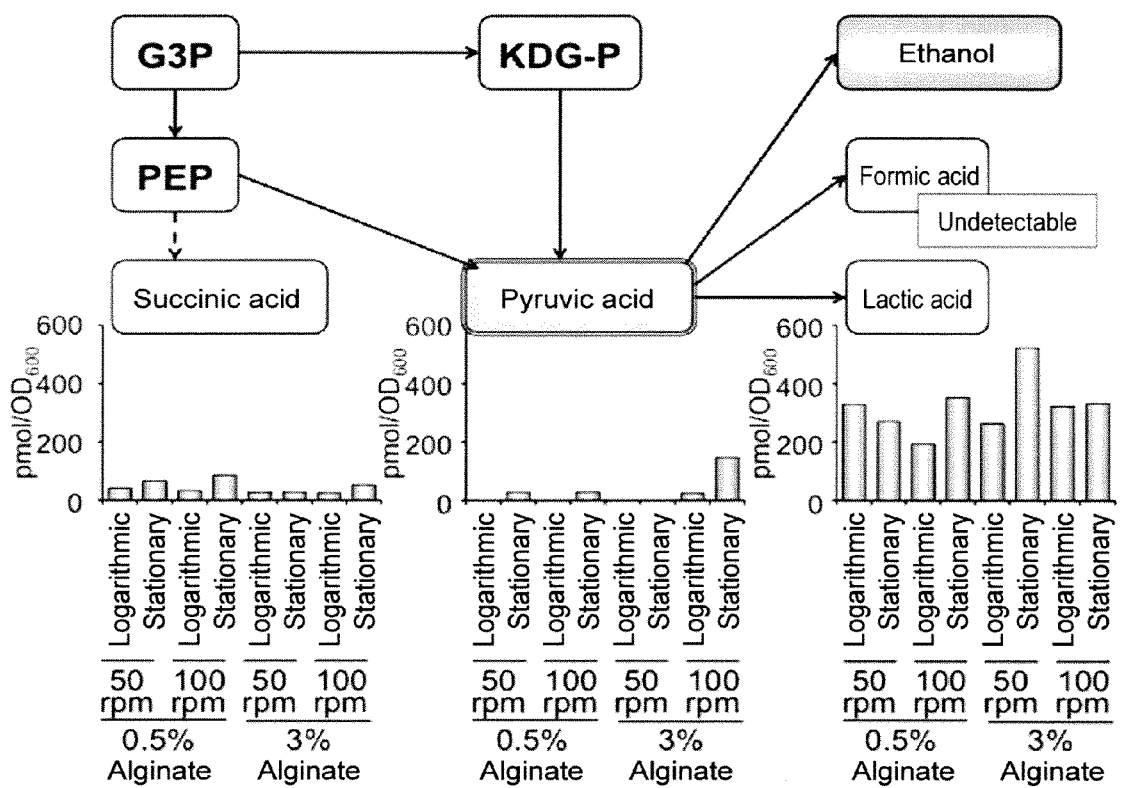
FIG. 19 shows the results of metabolome analysis of the strain A1. High-level accumulation of lactic acid was observed regardless of culture conditions. Succinic acid was accumulated to some extent under any conditions and relatively high-level accumulation thereof was observed in the stationary phase. Accumulation of pyruvic acid was observed in the stationary phase.
Figure 22:
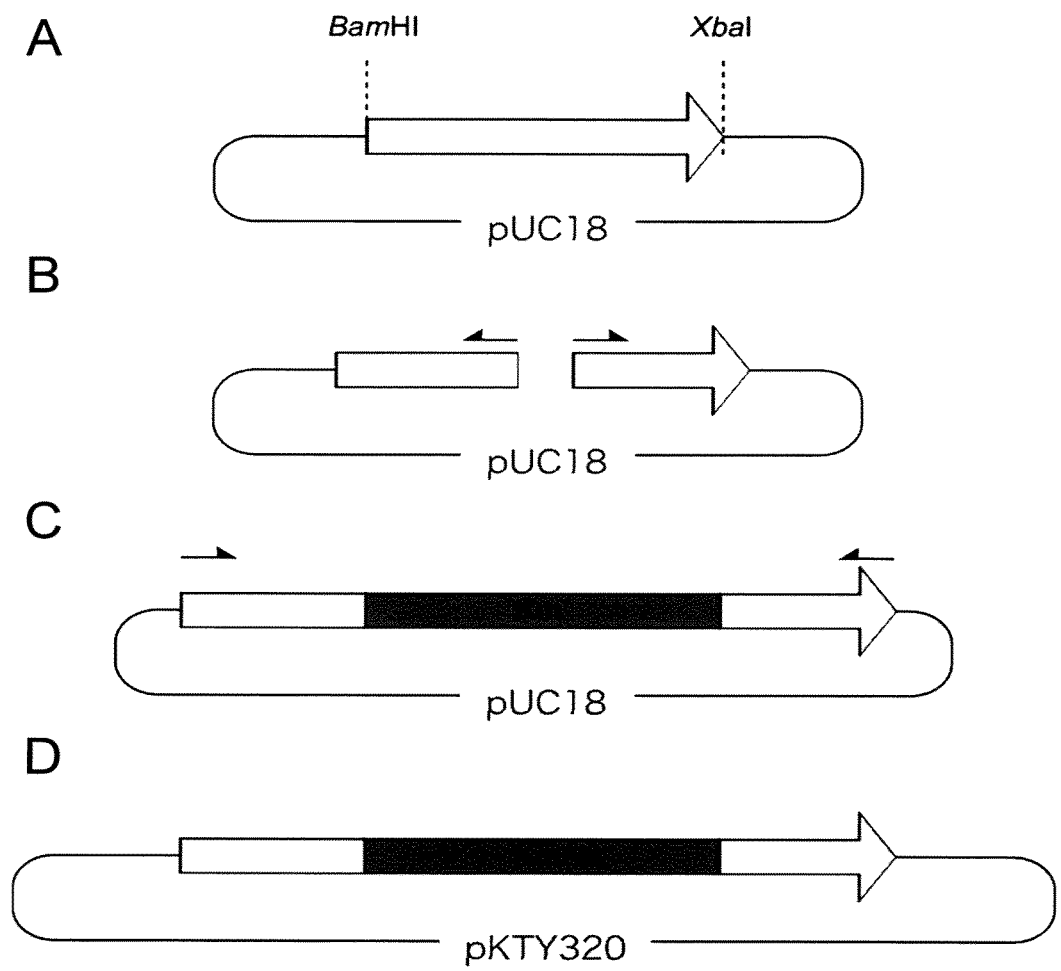
FIG. 22 shows schematic diagrams of plasmids used in Example 9. Each white bold arrow indicates an ORF fragment of ldh or sdh and each gray portion indicates a Km$^r$ cassette. Each thin arrow indicates a primer position used for PCR.

Preparation of Synthesis Gene (of Byproduct)-Disrupted Strain
Metabolome Analysis Metabolome analysis was conducted to search for a metabolic pathway competing with ethanol production. The wild-type strain A1 was cultured under the following various conditions.
Medium: 0.5% or 3% alginate medium (0.5% or 3% sodium alginate, 0.1% $(NH_4)_2SO_4$, 0.1% $KH_2PO_4$, 0.1% $Na_2HPO_4$, 0.01% $MgSO_4 \cdot 7H_2O$, 0.01% yeast extract, pH 8.0).
Shaking frequency: 50 spm or 100 spm.
Culture time: ($OD_{600}$, around 0.8) or up to stationary phase ($OD_{600}$, around 2.0).
The following conditions were always employed.
Culture solution volume: 30 mL (100-mL flask).
Temperature: 32° C.
After culture, cells were collected by centrifugation, washed 3 times with ice-cooled distilled water, and then suspended in cold methanol, so that cells were immobilized. Metabolites were subjected to liquid liquid extraction and analysis by capillary electrophoresis-time-of-flight mass spectroscopy at human metabolome technologies. Fluctuations for metabolites were observed. As a result, pyruvic acid accumulation was confirmed only in the stationary phase. Also, high-level accumulation of lactic acid and the same of succinic acid, which are metabolites from pyruvic acid, were confirmed in all samples (FIG. 19).
Blocking of Lactic Acid Synthesis Pathway and Succinic Acid Synthesis Pathway Disruption of a lactate dehydrogenase (LDH) gene involved in lactic acid synthesis and a fumarate reductase (SDH) gene involved in succinic acid synthesis was attempted to block the pathways toward lactic acid and succinic acid. The ldh and sdh homologs of the strain A1 were specified by a homology search. Each gene with the highest homology was subjected to disruption. Each gene fragment was amplified by PCR. KOD-Plus was used as DNA polymerase. The genomic DNA of the strain A1 was used as a template. For amplification of the ldh gene, 5'-CCG TCTAGATGCACGCGTCCTGTTGGCCGTCAG-3' (SEQ ID NO: 38) (FIG. 20, P1) having an Xba I site (underlined) and 5'-CGCGGATCCAGATCACCTCGTTGGCCAGCG GTTCCTTG-3' (SEQ ID NO: 39) (FIG. 20, P2) having a BamH I site (underlined) were used as primers. For amplification of the sdh gene, 5'-CCGTCTAGACGATT CAACTCTCCGAATCCGGCCTGAAGAC-3' (SEQ ID NO: 40) (FIG. 21, P1) having an Xba I site (underlined) and 5'-ATC GGATCCGCGTCTTCAGCGCGATCGTTTCAACG-3' (SEQ ID NO: 41) (FIG. 21, P2) having a BamH I site (underlined) were used as primers. Each gene fragment amplified by PCR was treated with BamH I and Xba I and then ligated to a pUC18 vector treated with BamH I and Xba I. The plasmid was linearized by inverse PCR so that each gene was cut open in the middle, and then a pUC4K plasmid-derived kanamycin resistance gene ($Km^r$) was inserted. For inverse PCR for the ldh gene, 5'-TGCGCCGAGCGAACCGAAGGTCTTG-3' (SEQ ID NO: 42) (FIG. 20, P3) and 5'-GGCCGCATTGGC-CAATGCTCGATGC-3' (SEQ ID NO: 43) (FIG. 20, P4) were used as primers. For inverse PCR for sdh, 5'-GCGCCCTG-CACCACCGGTAGCGAAC-3' (SEQ ID NO: 44) (FIG. 21, P3) and 5'-CACGAATTCGCTGCTCGACCTGCTTGTG-3' (SEQ ID NO: 45) (FIG. 21, P4) were used as primers. $Km^r$ was excised from pUC4K by treatment with BamH I, blunt-ended by treatment with a Klenow fragment, and then connected to an inverse PCR product. The ldh or sdh fragment into which $Km^r$ had been inserted was amplified using the thus generated plasmid as a template and the above primer pair. The resultant was connected to a pKTY320 vector (Kimbara et al. 1989) treated with Hinc II (FIG. 22). The thus prepared plasmid was introduced by tri-parental mating into the wild-type strain A1. A disruption strain was selected by selection using kanamycin and confirmation of double cross-over by PCR.

The LDH enzyme activity of the ldh gene-disrupted strain was measured. The LDH activity decreased to about ⅕ that of the wild-type strain. Introduction of both pdc and adh genes (pKS13-sph2987p-pdc-sph2987p-adh plasmid, Example 6) into the LDH gene-disrupted strain can result in significant improvement in ethanol productivity, compared with EPv14. On the other hand, sdh gene disruption was difficult, strongly suggesting the involvement of SDH in energy production via the TCA cycle.

REFERENCES IN THIS EXAMPLE

Kimbara, K. Hashimoto, T., Fukuda, M., Koana, T., Takagi, M., Oishi, M. and Yano, K. (1989) J. Bacteriol. 171, 2740-2747.

All publications, patents and patent applications cited in this specification are herein incorporated by reference in their entirety.
Sequence Listing Free Text
SEQ ID NOS: 11-24, 26-45 primers

The invention claimed is:

1. A method for producing ethanol using alginate as a raw material, comprising:

introducing a gene encoding pyruvate decarboxylase derived from *Zymomonas mobilis* and a gene encoding alcohol dehydrogenase derived from *Zymomonas mobilis* into a *Sphingomonas* sp. strain A1 which has an ABC transporter, alginate-binding proteins, endo-/exo-type alginate lyases, keto acid reductase, kinase, and aldolase, to obtain a transformed *Sphingomonas* sp. strain A1; and then culturing the transformed *Sphingomonas* sp. strain A1 for 5 to 7 days by adding alginate or alginate oligosaccharide into a medium in an amount of 1 g/100 ml once per day starting from the third day of the culture, to produce a concentration of 0.7% (w/v) or more of ethanol in the medium, wherein the gene encoding pyruvate decarboxylase derived from *Zymomonas mobilis* and the gene encoding alcohol dehydrogenase derived from *Zymomonas mobilis* are controlled by a *Sphingomonas* sp. strain A1-derived SPH2987 gene promoter consisting of the nucleotide sequence of SEQ ID NO: 25 and are thus expressed at high levels.

2. The method of claim 1, wherein:

(i) the transformed *Sphingomonas* sp. strain A1 comprises multiple copies of the gene encoding pyruvate decarboxylase, multiple copies of the gene encoding alcohol dehydrogenase, or multiple copies of both genes;

(ii) the transformed *Sphingomonas* sp. strain A1 comprises a gene encoding formate dehydrogenase, which is an enzyme of an NADH regeneration system;

or both (i) and (ii).

3. The method of claim 1, further comprising removing a gene involved in lactic acid synthesis from the transformed *Sphingomonas* sp. strain A1.

4. The method of claim 1, wherein the transformed *Sphingomonas* sp. strain A1 is immobilized.

5. The method of claim 2, wherein the transformed *Sphingomonas* sp. strain A2 comprises multiple copies of the gene encoding pyruvate decarboxylase, multiple copies of the gene encoding alcohol dehydrogenase, or multiple copies of both genes.

6. The method of claim 2, wherein the transformed *Sphingomonas* sp. strain A1 comprises a gene encoding formate dehydrogenase, which is an enzyme of an NADH regeneration system.

7. The method of claim 2, wherein the transformed *Sphingomonas* sp. strain A1 comprises multiple copies of the gene encoding pyruvate decarboxylase, multiple copies of the gene encoding alcohol dehydrogenase, or multiple copies of both genes; and the transformed *Sphingomonas* sp. strain A1 comprises a gene encoding formate dehydrogenase, which is an enzyme of an NADH regeneration system.

8. The method of claim 1, wherein the culturing comprises adding alginate.

9. The method of claim 1, wherein the culturing comprises adding alginate oligosaccharide.

* * * * *

SEQUENCE LISTING

```
<160> NUMBER OF SEQ ID NOS: 47

<210> SEQ ID NO 1
<211> LENGTH: 1707
<212> TYPE: DNA
<213> ORGANISM: Zymomonas mobilis

<400> SEQUENCE: 1
atgagttata ctgtcggtac ctatttagcg gagcggcttg tccagattgg tctcaagcat        60
```

| | |
|---|---|
| cacttcgcag tcgcgggcga ctacaacctc gtccttcttg acaacctgct tttgaacaaa | 120 |
| aacatggagc aggtttattg ctgtaacgaa ctgaactgcg gtttcagtgc agaaggttat | 180 |
| gctcgtgcca aaggcgcagc agcagccgtc gttacctaca gcgtcggtgc gctttccgca | 240 |
| tttgatgcta tcggtggcgc ctatgcagaa aaccttccgg ttatcctgat ctccggtgct | 300 |
| ccgaacaaca atgatcacgc tgctggtcac gtgttgcatc acgctcttgg caaaaccgac | 360 |
| tatcactatc agttggaaat ggccaagaac atcacgccg ccgctgaagc gatttacacc | 420 |
| ccggaagaag ctccggctaa aatcgatcac gtgattaaaa ctgctcttcg tgagaagaag | 480 |
| ccggtttatc tcgaaatcgc ttgcaacatt gcttccatgc cctgcgccgc tcctggaccg | 540 |
| gcaagcgcat tgttcaatga cgaagccagc gacgaagctt ctttgaatgc agcggttgaa | 600 |
| gaaaccctga aattcatcgc caaccgcgac aaagttgccg tcctcgtcgg cagcaagctg | 660 |
| cgcgcagctg gtgctgaaga agctgctgtc aaatttgctg atgctctcgg tggcgcagtt | 720 |
| gctaccatgg ctgctgcaaa aagcttcttc ccagaagaaa acccgcatta tcatcggcacc | 780 |
| tcatggggtg aagtcagcta tccgggcgtt gaaaagacga tgaaagaagc cgatgcggtt | 840 |
| atcgctctgg ctcctgtctt caacgactac tccaccactg gttggacgga tattcctgat | 900 |
| cctaagaaac tggttctcgc tgaaccgcgt tctgtcgtcg ttaacggcat tcgcttcccc | 960 |
| agcgtccatc tgaaagacta tctgacccgt ttggctcaga aagtttccaa gaaaaccggt | 1020 |
| gcattggact tcttcaaatc cctcaatgca ggtgaactga agaaagccgc tccggctgat | 1080 |
| ccgagtgctc cgttggtcaa cgcagaaatc gcccgtcagg tcgaagctct tctgaccccg | 1140 |
| aacacgacgg ttattgctga aaccggtgac tcttggttca atgctcagcg catgaagctc | 1200 |
| ccgaacggtg ctcgcgttga atatgaaatg cagtggggtc acattggttg gtccgttcct | 1260 |
| gccgccttcg gttatgccgt cggtgctccg gaacgtcgca catcctcat ggttggtgat | 1320 |
| ggttccttcc agctgacggc tcaggaagtc gctcagatgg ttcgcctgaa actgccggtt | 1380 |
| atcatcttct tgatcaataa ctatggttac accatcgaag ttatgatcca tgatggtccg | 1440 |
| tacaacaaca tcaagaactg ggattatgcc ggtctgatgg aagtgttcaa cggtaacggt | 1500 |
| ggttatgaca gcggtgctgg taaggcctg aaggctaaaa ccggtggcga actggcagaa | 1560 |
| gctatcaagg ttgctctggc aaacaccgac ggcccaaccc tgatcgaatg cttcatcggt | 1620 |
| cgtgaagact gcactgaaga attggtcaaa tggggtaagc gcgttgctgc cgccaacagc | 1680 |
| cgtaagcctg ttaacaagct cctctag | 1707 |

<210> SEQ ID NO 2
<211> LENGTH: 1152
<212> TYPE: DNA
<213> ORGANISM: Zymomonas mobilis

<400> SEQUENCE: 2

| | |
|---|---|
| atggcttctt caacttttta tattccttc gtcaacgaaa tgggcgaagg ttcgcttgaa | 60 |
| aaagcaatca aggatcttaa cggcagcggc tttaaaaatg cgctgatcgt ttctgatgct | 120 |
| ttcatgaaca aatccggtgt tgtgaagcag gttgctgacc tgttgaaagc acagggtatt | 180 |
| aattctgctg tttatgatgg cgttatgccg aacccgactg ttaccgcagt tctggaaggc | 240 |
| cttaagatcc tgaaggataa caattcagac ttcgtcatct ccctcggtgg tggttctccc | 300 |
| catgactgcg ccaaagccat cgctctggtc gcaaccaatg gtggtgaagt caaagactac | 360 |
| gaaggtatcg acaaatctaa gaaacctgcc ctgcctttga tgtcaatcaa cacgacggct | 420 |
| ggtacggctt ctgaaatgac gcgtttctgc atcatcactg atgaagtccg tcacgttaag | 480 |

```
atggccattg ttgaccgtca cgttaccccg atggtttccg tcaacgatcc tctgttgatg      540
gttggtatgc caaaaggcct gaccgccgcc accggtatgg atgctctgac ccacgcattt      600
gaagcttatt cttcaacggc agctactccg atcaccgatg cttgcgcttt gaaagcagct      660
tccatgatcg ctaagaatct gaagaccgct tgcgacaacg gtaaggatat gccggctcgt      720
gaagctatgg cttatgccca attcctcgct ggtatggcct tcaacaacgc ttcgcttggt      780
tatgtccatg ctatggctca ccagttgggc ggttactaca acctgccgca tggtgtctgc      840
aacgctgttc tgcttccgca tgttctggct tataacgcct ctgtcgttgc tggtcgtctg      900
aaagacgttg tgttgctat gggtctcgat atcgccaatc tcggtgataa agaaggcgca      960
gaagccacca ttcaggctgt tcgcgatctg gctgcttcca ttggtattcc agcaaacctg     1020
accgagctgg gtgctaagaa agaagatgtg ccgcttcttg ctgaccacgc tctgaaagat     1080
gcttgtgctc tgaccaaccc gcgtcagggt gatcagaaag aagttgaaga actcttcctg     1140
agcgctttct aa                                                         1152
```

<210> SEQ ID NO 3
<211> LENGTH: 975
<212> TYPE: DNA
<213> ORGANISM: Sphingomonas sp

<400> SEQUENCE: 3

```
atgacaagcg ccaccaaggc acagagcata ccgctgcccg cagcgacgct cgacgtgcgt       60
tcgaaaccgc tcgaacgcct gtggaaagac atcaaacgcg actggctgtt gtatgccatg      120
ttgctaccca ccatcatctg gttcctgatc tttctgtaca agccgatgat cggcctgcag      180
atggcgttca agcagtacag cgcctggaaa ggcatcgccg gcagtccgtg gatcgggttc      240
gaccacttcg tcacgctgtt ccagagcgaa cagttcattc gcgccatcaa gaacacactg      300
accctgtcgg gtctgtcgct gttgttcggc ttcccgatgc cgatcctgct ggcgctgatg      360
atcaacgagg tctactcgaa gggttatcgc aaggcagtgc agaccatcgt ctatctgcct      420
cacttcatct ccatcgtgat cgtggccggc ctcgtggtga cattcctgtc gcccagcacc      480
ggcgtggtca caacatgct gagctggatc ggtctgacc gggtgtactt cctgacccag      540
ccggagtggt tccgtccgat ctacatcagc tcgaacatct ggaaggaagc gggcttcgat      600
tcgatcgtgt atctggccgc gatcatgagc atcaacccgg cgctgtatga atcggcacag      660
gtggacggtg ccacgcgctg gcagatgatc acgcgcatca ccctgccctg catcgtcccg      720
accatcgcgt gctgctggt gatccgcctg ggccacatcc tggaagtggg cttcgagtac      780
atcatcctgc tgtaccagcc gacgacctac gaaacggccg acgtgatcag tacctacatc      840
tatcgtctgg gcctgcaagg ggcgcgctac gacatcgcta ccgccgccgg catttcaat      900 gccgtggtgg ccctggtgat cgtgctgttc gccaaccaca tgagccgccg tatcaccaag      960
accggcgtgt tctga                                                       975
```

<210> SEQ ID NO 4
<211> LENGTH: 882
<212> TYPE: DNA
<213> ORGANISM: Sphingomonas sp

<400> SEQUENCE: 4

```
atgctcgcca caccttttcta tagccgctcc gacaggatct tcggcatcgt caacgccgtc       60
ctgctgggca cttcgcgct ctgtgcgctg tacccgatca tctacatctt ctcgatgtcg       120
atcagctcgg gcgcggcggt cacacagggc cgcgtattcc tgcttccggt ggacatcgac      180
```

-continued

```
ttttcggcct acggccgcgt gctccacgac aagctgttct ggacgtcgta tgccaacacc     240
attttctaca cggtgttcgg tgtggtcacg agcctgatct tcatcgtgcc cggtgcgtat     300
gcgctgtcca agccgcgtat ccgtggccgc cgcgtgttcg gcttcatcat cgccttcacg     360
atgtggttca acgcagggat gatcccgttc ttcctgaaca tgcgcgacct cgggctgctc     420
gacaaccgct tcggcatctt gatcggcttc gcctgtaacg cgttcaacat catcctgatg     480
cgcaactact tcgaatcgat ctcagcatcg ttcgaagagg ccgcacgcat ggatggcgcc     540
aatgacctgc agattctgtg aaggtgtac atcccgctgg ccaagccggc gctggccacc      600
atcaccctgc tctgcgccat ctctcgctgg aacggttact tctgggccat ggtgctgctg     660
cgcgccgaag agaagatccc gctgcaggtg tacttgaaga agaccatcgt cgatctgaac     720
gtcaacgaag agttcgcagg cgccctgctc accaactcgt attcgatgga aaccgtggtg     780
ggcgccatca tcgtgatgtc gatcatcccc gtgatcatcg tctacccggt ggtgcagaag     840
tacttcacca agggtgtgat gctcggaggc gtaaaagaat aa                        882

<210> SEQ ID NO 5
<211> LENGTH: 1092
<212> TYPE: DNA
<213> ORGANISM: Sphingomonas sp

<400> SEQUENCE: 5
gtggtagcaa gcgtcagcat tcagaacgtc gtcaagcgtt acgacaagac gactgtggtc      60
catggtgtca gcctggatat cgaaccgggt gaattcgtcg tgctggtcgg cccttcgggc     120
tgcggcaagt cgacgacact acgcatggtg gccggtctgg aagaaatcag cggcggcacg     180
atcaggatcg acggccgcgt catcaacgac ctcgcgccaa aagatcgcga cgtcgccatg     240
gtgttccaga actacgcgct ctacccgcac ctgaatgtgc gcgacaacat ctcctttggc     300
ctgcgcctga gcgcaccaa gaaatccgtc atcgatgcag ccgtgaagac ggccgccgac     360
atcctcggcc tgcaaccgct gctcgaacgc aagccttccg atcttttccgg cggtcagcgt    420 caacgcgttg ccatgggccg cgcgatcgtg cgcgaccccga aggtcttcct cttcgacgaa   480
ccgctctcca acctcgacgc caaactgcgc acgcagatgc gcgccgaaat caagcggctg    540
caccaacgcc tgggcaccac cgtcatttat gtgacgcacg atcaggtcga agccatgaca    600
ttggcagatc gcatcgtggt catgcgcgac ggtctgatcg aacagatcgg caagccgatg    660
gacctgttcc tccatccggc caataccttc gtggccagct tcattggttc gccgccgatg    720
aacctgatgc cggcacgcat tgccgtcgac agcacgcagc acgttgaatt gaacggtggc    780
aaccgcatca gcctgctgcc ccgtgcaggc acacatctgg caccgggtca ggaagtggtg    840
tttggcattc gcccggaaga cgtcacgctc gacggcgtcg aaggctccga acgtgcgcag    900
atcaaggcca cggtggacat cgtcgaaccg ctcggttcgg aatcgatcct ccacgctacg    960 gtcgcgatc actcgctggt ggtgaaggtg gcggcctca atgaagtaca tccgggcgat     1020
ccggtcacgc tgcatgtcga tctgacacgc gtgcacctgt tcgacgccca gtcacaggcc    1080
tctatttact ga                                                       1092

<210> SEQ ID NO 6
<211> LENGTH: 1581
<212> TYPE: DNA
<213> ORGANISM: Sphingomonas sp

<400> SEQUENCE: 6
atgaaaaagc tggtactggc catggccatc ggaagttccg cattgatgtt cgcggctccg      60
```

-continued

| | |
|---|---|
| tcggtggtcg cgcgcgaggc gacgtgggtg accgaaaagc cactcacgct caagatccac | 120 |
| atgcacttcc gcgacaagtg ggtgtgggac gagaactggc cggtggccag agaagtcgcc | 180 |
| cgcctcacca acgtcaagct cgtcggtgta gccaacaggg ccgctaccaa cagccaggaa | 240 |
| cagttcaacc tgatgatggc ctcgggccag ttgccggaca tcgtcggcgg cgacaacctg | 300 |
| aaggacaagt tcatccgcta cgggatggaa ggcgcgttca ttccgctcaa caagttgatc | 360 |
| gatcagaacg cccccaacct gaaggcattc ttcaagacac accccgaagt ccagcgcgcc | 420 |
| atcacagcgc cggacggcaa tatctattac ctgccctacg tgccggacgg gctggtgtcg | 480 |
| cgcgggtact tcatccgcca ggactggctc gacaaactgc atctgaagac cccgcagacc | 540 |
| gtcgatgagc tgtacaccgt gctcaaggcg ttcaaggaaa agacccgaa cggcaacggc | 600 |
| aaggccgatg agattccgtt catcaaccgc gacccgaag aggtcttccg tctcgtgaat | 660 |
| ttctggggcg ctcgctcgac cggttcgaat acgtggatgg atttctacgt cgagaacggc | 720 |
| aagatcaagc atccgttcgc cgaagtcgcc ttcaaggacg gcatcaagca cgtggcccag | 780 |
| tggtacaagg aaggtctcat cgaccccgag atcttcacgc gcaaggcgcg ctcacgcgaa | 840 |
| cagaccttcg gcaacaacat cggcggcatg acgcatgact ggttcgccag cacggcgctg | 900 |
| ttcaacgatg cgctgtccaa gaacatcccc ggcttcaagc tcgtgccgat ggcgccgccc | 960 |
| atcaacagca agggccagcg ttgggaagaa gacgctcgcc agattccgcg ccccgacggc | 1020 |
| tgggcgatca cggcgaccaa caagaacccg gtcgaaacca tcaagctgtt cgacttctac | 1080 |
| ttcgggccga agggccgcga gctgtccaac ttcggcgtac cgggcctgac gtatgacatc | 1140 |
| aagaacggca agccggtcta caaggacacg gtgctgaagg ccgcccagcc ggtgaacaac | 1200 |
| cagatgtacg acatcggcgc gcagattccc atcggcttct ggcaggacta cgagtacgag | 1260 |
| cgtcaatgga ccaacgacgt cgcactccag ggcatcgaca tgtacatcaa gaacaagtac | 1320 |
| gtgctgcccc aattcaccgg cgtcaacctg actgtcgaag agcgcgagat ctacgacaaa | 1380 |
| tactggccgg acgtgaagac ctacatgttc gaaatgggcc agtcctgggt gatgggcacc | 1440 |
| aaggacccgg aaaaaacgtg gaacgactat cagcagcaac tgaagaaccg cggtttctat | 1500 |
| caggtcatga tcgttatgca gaaggcctat gaccggcagt acggcggggc agcgaagcca | 1560 |
| gcccaggtcg gagccaagta a | 1581 |

<210> SEQ ID NO 7
<211> LENGTH: 1551
<212> TYPE: DNA
<213> ORGANISM: Sphingomonas sp

<400> SEQUENCE: 7

| | |
|---|---|
| atgaagaaga tgatgttgtc cgtcgcagca gtggccacgc tgatggcctt tgccgcgccc | 60 |
| gtcgccacgg cgaaggaggc cacctgggtg accgacaagc ccttgacgct gaagatccat | 120 |
| atgcacttcc gcgacaagtg ggtgtgggac gagaactggc cggtcgccaa ggaatcgttc | 180 |
| cgcctgacca acgtgaagct gcaaagcgtc gccaacaagg ccgccacgaa cagccaggaa | 240 |
| cagttcaacc tgatgatggc ttcgggcgac ctgccggacg tcgttggcgg tgacaacctg | 300 |
| aaggacaagt tcattcagta cgggcaggaa ggcgcattcg ttccgctcaa caagctgatc | 360 |
| gaccaatacg ccccgcatat caaggcgttc ttcaaatcgc accggaagt cgagcgcgcc | 420 |
| atcaaggcgc cggacggcaa catctacttc attccttacg tgccggacgg cgtggtcgcg | 480 |
| cgcggctact tcatccgcga agactggctc aagaagctca acctgaagcc gcctcagaac | 540 |
| atcgatgaac tctacaccgt gctcaaggcg ttcaaggaaa agacccgaa cggcaacggc | 600 |

-continued

```
aaggccgatg aagtgccctt catcgaccgc catccggacg aagtcttccg cctggtgaac    660
ttctggggcg cgcgttcgtc ggggtccgat aactacatgg acttctacat cgacaacggc    720
cgcgtcaagc acccgtgggc cgaaaccgcc ttccgcgacg gcatgaagca tgtgcccag     780
tggtacaagg aaggcctgat cgacaaggaa atcttcaccc gcaaggcacg cgcacgcgaa    840
caaatgttcg gtggcaatct gggcggcttc acgcacgact ggttcgccag cacgatgacc    900
ttcaacgaag gtctggccaa gacggtgccg ggcttcaagc tgattccgat cgccccgccg    960
accaacagca agggccagcg ctgggaagaa gactcccgcc agaaggttcg tcccgatggc   1020
tgggccatca cggtgaagaa caagaacccg gtggaaacca tcaagttctt tgacttctac   1080
ttcagccgtc cgggccgcga catctccaac tttggcgttc cgggtgtcac gtatgacatc   1140
aagaacggca aggcggtgtt caaggattcc gtgctcaagt cgccgcagcc ggtcaacaac   1200
cagctctatg acatgggcgc acagatcccc atcggcttct ggcaggacta cgactacgaa   1260
cgtcagtgga ccacgcctga agcgcaggcc ggcatcgaca tgtacgtcaa gggcaagtac   1320
gtcatgcctg gcttgaagg cgtgaacatg acgcgtgaag agcgcgccat ctacgacaag   1380
tactgggccg acgttcgcac gtacatgtat gaaatgggcc aagcctgggt gatgggcacc   1440
aaggacgtgg acaagacctg gacgagtac cagcgtcagc tcaagctgcg cggtctctac   1500
caagtgctgc agatgatgca gcaagcctac gaccgtcaat acaagaacta a            1551
```

<210> SEQ ID NO 8
<211> LENGTH: 1926
<212> TYPE: DNA
<213> ORGANISM: Sphingomonas sp

<400> SEQUENCE: 8

```
atgcctttgg catgccttgc aacgacgcgc gtggggggctg cgcgcgaaaa atctggagac    60
agttcgatgt ttgacatccc gttcccgggg catggccgtc gtctggccgt cgccgcgctt   120
gcgttcgcag gttgtgcctt cgcgggcagc ctgcaggcac acccttcga ccaggccgtc   180
gtgaaagacc ccacggcctc gtatgtcgac gtcaaggcgc gtcgtacctt cttgcagagc   240
gggcagctcg atgaccgcct caaggcagcg ctgcccaagg agtacgactg cacgaccgag   300
gcaacgccta acccgcagca aggcgagatg gtcattccgc gccgttatct ttccggcaat   360
cacgccccgg tgaatccgga ctacgaaccg gtggtgacgc tttatcgtga tttcgagaaa   420
atttccgcca cgcttggaaa tctctacgtt gcgacgggca agccggtgta cgccacttgt   480
ctgctgaaca tgctggacaa gtgggccaag gccgacgcgt tgctcaacta cgaccccaag   540
tcgcagtcgt ggtaccaagt cgaatggtcg gcggcgaccg ccgcctttgc cctgtcgacg   600
atgatggccg agccgaacgt cgacacagcc cagcgcgagc gtgtggtgaa gtggctcaac   660
cgtgtggcgc gccatcagac gagctttccg gggggcgaca cgagttgctg caacaatcac   720
tcgtattggc gcggtcagga gcgaccatc atcggcgtga tcagcaagga cgatgaactc   780
ttccgttggg ggctggcccg ttatgtgcag gcgatggggc tgatcaatga agacggcagc   840
ttcgtgcatg aaatgacgcg tcacgaacag tccttgcact atcagaacta cgccatgctg   900
ccgctgacga tgattgccga acggcatca cgtcagggta tcgatctgta cgcgtacaaa   960
gagaacggtc gcgatattca ctcagcgcgc aagtttgtct ttgctgcggt gaagaacccg  1020
gacctcatca agaagtacgc ttccgagccg caggatacgc gtgccttcaa gccggggcgg  1080
ggcgacctga actggatcga ataccagcgc gcgcgctttg gttttgccga tgagctgggc  1140
ttcatgacgg tgccgatctt cgatccgcgt accggtggtt cgggcacttt gctggcgtac  1200
```

| | |
|---|---|
| aaaccgcaag gcgcggcagc gcaggcgccg gtgtccgccc cggcagcggc gcattcgtcg | 1260 |
| atcgacctgt cgaagtggaa gctgcagatt ccggtcgacc cgatcgatgt cgccacgcgt | 1320 |
| gatctgctca agggttatca ggacaagtac ttctacgtcg acaaggatgg ctcgcttgcc | 1380 |
| ttctggtgtc cggccagcgg tttcaagacg acggccaaca cgaagtaccc gcgcagcgag | 1440 |
| ctgcgcgaaa tgctcgatcc cgacaaccac gcggtgaatt ggggctggca aggcacccac | 1500 |
| gaaatgaatc tgcgcggagc ggtgatgcac gtgtcgccca gtggcaagac cattgtcatg | 1560 |
| cagattcatg ccgtcatgcc cgatggctcg aatgcgccgc cgctggtcaa ggggcagttc | 1620 |
| tacaagaaca cgctggattt tcttgtgaag aactcggccg ctggcggcaa ggacacgcac | 1680 |
| tacgtgttcg aaggcatcga actgggcaag ccgtacgatg cgcagatcaa agtggtggac | 1740 |
| ggtgtgttgt cgatgacggt caacgggcag accaagaccg tcgatttcgt cgccaaggac | 1800 |
| gccggctgga agacctgaa gttctatttc aaggcgggca attacttgca ggaccgccag | 1860 |
| gctgacgggt cggacaccag cgcgctggtc aagttgtaca agctcgacgt aaagcactcg | 1920 |
| agctga | 1926 |

<210> SEQ ID NO 9
<211> LENGTH: 2289
<212> TYPE: DNA
<213> ORGANISM: Sphingomonas sp

<400> SEQUENCE: 9

| | |
|---|---|
| gtgatgaaga agctggaaca gccgcagtcc gcggacatga caatcagata tttccccgac | 60 |
| agtgacacgc tgaccgaaaa tccgccgcgc tttctgtggc tgccggaact cgacagccag | 120 |
| gcgcgctacg ccgtgcgcgt ggtgtcggac gcggggaaag agacggtgtt cggcgacatc | 180 |
| cagcacaact tcttccgccc cgacgtcaca ctgacgccgg gtagctacac ctggtcttac | 240 |
| gctctgtggg acgcagccgc aggcaaggtc gactccgact ggagctcccc gcgcagcttc | 300 |
| gttctgcccg ccgacgcgcc cgctgtgccc ggcatgcgcc ataaagaacg gtacgccgag | 360 |
| tgcgacatga cgcacccgcg cctgtggctg tcgcaaagcg aagccaccgc gttgggcaag | 420 |
| agcgtcgcca ccgacccgga tcactgcaag tgggccaact tcatggccaa gtcggtcacg | 480 |
| ccatggatgt cgcgcgagat catcgccgag ccgcagccct accccaacaa caagcgcacg | 540 |
| ccggccctgt ggcgcaagat gtacatcgac tgccaggaag tgatctacgc gatccgccac | 600 |
| ctggccatcg ccggtcgtgt gctgggtgat gcggccatga ccgcccgcgc caaggaatgg | 660 |
| ctgctcgccg tcgccgcgtg ggacgtgcgt ggcccgacct gccgcgacta caacgacgaa | 720 |
| gccgccttcc gcatcgcggc agcactggcc tggggctacg actggctgca cgacgaactg | 780 |
| tcggacatcg aacgcgccaa cgtgcgcgaa tcgctgacgg tgcgcacgcg cgaagtcgcc | 840 |
| aaccacgtga tcaaccgcgc caagattcat atcttcccgt acgacagcca cgccgtgcgt | 900 |
| tcgatttcgt cggtgctggt gccctgctcc atcgtgctgc tgggcgaagt gcccgaagcc | 960 |
| cagaagtggc tcgactactc catcgatttc tacgacgcga tctacccacc gtggggcggc | 1020 |
| gtggacggcg gctgggccga gggtccgcac tactggatga cggccatggc ctacttcacc | 1080 |
| gaggcggcca acctcgtgtt gaagtacttc aagcatgacc tgtacaagcg cccgttcttc | 1140 |
| cagagcactg gctggttccc gctctacacc aaggccccgg acacgcgtcg tgcgtgcttt | 1200 |
| ggcgatgact ccacgctcgg cgacctgccc tgcctgaagg tgggctacaa cctgcgccaa | 1260 |
| ttcgccggcg tcaccggcaa cccgtacttc cagtggtact cgaagaggt gtgccgcaac | 1320 |
| gatccgggca ccgaaatgga gttctacaac tacggttggt gggacctgaa cttcgacgac | 1380 |

```
gtgcagtacc tgcacgactt cccgcacatc gaagcgaagg cgccgtccga catcgacacc    1440
gtcaagtact tggcgatgt tggctgggtc gcgctgcaac ggcacatgga caagccggat     1500
cagcacatcc agttcctcac caaggccagc gacttcggct cgatcagtca cagccatgga    1560
gaccagggtg cgttcctgct gtatggctac ggcgaagacc tggccatcca gagcggctac    1620
tacatcggtt tcggcaccac catgcacaag gaatggcgcc gactgaccaa atcgaagaac    1680
gccattctca tcgacgggaa ggggcaatat tcaggttcga acaaagccga atgcctcaag    1740
gcgcaaggtc atgtgctgga gtaggcacg cgtaacggcg cgcacttcat cagcctcgac     1800
ccgaccgacg cgtacaaggc cgaggtgccc tacctcaccc gctatcgtcg cgacattcac    1860
ttcgtgcatg accgcttctt cgtcatcgtc gacgacgtcg aactggaaca ggacggcagc    1920
gtgcagtggc tcatgcacac cttcaagccg tgcgaactcg gctcgcaggt gttccgctac    1980
cacggtgaca agcgggcct gaatggcgaa ttcgtctatt gctcgtccgg cccggtgagc     2040
atcgagaaca cggtctcgta cgccaatatc gatcagagcg aagttgaagg actgccaccg    2100
caatccacgc tggtggcgag caccggcgcc gcacgtcgcc acacattggt gaccttgctc    2160
acaccgtacg cactgtcggc gccgctgcgc gtattccact tcaacgacga tcagggcttc    2220
tcgaccaacc tgtacttcca ggacggcaac aacgagatgt acaccatcac gttgcccaaa    2280
ccgttctaa                                                            2289

<210> SEQ ID NO 10
<211> LENGTH: 843
<212> TYPE: DNA
<213> ORGANISM: Sphingomonas sp

<400> SEQUENCE: 10
atgacatcca tcgccgtcac ctcaggcccc ggccgttttc acacaccgat aacgagagac      60
atatccatgt tcccagacct caaaggcaag cgcgttctga tcaccggttc gtcgcagggc     120
attggccttg ccaccgcccg cctcttcgcc cgtgcaggcg ccaaggtcgg cctgcacggc     180
cgcaaggcac ccgccaacat cgatgagacc atcgccagca tgcgcgccga cggcggcgat     240
gccgctttct tcgcggcgga cctggccacc tccgaagcct gccagcaact ggtcgatgag     300
ttcgtggcca gttcggtgg catcgacgtg ctcatcaaca atgctggcgg cctggtcggc      360
cgcaagccgc tccctgagat cgacgatacg ttctacgacg ccgtcatgga cgccaacatc     420
cgctcggtcg taatgaccac caagttcgcg ctgccccatc tggcggccgc agccaaggca     480
tccggccaga ccagcgcgt gatcagcacc gggtcgatcg ctggccacac cggtggcggc     540
cccggcgcag gtctgtatgg cgcagccaag gctttcctgc acaacgtgca caagaactgg    600
gtcgacttcc acaccaagga cggcgtgcgg ttcaacattg tgtcgccggg taccgtcgac    660
accgccttcc atgcagacaa gacgcaagac gtgcgcgacc gtatctccaa cggcatcccg    720
atggggcgct tcggcaccgc cgaagaaatg gcgccggcat tcttgttctt cgcctcgcac    780
ctggccagcg gttacatcac cggtcaggtg ctggacatca acggcgggca gtacaagcac    840
tga                                                                  843

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
```

```
gaggatcctc acttaatcca gaaacgggcg                                              30

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
gactgcagac gggcttttcg ccttaagc                                                28

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
gactgcagaa aggcaaaatc ggtaaccaca tctc                                         34

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ggtctagatt atgacggtag gcttaatagc ctg                                          33

<210> SEQ ID NO 15
<211> LENGTH: 39
<212> TYPE: DNA
<213> ORGANISM: Artificial Sequence
<220> FEATURE:
<223> OTHER INFORMATION: primer

<400> SEQUENCE: 15
ccggaattct tactagagga gcttgttaac aggcttacg                                    39

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
actagtatgt agggtgaggt tatagctatg gct                                          33

<210> SEQ ID NO 17
<211> LENGTH: 37
<212> TYPE: DNA
<213> ORGANISM: Artificial Sequence
<220> FEATURE:
<223> OTHER INFORMATION: primer

<400> SEQUENCE: 17
aacctctaga ccgtgatgct gggtgacgac cacgctg                                      37

<210> SEQ ID NO 18
<211> LENGTH: 38
<212> TYPE: DNA
<213> ORGANISM: Artificial Sequence
<220> FEATURE:
```

```
<223> OTHER INFORMATION: primer

<400> SEQUENCE: 18
aaccaagctt cggcgctgat tcggggcgaa tgttcgtc                              38

<210> SEQ ID NO 19
<211> LENGTH: 38
<212> TYPE: DNA
<213> ORGANISM: Artificial Sequence
<220> FEATURE:
<223> OTHER INFORMATION: primer

<400> SEQUENCE: 19
aaccgagctc gagggaaccg cagcggcgga tcgtgtcg                              38

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
aaccggatcc gcgcctattg tcagaaggcg ccgacctc                              38

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
ttgcggatcc gcagctcgaa aaggcttcct cgatcg                                36

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
ttgctctaga cccacacctg gaaggtgcgg gtgttgc                               37

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
gcttcttcaa ctttttatat tcctttcgtc aacgaaatg                             39

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
cgggatcccc gggtaccgag ctcgaattc                                       29

<210> SEQ ID NO 25
```

<211> LENGTH: 2008
<212> TYPE: DNA
<213> ORGANISM: Sphingomonas sp

<400> SEQUENCE: 25

```
aagcggctcc gggatagaac ccatcacctt cttcttgttg ctctttggcg gagagagagg    60
gattcgaacc ctcgatacga gttttagccc gtatgctccc ttagcagggg agtgccttcg   120
acctctcggc catctctcca aaagagcgcg catgttagcc gcagcgcgcc ctatcgtcaa   180
tgcaaatcag acaccaacct gatccaattc gaacgccttg tgcagaacgc gcacagccag   240
ttcgagatac ttctcatcga tggcaaccga aatcttgatt tcggaggtgg aaatcatctg   300
aatgttgatg ccttcctcgg ccagcgtacg gaacatcttg ctggcaatgc cgacatggga   360
tcgcatccca cgccaaccaa ccgaaaacctt ggccatcgaa cgatcgccac ggatttcgcg   420
cgcaccgacg tgcttttttga cgttctcgag gatcgccacc gcacgctcca tgtcgttgcg   480
attaacggta aaggagaagt ccgtcgtgcc atcgacgcca acgttctgaa tgatcatgtc   540
gacgtcgata ttggcttcgg ccaccgggcc gagaatctgg tacgcaatgc ccggacgatc   600
aggcacgccc agcaccgtca gcttggcttc gtcgcggttg aacgcgatgc cggaaatgat   660
cggttgttcc atcttgatgt catcctcaaa agtgatcagc gtgccctcgc cccccttcctg   720
gaaactggac agcacgcgca gccggacttt gtatttgccg gcgaattcga ctgaacggat   780
ctgcagcacc ttggagccga gactggccat ctcgagcatt tcttcaaagg tgatgaagtc   840
gagcttgcgg gcttccggca cgacgcgcgg atcggtcgta taacgccgt cgacgtcggt   900
gtagatctgg cactcgtcgg cacgcagggc agcggccaag gcaactccgg tggtgtcgga   960
accaccgcga ccgactgtgg tgatgttgcc agcctcatca ccccctgga aaccggcaac   1020
gacgacgacg caaccttcgt cgagatcctt gcgcatgcgc tcttcgtcga tcttgagaat   1080
gcgcgcgcgg gtaaacgagc tgtcagtcag gatacgaacc tgggcgccgg tgtagctacg   1140
ggccggcacg ccctgctctt tgagcgccat gcaaagcagg ccgatcgtga cctgctcgcc   1200
tgtcgacacc accacgtcca gctcgcgcgg atcgggttgc tgctggactt ccttggccag   1260
cgcaatcagc cggttggtct cgccactcat ggcggacacg acaatcacca gttgatgccc   1320
ttgttcgcgc gccagggcca cacgccgggc gacgttctta atgcgctccg ggttgccgac   1380
cgaggtgccg ccgtacttct gaactatcag cgccatcttg cgttcgatta catctaagta   1440
ggacaaaccg tcattttacc gcattacgcg ggctcttttcc gaaccgccac tccacccaac   1500
ggcctccaaa gtgcttgaat tgcaaacgga tgtttcggga aggactttttc tttatgccaa   1560
agaatcggct gaaggaacaa tttccgataa cgccctgtcc gtgcatatgc accattgcga   1620
tagaacaatt gcagtgcttc gcacgaccga tgttgctatg ccagacgggc gaagtcgtga   1680
cattggcatg ctattgatcg gcatgacgtt tggtagagat tggcaacttg cggcaaccac   1740
gcggaagggc taaaccctt atgggagaag acttctgatg ggcatcggca ctcatcccaa   1800
agcactggga cttgccttgt atgttgctca aatattgatc tatactgaat cgactctata   1860
actaaagtta tagtcttcat gctccgacaa cggcatgccg ttcggatgcc agaatacgta   1920
acagcgcccc tcgtccaaaa caggggcaga tgtggtgttt ggcaaggagt gttcaacgca   1980
tactatgtaa aaagggcaga caaccatg                                     2008
```

<210> SEQ ID NO 26
<211> LENGTH: 40
<212> TYPE: DNA
<213> ORGANISM: Artificial Sequence
<220> FEATURE:

<223> OTHER INFORMATION: primer

<400> SEQUENCE: 26
catggttgtc tgccctttt acatagtatg cgttgaacac                                40

<210> SEQ ID NO 27
<211> LENGTH: 41
<212> TYPE: DNA
<213> ORGANISM: Artificial Sequence
<220> FEATURE:
<223> OTHER INFORMATION: primer

<400> SEQUENCE: 27
tgctctagag gatccgtcga cctgcaggca tgcaagcttg g                             41

<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
agttatactg tcggtaccta tttagcggag c                                        31

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29
tgctctagaa cgggcttttc gccttaagct ctaag                                    35

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30
aattagaaag cgctcaggaa gagttcttca acttc                                    35

<210> SEQ ID NO 31
<211> LENGTH: 41
<212> TYPE: DNA
<213> ORGANISM: Artificial Sequence
<220> FEATURE:
<223> OTHER INFORMATION: primer

<400> SEQUENCE: 31
tgctctagag gatccgtcga cctgcaggca tgcaagcttg g                             41

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
ggagtaagca atgagttata ctgtcggtac ctatttag                                 38

<210> SEQ ID NO 33

<211> LENGTH: 35
<212> TYPE: DNA
<213> ORGANISM: Artificial Sequence
<220> FEATURE:
<223> OTHER INFORMATION: primer

<400> SEQUENCE: 33
tgctctagaa cgggcttttc gccttaagct ctaag        35

<210> SEQ ID NO 34
<211> LENGTH: 45
<212> TYPE: DNA
<213> ORGANISM: Artificial Sequence
<220> FEATURE:
<223> OTHER INFORMATION: primer

<400> SEQUENCE: 34
gggcagacaa ccatgtcgaa gggaaaggtt ttgctggttc tttac        45

<210> SEQ ID NO 35
<211> LENGTH: 45
<212> TYPE: DNA
<213> ORGANISM: Artificial Sequence
<220> FEATURE:
<223> OTHER INFORMATION: primer

<400> SEQUENCE: 35
tttcctgttt tgaaattatt tcttctgtcc ataagctctg gtggc        45

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
tttcaaaaca ggaaaacggt tttccgtcct gtcttgat        38

<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
catggttgtc tgcccttttt acatagtatg cgttgaacac        40

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
ccgtctagat gcacgcgtcc tgttggccgt cag        33

<210> SEQ ID NO 39
<211> LENGTH: 38
<212> TYPE: DNA
<213> ORGANISM: Artificial Sequence
<220> FEATURE:
<223> OTHER INFORMATION: primer

<400> SEQUENCE: 39
cgcggatcca gatcacctcg ttggccagcg gttccttg                               38

<210> SEQ ID NO 40
<211> LENGTH: 40
<212> TYPE: DNA
<213> ORGANISM: Artificial Sequence
<220> FEATURE:
<223> OTHER INFORMATION: primer

<400> SEQUENCE: 40
ccgtctagac gattcaactc tccgaatccg gcctgaagac                             40

<210> SEQ ID NO 41
<211> LENGTH: 35
<212> TYPE: DNA
<213> ORGANISM: Artificial Sequence
<220> FEATURE:
<223> OTHER INFORMATION: primer

<400> SEQUENCE: 41
atcggatccg cgtcttcagc gcgatcgttt caacg                                  35

<210> SEQ ID NO 42
<211> LENGTH: 25
<212> TYPE: DNA
<213> ORGANISM: Artificial Sequence
<220> FEATURE:
<223> OTHER INFORMATION: primer

<400> SEQUENCE: 42
tgcgccgagc gaaccgaagg tcttg                                             25

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
ggccgcattg gccaatgctc gatgc                                             25

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
gcgccctgca ccaccggtag cgaac                                             25

<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
cacgaattcg ctgctcgacc tgcttgtg                                          28

<210> SEQ ID NO 46
<211> LENGTH: 1083
<212> TYPE: DNA
<213> ORGANISM: Sphingomonas sp

```
<400> SEQUENCE: 46
atgcacgcgt cctgttggcc gtcagtagga attgcccac aatttcagtc gaatccccc      60
gaaccttcgc ccggagttct cagcatgcga attgcagtgt tcgataccca ccctacgat    120
gaacaggccc tcacgccgc caacgccagt tttggacacg aactggtctt ctttgaagag    180
cgcttgcacg ataagaccgt cgagctcgcc aaaggcttcg acgttgtgtg tcctttcgtc    240
aattgccgc tgccggcgga ggtcatgcat cgcctggccg aactcggcgt cggtctggtg    300
gcgctacgcg cggccggttt caatggcatt gacatcgctg ccgcccagca cgagggcgtc    360
aaagtgcgc gcgtgccggc ttattcgccg aagccgtgg ccgaacacac ttttgcgctc    420
atcctgacgc tggtgcgcaa gacccatcgc gcatacaacc gtgtgcgcga gcagaacttt    480
tcgctcgacg gccttgaagg cttcacctc acggcaaga ccttcggttc gctcggcgca    540
ggccgcattg ccaatgctc gatgcgcatc gccaaaggcc tgggcatgaa gctgctggcc    600
tacgatccgt acgaaaaccc caagatcgcc gaagaagtcg ggttccagta cgcctcgctg    660
aacgacgtgc tggcccaggc cgacgtgatc tcgctgcacc tgcccctgac cgaccagagc    720
caccacatca tcagccgcga ctcgctggcg cgcaccaaac gcggcgtcgt gattgccaac    780
accagtcgcg gtggactgat cgacacggtg gcgttgatcg acgccctcaa gagcggacag    840
gttggcggcg tgggtctgga cgtctatgaa atggaggaag gcgtgttctt tcacgatctg    900
tccgaccgcc ccttgcagga cgatctgctg gcgcgcctga tgatcttccc caatgccctg    960
atcacctcac accagggctt cctgacccgc gaggcattgc acgccatcgc ccagaccacg   1020
ctgggcaacg ttaccgcctt cgaacgcaag gaaccgctgg ccaacgaggt gatctcagcc   1080
tga                                                                1083

<210> SEQ ID NO 47
<211> LENGTH: 1743
<212> TYPE: DNA
<213> ORGANISM: Sphingomonas sp

<400> SEQUENCE: 47
gtgatcgttg gtgccggtgg tgccggcatg cgcgccgcga ttcaactctc cgaatccggc     60
ctgaagacag ccgttctgtc caaggttttc ccgacccgtt cgcacacggt tgcggcgcaa    120
ggcggtgtgt ccgcttcgct gggtaactcg gagcccgatc actggcactg gcacatgtac    180
gacaccgtca agggttccga ctggctcggc gaccaggacg cgatcgagtt catgtgcaag    240
caggccccgc aagtcgtggt ggaactcgaa cattacggca tgccgttcga ccgtctggac    300
aacggcaaga tttaccaacg cccgttcggc ggtcatatgt cgaacttcgg cgacaagccc    360
gtgcgccgcg cctgcgccgc agccgaccgc accggtcatg ccatgctgca cgcgctctac    420
cagcgcaacg tgcgcgcaaa cacgcagttc ttcgtcgaat ggatggcgct cgatctattg    480
cgtgctgaag acgccgcgt gctgggcgtg atcgctatgg aaatggaaac cggcgacatc    540
accgtattcc aggccaaggc gacgttgttc gctaccggtg gtgcagggcg catctttgct    600
tcgtcgacca acgctttcat caacacgggt gacggccttg gcatgcggc acgtgctggc    660
attccgctgg aagacatgga gttctggcaa ttccacccga ccggcgtggc tggcgcgggc    720
gtgctgatca ccgaaggcgt gcgtggcgaa ggcggcattc tgcgcaacag cgcaggcgaa    780
cgcttcatgg agcgctacgc cccgaacgcc aaggatctgg cttcgcgcga cgtcgtctcg    840
cgcgccatgt tcaccgaaat caacgaaggt cgcggttgcg gccggccaa ggatcacgtg    900
ctgctcgaca tcacgcacct tgacccgaac acgatcatga cccgcctgcc gggtattcgc    960
```

```
                                                  -continued
gaaatctcga tccagttcgc cggcgtcgac ccgatcaagg ctccgattcc ggtcgtgccg    1020
acctgtcact atcagatggg tggcattccg acgaactacc tcggcgaagt cgtcgtgcac    1080
gaccagatcg tgcctggctt ctacgctgca ggcgagtgcg catgcgcctc ggtgcacggt    1140
gcgaaccgcc tgggcacgaa ttcgctgctc gacctgcttg tgttcggcaa gagttcgggc    1200
gagtcgatgg tcgacttcat caagggcgaa cccgccgccg tgccggacat tccgcaagag    1260
cagatcgacc gtgcgttggc gcgcgtagat cgcctggact cgcagcgcga cggtgccaat    1320
gtgcatgaga cgcgcgccgc catgcagcgc acaatgcaga accactgtgg cgtgttccgt    1380
ttcaaggaca tgctggcgca gggcgtggac aagatcacgg aggtcgaagc cgctgtgcgt    1440
cagaccgaga tcaaggacaa gtccaaggtg tggaacaccg cacgccagga agcactggaa    1500
ctggacaacc tcatcgaagt cgccaaggcg acgatggtgt cggccaatgc gcgtaccgaa    1560
tcgcgtggcg cacacgtgcg cgacgacgct ccggataccc cgcaacaccc gaacggccgc    1620
gacgacgaga actggctcaa gcacacccct tggtacaagg agggtagccg cctggactac    1680
aaacccgtca agctcaagcc gctgtccgtt gaaacgatcg cgctgaagac gcgcgcgtac    1740
tga                                                                  1743
```